United States Patent
Knapp et al.

(10) Patent No.: US 12,370,183 B2
(45) Date of Patent: Jul. 29, 2025

(54) COMPOSITIONS AND METHODS FOR TREATING MALARIA

(71) Applicants: Rutgers, The State University of New Jersey, New Brunswick, NJ (US); University of Kentucky Research Foundation, Lexington, KY (US)

(72) Inventors: Spencer Knapp, New Brunswick, NJ (US); Robert D. Barrows, New Brunswick, NJ (US); R. Kiplin Guy, Lexington, KY (US); Jared Hammill, Lexington, KY (US); Christopher Davis, Champaign, IL (US)

(73) Assignees: Rutgers, The State University of New Jersey, New Brunswick, NJ (US); UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 562 days.

(21) Appl. No.: 17/798,391

(22) PCT Filed: Feb. 16, 2021

(86) PCT No.: PCT/US2021/018194
§ 371 (c)(1),
(2) Date: Aug. 9, 2022

(87) PCT Pub. No.: WO2021/167894
PCT Pub. Date: Aug. 26, 2021

(65) Prior Publication Data
US 2023/0139910 A1 May 4, 2023

Related U.S. Application Data

(60) Provisional application No. 62/977,981, filed on Feb. 18, 2020.

(51) Int. Cl.
*A61K 31/4375* (2006.01)
*A61P 33/06* (2006.01)

(52) U.S. Cl.
CPC .......... *A61K 31/4375* (2013.01); *A61P 33/06* (2018.01)

(58) Field of Classification Search
CPC ........................ A61K 31/4375; A61P 33/06
See application file for complete search history.

(56) References Cited

FOREIGN PATENT DOCUMENTS

WO 2016/202898 A1 12/2016

OTHER PUBLICATIONS

International Preliminary Report on Patenability in corresponding PCT Application No. PCT/US2021/018194, mailed Sep. 1, 2022.
International Search Report and Written Opinion in corresponding PCT Application No. PCT/US2021/08194, mailed May 6, 2021.
Floyd et al. "Hit-to-Lead Studies for the Antimalarial Tetrahydroisoquinolone Carboxanilides," J. Med. Chem. 2016, vol. 59 (17), pp. 7950-7952.
Li et al., "Efficient synthesis of 1,9-substituted benzo[h][1,6]naphthyridin-2(1H)-ones and evaluation of their Plasmodium falciparum gametocytocidal activities," ACS Comb Sci. 2017. vol. 19(12), pp. 748-754.
Belen et al., "(+)-SJ733, a clinical candidate for malaria that acts through ATP4 to induce rapid host-mediated clearance of Plasmodium," PNAS, 2015, vol. 112(42), pp. E5455-E5462.

*Primary Examiner* — James D. Anderson
(74) *Attorney, Agent, or Firm* — Leason Ellis LLP

(57) ABSTRACT

Disclosed are methods of treating malaria with tetrahydrobenzonaphtyridine carboxanilide (TBN) derivatives and related pyrrolinones and hydrolysis products thereof. These compounds are active against *Plasmodium falciparum* strains that are resistant to multiple drugs currently on the market. The present invention further relates to novel compounds and pharmaceutical compositions comprising such compounds.

20 Claims, No Drawings

COMPOSITIONS AND METHODS FOR TREATING MALARIA

CROSS-REFERENCE TO RELATED PATENT APPLICATIONS

This application is a U.S. National Phase Application under 35 U.S.C. § 371 of International Patent Application No. PCT/US2021/018194, filed Feb. 16, 2021, and claims the benefit of priority under 35 U.S.C. Section 119(e) of U.S. Application No. 62/977,981, filed Feb. 18, 2020, all of which are incorporated by reference in their entireties. The International Application was published on Aug. 26, 2021 as International Publication No. WO 2021/167894 A1.

FIELD

Disclosed are methods of treating malaria with tetrahydrobenzonaphthyridine carboxanilides (TBN) derivatives and related pyrrolinones and hydrolysis products thereof. These compounds are active against *Plasmodium falciparum* strains that are resistant to multiple drugs currently on the market. The present invention further relates to novel compounds and pharmaceutical compositions comprising such compounds.

BACKGROUND

Malaria is a prevalent disease that continues to infect millions of people every year. In 2017, there were approximately 219 million cases and 435,000 deaths worldwide. Malaria is caused by a single-celled parasite of the genus *Plasmodium*. More than one hundred species of *Plasmodium* have been described, but only five are known to infect humans. The deadliest of them is *Plasmodium falciparum*. This species is responsible for nearly all cases (99.7%) in sub-Sahara Africa and more than sixty percent of cases in Asia. The predominant organism in the Americas, however, is *P. vivax*, which is responsible for more than seventy percent of all cases. The other three species, *P. ovale, P. malariae*, and *P. knowlesi*, are responsible for far fewer infections but still cause significant mortality in certain populations.

The World Health Organization has outlined a plan for the fight against malaria globally. The eradication of malaria is a multi-faceted problem that requires the development of multiple technologies and therapeutics that work complementarily. A widely used preventative technique is the use of insecticide-impregnated mosquito nets. This method has greatly reduced the number of infections but has failed to slow the spread of the disease. Additionally, vaccines have recently been developed that target the pre-erythrocytic stage of the parasite, although with limited success. Small molecule therapeutics, however, continue to be a crucial area of antimalarial research because of their ability to work as preventative agents and cures.

Antimalarial chemotherapies with unique modes of action are known. Quinolines are some of the oldest and most developed antimalarials. The natural product quinine, a quinoline derived from the bark of the cinchona tree, has been used for hundreds of years, and was an important early target for organic synthesis. Quinine, as well as other quinolines such as chloroquine and mefloquine, targets the parasite's ability to polymerize heme. *Plasmodium* relies heavily on hemoglobin as an amino acid source, and digestion of hemoglobin produces heme as a toxic byproduct. Quinolines inhibit the polymerase that is responsible for heme catabolism. Unfortunately, the overuse of quinolines as the first line of defense against malaria has enabled resistant mutants to emerge, which has caused simple therapies of this type to lose effectiveness.

Antifolates are commonly used antimalarials that work orthogonally to quinolines. This class of drugs, which includes sulfadoxine and pyrimethamine, acts by disrupting the formation of pyrimidines in the parasite. As a result, serine, methionine, and DNA synthesis are inhibited. There are two subclasses of antifolates that have separate modes of action, but resistances to both classes have nevertheless emerged.

Atovaquone is an anti-malaria drug which works by disrupting disrupts mitochondrial function in the parasite, although resistances forms quickly. Currently, atovaquone is on the market as part of a combination therapy with an antifolate known as proguanil.[10] The addition of proguanil greatly slows the development of resistance, enabling the dual therapeutic to remain effective as a standard chemical prophylactic.

The current standard for antimalarial treatment features artemisinin combination therapies (ARTs). Artemisinin is a natural product found in the dried leaves of the qinghao plant, a Chinese herb used to treat malaria since 281 AD. Artemisinin along with its derivatives are some of the most rapidly-acting antimalarials currently in use. Unfortunately, the half-lives for these compounds are less than an hour. To compensate, these compounds are used in combination with other antimalarials that have a longer in vivo half-life. This helps to prevent reinfection from dormant liver stage parasites and to slow the emergence of resistant strains. Two common ARTs are artemether and lumefantrine (a heme polymerase inhibitor), and artesunate with pyronaridine. Artemisinin type compounds do not bind to a single target. It is believed that they disrupt multiple proteins after activation by the iron-rich environment within the parasite. This behavior can be attributed to the compound's unique peroxide bridge. $Fe^{2+}$, present from hemoglobin digestion, catalyzes the breaking of the peroxide bond to form carbon-centered radicals. These radicals then react with multiple proteins in the parasite. Despite this robust mode of action, mutants resistant to artemisinin have started to appear.

There is an unmet need in the art to develop novel anti-malaria drugs with druggable properties, high potency, and acceptable safety profile.

SUMMARY

The present invention relates to methods of treating malaria with tetrahydrobenzonaphtyridine carboxanilide (TBN) derivatives and related pyrrolinones and hydrolysis products thereof. These compounds are active against *Plasmodium falciparum* strains that are resistant to multiple drugs currently on the market. The present invention further relates to novel compounds and pharmaceutical compositions comprising such compounds. The compounds have been synthesized and tested for their potency in the 3D7 strain of *Plasmodium falciparum*. Their cytotoxicity was also tested in the BJ human fibroblast line. No compounds show significant cytotoxicity.

In one embodiment, the present invention relates to a compound represented by the structure of formula (I):

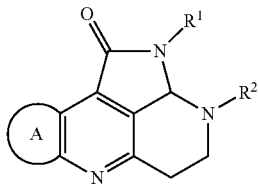

(I)

or a derivative of compound (I) selected from the group consisting of:
(a) an iminium form of compound (I) represented by the structure of formula (I-a):

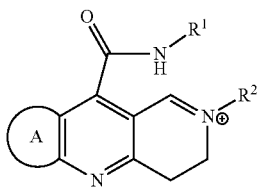

(I-a)

(b) a compound represented by the structure of formula (I-b):

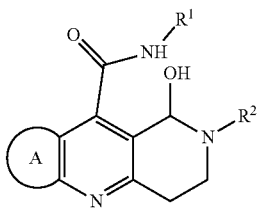

(I-b)

(c) a compound represented by the structure of formula (I-c):

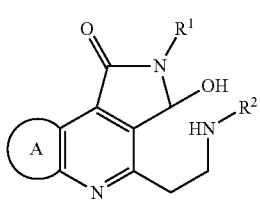

(I-c)

wherein
A is absent, or an unsubstituted or substituted cycloalkyl, aryl, ferrocenyl, heterocycloalkyl or heteroaryl group;
$R^1$ is selected from the group consisting of alkyl, cycloalkyl, aryl, ferrocenyl, heterocycloalkyl, heteroaryl, cycloalkylalkyl, arylalkyl, heterocycloalkylaryl, heteroarylalkyl, each of which is unsubstituted or substituted with at least one $R^3$;
$R^2$ is selected from the group consisting of H, alkyl, haloalkyl, hydroxyalkyl, cyanoalkyl, aminoalkyl, sulfonylalkyl, alkenyl, cycloalkyl, aryl, ferrocenyl, heterocycloalkyl, heteroaryl, arylalkyl, cycloalkylalkyl, heterocycloalkylalkyl, heteroarylalkyl, alkyloxyalkyl, aryloxyalkyl, heteroalkyloxyalkyl, heterocycloalkyloxyalkyl, $—SO_2R^b$, $—(CRR')_mC(O)R^a$, $—(CRR')_mC(O)OR^a$, and $—(CRR')_mC(O)NRR'$;
$R^3$ is independently at each occurrence selected from the group consisting of halogen, CN, hydroxy, alkyloxy, aryloxy, cycloalkyloxy, heterocycloalkyloxy, heteroaryloxy $—SO_2R^b$, NRR' and $—NHC(=O)R$;
$R^a$, R and R' are each independently H or alkyl;
$R^b$ is H, alkyl or NRR';
m is 0, 1, 2, 3, 4, 5 or 6;
and enantiomers, diastereomers, polymorphs, salts, solvates and deuterated analogues thereof.

In another embodiment, the present invention relates to a pharmaceutical composition comprising a compound represented by the structure of formula (I), (I-a), (I-b) or (I-c) as defined above, and a pharmaceutically acceptable carrier or excipient.

In further embodiments, the present invention relates to a method of treating or inhibiting malaria, or reducing the symptoms of malaria, comprising the step of administering to a subject in need thereof a therapeutically effective amount of a compound of formula (I) (I-a), (I-b) or (I-c) as defined above, or a pharmaceutical composition comprising such compound.

In further embodiments, the present invention relates to a method of treating or inhibiting malaria, or reducing the symptoms of malaria, comprising the step of administering to a subject in need thereof a therapeutically effective amount of a compound represented by the structure of formula (II), or a pharmaceutical composition comprising such compound

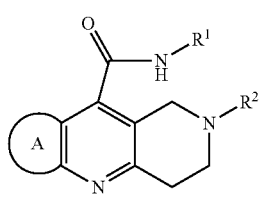

(II)

wherein
A is absent, or an unsubstituted or substituted cycloalkyl, aryl, ferrocenyl, heterocycloalkyl or heteroaryl group;
$R^1$ is selected from the group consisting of alkyl, cycloalkyl, aryl, ferrocenyl, heterocycloalkyl, heteroaryl, cycloalkylalkyl, arylalkyl, heterocycloalkylaryl, heteroarylalkyl, each of which is unsubstituted or substituted with at least one $R^3$;
$R^2$ is selected from the group consisting of H, alkyl, haloalkyl, hydroxyalkyl, cyanoalkyl, aminoalkyl, sulfonylalkyl, alkenyl, cycloalkyl, aryl, ferrocenyl, heterocycloalkyl, heteroaryl, arylalkyl, cycloalkylalkyl, heterocycloalkylalkyl, heteroarylalkyl, alkyloxyalkyl, aryloxyalkyl, heteroalkyloxyalkyl, heterocycloalkyloxyalkyl, $—SO_2R^b$, $—(CRR')_mC(O)R^a$, $—(CRR')_mC(O)OR^a$, and $—(CRR')_mC(O)NRR'$;
$R^3$ is independently at each occurrence selected from the group consisting of halogen, CN, hydroxy, alkyloxy, aryloxy, cycloalkyloxy, heterocycloalkyloxy, heteroaryloxy $—SO_2R^b$, NRR' and $—NHC(=O)R$;

$R^a$, R and R' are each independently H or alkyl;
$R^b$ is H, alkyl or NRR';
m is 0, 1, 2, 3, 4, 5 or 6;
and enantiomers, diastereomers, polymorphs, salts, solvates and deuterated analogues thereof.

DETAILED DESCRIPTION

Anti-Malaria Drugs

In one embodiment, the present invention relates to a compound represented by the structure of formula (I):

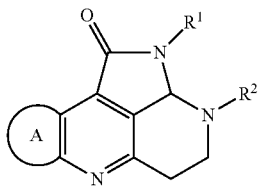

(I)

and enantiomers, diastereomers, polymorphs, salts, solvates and deuterated analogues thereof.

In another embodiment, the present invention relates to an iminium derivative of the compound of formula (I), which is represented by the structure of formula (I-a):

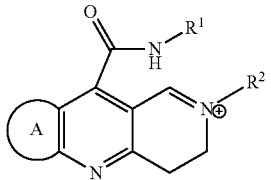

(I-a)

and enantiomers, diastereomers, polymorphs, salts, solvates and deuterated analogues thereof.

In another embodiment, the present invention relates to a compound represented by the structure of formula (I-b). In some embodiments, the compound of formula (I-b) is a hydrolysis product of the compound of formula (I):

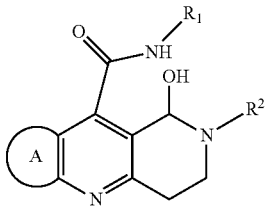

(I-b)

In another embodiment, the present invention relates to a compound represented by the structure of formula (I-c). In some embodiments, the compound of formula (I-c) is a hydrolysis product of the compound of formula (I):

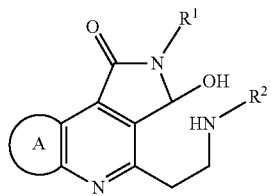

(I-c)

and enantiomers, diastereomers, polymorphs, salts, solvates and deuterated analogues thereof.

In each of compounds (I), (I-a), (I-b) and (I-c):

A is absent, or an unsubstituted or substituted cycloalkyl, aryl, ferrocenyl, heterocycloalkyl or heteroaryl group;

$R^1$ is selected from the group consisting of alkyl, cycloalkyl, aryl, ferrocenyl, heterocycloalkyl, heteroaryl, cycloalkylalkyl, arylalkyl, heterocycloalkylaryl, heteroarylalkyl, each of which is unsubstituted or substituted with at least one $R^3$.

$R^2$ is selected from the group consisting of H, alkyl, haloalkyl, hydroxyalkyl, cyanoalkyl, aminoalkyl, sulfonylalkyl, alkenyl, cycloalkyl, aryl, ferrocenyl, heterocycloalkyl, heteroaryl, arylalkyl, cycloalkylalkyl, heterocycloalkylalkyl, heteroarylalkyl, alkyloxyalkyl, aryloxyalkyl, heteroalkyloxyalkyl, heterocycloalkyloxyalkyl, —$SO_2R^b$, —$(CRR')_mC(O)R^a$, —$(CRR')_mC(O)OR^a$, and —$(CRR')_mC(O)NRR'$;

$R^3$ is independently at each occurrence selected from the group consisting of halogen, CN, hydroxy, alkyloxy, aryloxy, cycloalkyloxy, heterocycloalkyloxy, heteroaryloxy —$SO_2R^b$, NRR' and —NHC(=O)R;

$R^a$, R and R' are each independently H or alkyl;
$R^b$ is H, alkyl or NRR'; and
m is 0, 1, 2, 3, 4, 5 or 6.

In other embodiments, the present invention relates to compounds of formula (II), for use in the treatment of malaria:

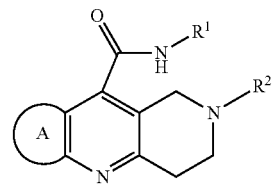

(II)

wherein

A is absent, or an unsubstituted or substituted cycloalkyl, aryl, ferrocenyl, heterocycloalkyl or heteroaryl group;

$R^1$ is selected from the group consisting of alkyl, cycloalkyl, aryl, ferrocenyl, heterocycloalkyl, heteroaryl, cycloalkylalkyl, arylalkyl, heterocycloalkylaryl, heteroarylalkyl, each of which is unsubstituted or substituted with at least one $R^3$.

$R^2$ is selected from the group consisting of H, alkyl, haloalkyl, hydroxyalkyl, cyanoalkyl, aminoalkyl, sulfonylalkyl, alkenyl, cycloalkyl, aryl, ferrocenyl, heterocycloalkyl, heteroaryl, arylalkyl, cycloalkylalkyl, heterocycloalkylalkyl, heteroarylalkyl, alkyloxyalkyl, aryloxyalkyl, heteroalkyloxyalkyl, heterocycloalkyloxyalkyl, —$SO_2R^b$, —$(CRR')_mC(O)R^a$, —$(CRR')_mC(O)OR^a$, and —$(CRR')_mC(O)NRR'$;

$R^3$ is independently at each occurrence selected from the group consisting of halogen, CN, hydroxy, alkyloxy, aryloxy, cycloalkyloxy, heterocycloalkyloxy, heteroaryloxy —$SO_2R^b$, NRR' and —NHC(=O)R;

$R^a$, R and R' are each independently H or alkyl;

$R^b$ is H, alkyl or NRR'; and m is 0, 1, 2, 3, 4, 5 or 6;

and enantiomers, diastereomers, polymorphs, salts, solvates and deuterated analogues thereof.

In some embodiments, ring A is an unsubstituted or substituted cyclohexyl, phenyl or pyridyl. In one embodiment ring A is a phenyl substituted with at least one halogen, preferably chloro.

In one embodiment, $R^1$ is an unsubstituted or substituted phenyl, benzyl, alkyl, cycloalkyl or heterocycloalkyl.

In one embodiment, $R^1$ is an unsubstituted or substituted phenyl represented by the structure:

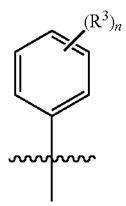

wherein $R^3$ is as above, and n is selected from the group consisting of 1, 2, 3, 4 and 5. In some embodiments, $R^3$ is selected from the group consisting of halogen, alkyloxy and cyano, and n is 1 or 2. In one embodiment $R^3$ is a halogen, preferably chloro, fluoro or bromo. In other embodiments, $R^3$ may be sulfonylalkyl (e.g., $SO_2CH_3$), sulfonylamido (e.g., $SO_2N(CH_3)_2$), —$SO_2N(CH_2CH_3)_2$), dialkylamino (e.g., $NMe_2$) or dialkylamido. Representative compounds are shown below:

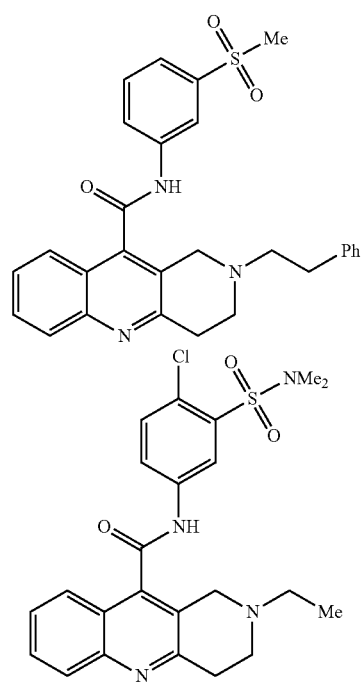

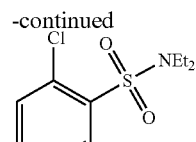
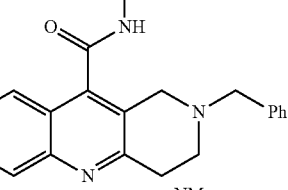
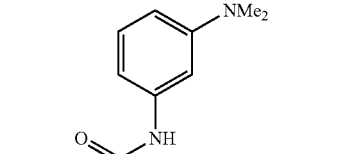
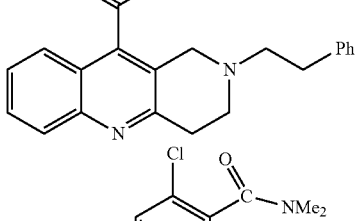
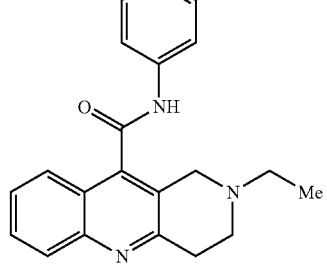

In other embodiments, $R^3$ is selected from the group consisting of chloro, fluoro, bromo, methoxy, cyano and hexahydrofurofuranyloxy.

In some embodiments, wherein $R^2$ is selected from the group consisting of H, an unsubstituted or substituted benzyl, phenethyl, piperazinyl, pyridinylalkyl, pyrimidinylalkyl, thiazolylalkyl, pyrazolylalkyl, imidazolylalkyl, triazolylalkyl, allyl, alkyl, carbomethoxyalkyl, cyclopropylalkyl, ethoxyalkyl, tetrahydropyranyloxylalkyl, haloalkyl, cyanoalkyl, hydroxyalkyl, N,N-dimethylcarboxamidoalkyl, —C(=O)—$CH_2OR^a$ wherein $R^a$ is alkyl, phthalimidealkyl, aminoalkyl, N,N-dimethylaminoalkyl, sulfonylalkyl and carboxyalkyl.

In other embodiments, $R^2$ is selected from the group consisting of benzyl, phenethyl and alkyl.

All stereoisomers of the above compounds are contemplated, either in admixture or in pure or substantially pure form. The compounds can have asymmetric centers at any of the atoms. Consequently, the compounds can exist in enantiomeric or diastereomeric forms or in mixtures thereof. The present invention contemplates the use of any racemates (i.e., mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. In addition, several of the compounds of the invention contain one or more double bonds. The present invention intends to encompass all structural and geometrical isomers including cis, trans, E and Z isomers, independently at each occurrence.

One or more of the compounds of the invention, may be present as a salt. The term "salt" encompasses both basic and acid addition salts, including but not limited to, carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids.

The term "organic or inorganic cation" refers to counter-ions for the anion of a salt. The counter-ions include, but are not limited to, alkali and alkaline earth metals (such as lithium, sodium, potassium, barium, aluminum and calcium); ammonium and mono-, di- and tri-alkyl amines such as trimethylamine, cyclohexylamine; and the like.

The present invention also includes solvates of the compounds of the present invention and salts thereof. "Solvate" means a physical association of a compound of the invention with one or more solvent molecules. This physical association involves varying degrees of ionic and covalent bonding, including hydrogen bonding. In certain instances, the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of the compounds of the present invention and salts thereof. The term "polymorph" refers to a particular crystalline or amorphous state of a substance, which can be characterized by particular physical properties such as X-ray diffraction, IR or Raman spectra, melting point, and the like.

The present invention also includes deuterated derivatives and analogues of the compounds described herein. The term "deuterated derivative" or "deuterated analogue", used herein interchangeably, means that one or more of the carbon atoms may be substituted by a deuterium atom instead of a hydrogen atom.

Chemical Definitions

An "alkyl" group refers to any saturated aliphatic hydrocarbon, including straight-chain and branched-chain alkyl groups. In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. The alkyl group may be unsubstituted or substituted by one or more groups selected from halogen, hydroxy, alkoxy, cyano, aryloxy, cycloalkyloxy, heterocycloalkyloxy, heteroaryloxy carbonyl, amido, alkylamido, dialkylamido, nitro, amino, alkylamino, dialkylamino, carboxyl, thio and thioalkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms designated here as $C_2$-$C_8$-alkenyl. In another embodiment, the alkenyl group has 2-6 carbon atoms in the chain designated here as $C_2$-$C_6$-alkenyl. Exemplary alkenyl groups include ethenyl, propenyl, n-butenyl, i-butenyl, 3-methylbut-2-enyl, n-pentenyl, heptenyl, octenyl, cyclohexyl-butenyl and decenyl. The alkenyl group can be unsubstituted or substituted through available carbon atoms with one or more groups defined hereinabove for alkyl.

The term "cycloalkyl" used herein alone or as part of another group refers to any saturated or unsaturated (e.g., cycloalkenyl) monocyclic or polycyclic group. Non-limiting examples of cycloalkyl groups are $C_3$-$C_7$ cycloalkyls such as cyclopropyl, cyclobutyl, cyclopentyl, cyclohexyl or cycloheptyl. Non-limiting examples of cycloalkenyl groups include cyclopentenyl, cyclohexenyl and the like. The cycloalkyl group can be unsubstituted or substituted with any one or more of the substituents defined above for alkyl.

The term "aryl" used herein alone or as part of another group refers to an aromatic ring system containing from 5-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "ferrocenyl" or "ferrocene aryls", as used herein, denotes compounds having the following structure. Ferrocenyl aryls can form a bond to the rest of the molecule through one of the carbons of the 5-membered aryl group.

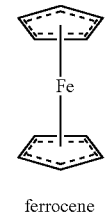

ferrocene

The term "heteroaryl" used herein alone or as part of another group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. If nitrogen is a ring atom, the present invention also contemplates the N-oxides of the nitrogen containing heteroaryls. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "heterocyclic ring" or "heterocycloalkyl" used herein alone or as part of another group refers to a five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings can be saturated, fully unsaturated or partially unsaturated, with fully saturated rings being preferred. Preferred heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, dihydrothiazolyl, and the like. The heterocycloalkyl group can be unsubstituted or substituted through available atoms with one or more groups defined hereinabove for alkyl.

Methods of Treatment:

In further embodiments, the present invention relates to a method of treating or inhibiting malaria, or reducing the symptoms of malaria, comprising the step of administering to a subject in need thereof a therapeutically effective amount of a compound of formula (I) (I-a), (I-b), (I-c) or (II) as defined above, or a pharmaceutical composition comprising such compound.

In further embodiments, the present invention relates to a compound of formula (I) (I-a), (I-b), (I-c) or (II) as defined above, or a pharmaceutical composition comprising such compound, for use in the treatment of malaria, or for use in inhibiting or reducing the symptoms of malaria.

As used herein and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

As used herein and as well understood in the art, the term an "effective amount," "sufficient amount" or "therapeutically effective amount" of an agent as used herein interchangeably, is that amount sufficient to effectuate beneficial or desired results, including preclinical and/or clinical results and, as such, an "effective amount" or its variants depends upon the context in which it is being applied. The response is, in some embodiments, preventative, in others therapeutic, and in others a combination thereof. The term "effective amount" also includes the amount of a compound of the invention, which is "therapeutically effective" and which avoids or substantially attenuates undesirable side effects.

As used herein and as well known in the art, and unless otherwise defined, the term "subject" means an animal, including but not limited a human, monkey, cow, horse, sheep, pig, chicken, turkey, quail, cat, dog, mouse, rat, rabbit, or guinea pig. In one embodiment, the subject is a mammal and in another embodiment the subject is a human malaria patient.

Dosing and Dosing Regimens

The compositions described herein generally comprise a therapeutically effective amount of a compound provided herein, that is, an amount effective to prevent, ameliorate, lessen or inhibit a malaria infection in a mammal. Such amounts typically comprise from about 0.1 to about 1000 mg of the compound per kilogram of body weight of the mammal to which the composition is administered. Therapeutically effective amounts can be administered according to any dosing regimen satisfactory to those of ordinary skill in the art, for example once-a-day (qd), twice-a-day (b.i.d.), thrice daily (t.i.d), three times weekly, once a month, thrice a month, and the like.

Pharmaceutical Compositions

The present invention thus provides pharmaceutical compositions comprising the compounds of the invention, and a pharmaceutically acceptable carrier.

The pharmaceuticals can be safely administered orally or non-orally. Routes of administration include, but are not limited to, oral, topical, mucosal, nasal, parenteral, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic, transdermal, rectal, buccal, epidural and sublingual.

The pharmaceutical compositions may be formulated as tablets (including e.g., film-coated tablets, sublingual tablets and orally disintegrating tablets), powders, granules, dragées, pellets, pills, capsules (including soft capsules) and the like.

The term "pharmaceutically acceptable" means approved by a regulatory agency of the Federal or a state government or listed in the U. S. Pharmacopeia or other generally recognized pharmacopeia for use in animals and, more particularly, in humans.

Pharmacologically acceptable carriers that may be used include various organic or inorganic carriers including, but not limited to excipients, lubricants, binders, disintegrants, water-soluble polymers and basic inorganic salts. The pharmaceutical compositions may further include additives such as, but not limited to, preservatives, anti-oxidants, coloring agents, sweetening agents, souring agents, bubbling agents and flavorings.

Suitable excipients include, e.g., lactose, D-mannitol, starch, cornstarch, crystalline cellulose, light silicic anhydride and titanium oxide. Suitable lubricants include, e.g., magnesium stearate, sucrose fatty acid esters, polyethylene glycol, talc and stearic acid. Suitable binders include, e.g., hydroxypropyl cellulose, hydroxypropyl methyl cellulose, crystalline cellulose, α-starch, polyvinylpyrrolidone, gum arabic powder, gelatin, pullulan and low-substituted hydroxypropyl cellulose. Suitable disintegrants include, e.g., cross-linked povidone (any cross-linked 1-ethenyl-2-pyrrolidinone homo-polymer including polyvinylpyrrolidone (PVP) and 1-vinyl-2-pyrrolidinone homo-polymer), cross-linked carmellose sodium, carmellose calcium, carboxymethyl starch sodium, low-substituted hydroxypropyl cellulose, cornstarch and the like. Suitable water-soluble polymers include, e.g., cellulose derivatives such as hydroxypropyl cellulose, polyvinylpyrrolidone, hydroxypropyl methyl cellulose, methyl cellulose and carboxymethyl cellulose sodium, sodium polyacrylate, polyvinyl alcohol, sodium alginate, guar gum and the like.

Suitable preservatives include, e.g., sodium benzoate, benzoic acid, and sorbic acid. Suitable antioxidants include, e.g., sulfites, ascorbic acid and α-tocopherol. Suitable coloring agents include, e.g., food colors such as Food Color Yellow No. 5, Food Color Red No. 2 and Food Color Blue No. 2 and the like. Suitable sweetening agents include, e.g., dipotassium glycyrrhetinate, aspartame, stevia and thaumatin. Suitable souring agents include, e.g., citric acid (citric anhydride), tartaric acid and malic acid. Suitable bubbling agents include, e.g., sodium bicarbonate. Suitable flavorings include synthetic substances or naturally occurring substances, including, e.g., lemon, lime, orange, menthol and strawberry.

Furthermore, at times, the pharmaceutical compositions may be formulated for parenteral administration (subcutaneous, intravenous, intra-arterial, transdermal, intraperitoneal or intramuscular injection) and may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. The above formulations may also be used for direct intra-tumoral injection. Further, in order to minimize or eliminate irritation at the site of injection, the compositions may contain one or more non-ionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

Water is a preferred carrier when the pharmaceutical composition is administered intravenously. Saline solutions and aqueous dextrose and glycerol solutions can also be employed as liquid carriers, particularly for injectable solutions.

The tablets and other solid dosage forms of the pharmaceutical compositions described herein may optionally be scored or prepared with coatings and shells, such as enteric coatings and other coatings well known in the art. They may also be formulated so as to provide slow or controlled release of the active ingredient therein using, for example, hydroxypropyl methyl cellulose in varying proportions to provide the desired release profile, other polymer matrices and the like. The compositions may alternatively be formulated for delayed release or immediate release of the active ingredient. The active ingredient may also be in microencapsulated form, if appropriate, with one or more of the above-described excipients.

The tablets and other solid dosage forms may be made by compression or molding, optionally with one or more excipients as is known in the art. For example, molded tablets may be made by molding in a suitable machine a mixture of the powdered active ingredient moistened with an inert liquid diluent.

The present subject matter described herein will be illustrated more specifically by the following non-limiting examples, it being understood that changes and variations can be made therein without deviating from the scope and the spirit of the disclosure as hereinafter claimed. It is also understood that various theories as to why the disclosure works are not intended to be limiting.

Methods of Synthesis

The present invention further provides process for preparing a compound represented by the structure of formula (I), or enantiomers, diastereomers, polymorphs, salts, solvates and deuterated analogues thereof

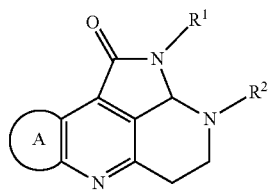

(I)

by reacting a compound of formula (II)

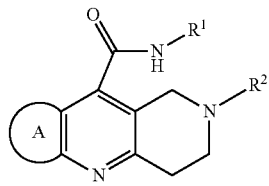

(II)

with an oxidizing agent, such as but not limited to mercuric salts and iodine ($I_2$).

In other embodiments, the present invention relates to a process for converting the compound of formula (I) into a compound of formula (I-a) by equilibrium in aqueous acid.

In other embodiments, the present invention relates to a process for converting the compound of formula (I) into its hydrolysis products of formula (I-b) or (I-c) by treating the compound of formula (I) with aqueous media.

EXAMPLES

The following are examples that illustrate embodiments for practicing the disclosure described herein. These examples should not be construed as limiting.

Example 1: Identification of Tetrahydrobenzonaphthyridine Carboxanilides (TBNs) as Anti-Malaria Drugs Tetrahydrobenzonaphthyridine carboxanilides (TBNs) such as 66 are a class of compounds that has previously only been investigated as therapeutics for dengue virus (Li, L et al. *Chem. Biol. Drug Des.* 2015, 86 (3), 255-264), and as inhibitors of autotaxin (WO 2010/060532).

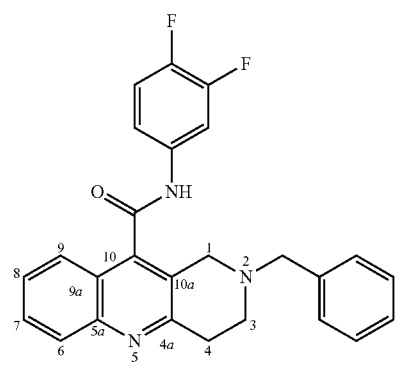

66

Validation Data
3D7 $EC_{50}$: 20.4 nM
K1 $EC_{50}$: 10.8 nM

High Throughput Screening

A high-throughput screen performed against the *Plasmodium* parasite. About 8,000 compounds were screened. Each hit was tested against resistant *P. falciparum* variants K1, V1S, D10DD, ATP4 1247, and $C_2B$. Potency against these assays assured that the chemotype acts through a mechanism distinct from that of halofantrine, chloroquine, mefloquine, pyrimethamine, proguanil, atovaquone, and (+)SJ733. The toxicity of the compounds was also measured by testing their lethality against a BJ cell line (human fibroblasts). No TBNs were toxic. A structure activity investigation was performed in order to improve the $EC_{50}$ of the TBNs to the single-digit nanomolar range, as well as to increase the water solubility.

1.1 Synthesis of Desbenzo TBN Analogue

A desbenzo derivative (68) was prepared as an analogue of the 3,4-difluoro-carboxanilide 66.

The synthesis of 68 is shown in Scheme 1. The hydroxyl group of chloropyridinyl 69 was first protected with p-methoxybenzyl (PMB) chloride to form ether 70. The ether was then coupled with vinyl trifluoroborane under Suzuki-Miyaura conditions to produce 2-vinylpyridine 71. Benzylamine was added in conjugate fashion under acidic conditions. The hydroxy group on the resulting secondary amine 72 was revealed by deprotection with trifluoroacetic acid. NMR analysis indicates that the dominant form of the product is the pyridinone (73), as drawn, and not the pyridinol tautomer.

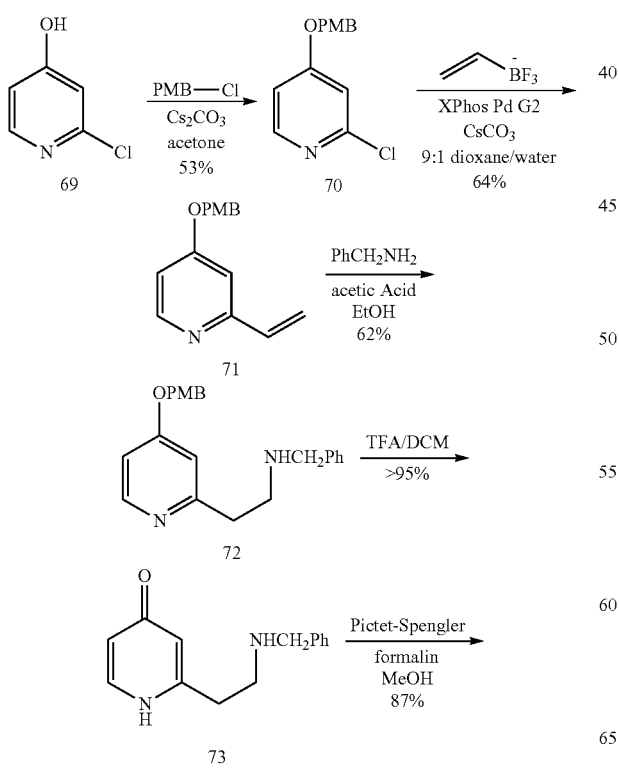

Scheme 1: The synthesis of 61

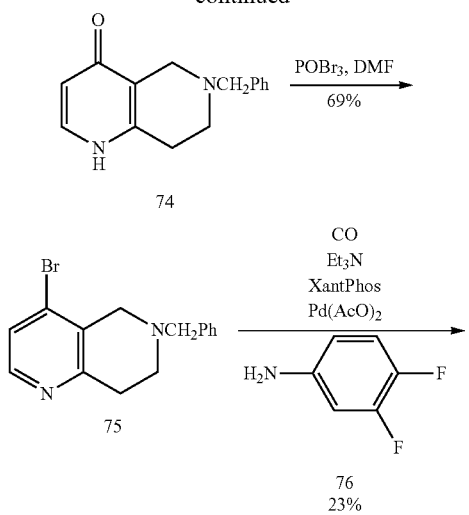

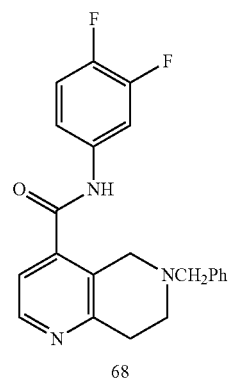

PMB = p-methoxybenzyl

The Pictet-Spengler reaction (Youn, S. W. *The Pictet-Spengler Reaction: Efficient Carbon-Carbon Bond Forming Reaction in Heterocyclic Synthesis;* 2006; Vol. 38) was utilized to complete the assembly of the tetrahydronaphthyridine core: (1) the benzylamino site of pyridinone 73 condenses with formaldehyde to produce an iminium intermediate, and (2) this intermediate cyclizes via a Mannich-type mechanism to form the tetrahydronaphthyridinone 74. Next, transformation of 74 to the bromopyridine 75 was affected by a bromo-Vilsmeier reagent formed in situ from the mixture of potassium oxybromide and dimethylformamide. The amide was made directly from the bromide by using a palladium catalyzed insertion-coupling of carbon monoxide and aniline (76)[6] to form the final tetrahydronaphthyridine carboxamide 68 in 23% yield.

A second route (Scheme 2) was developed with the purpose of reducing steps and improving the efficiency. 2-Chloro-4-methoxypyridine (77) was coupled with vinyl trifluoroborate under conditions comparable to those for the transformation of 70. Benzylamine was added to the resulting vinyl pyridine 78 to provide secondary amine 79. Finally, methyl ether 79 was demethylated with sodium octanethiolate, and the product matches that from the previous route.

Scheme 2: Alternate route to 68

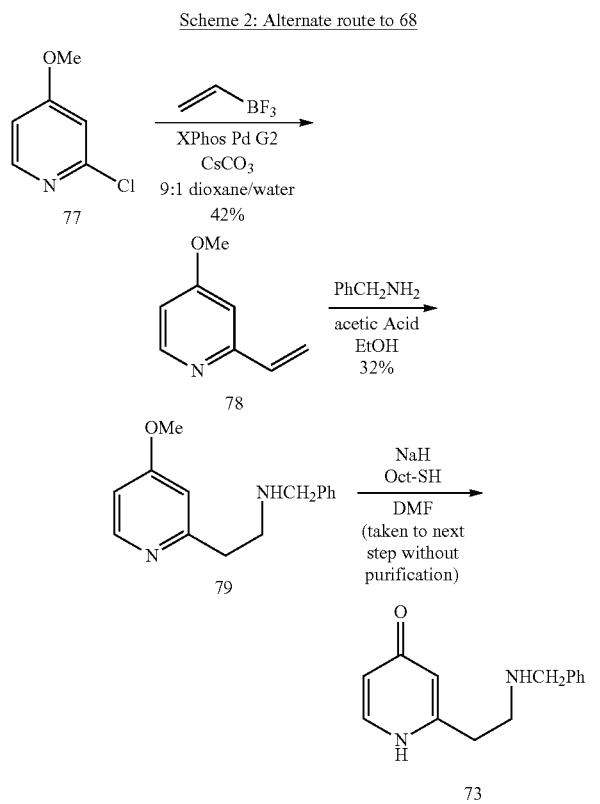

Scheme 3: TBN synthesis that diverges at N-2

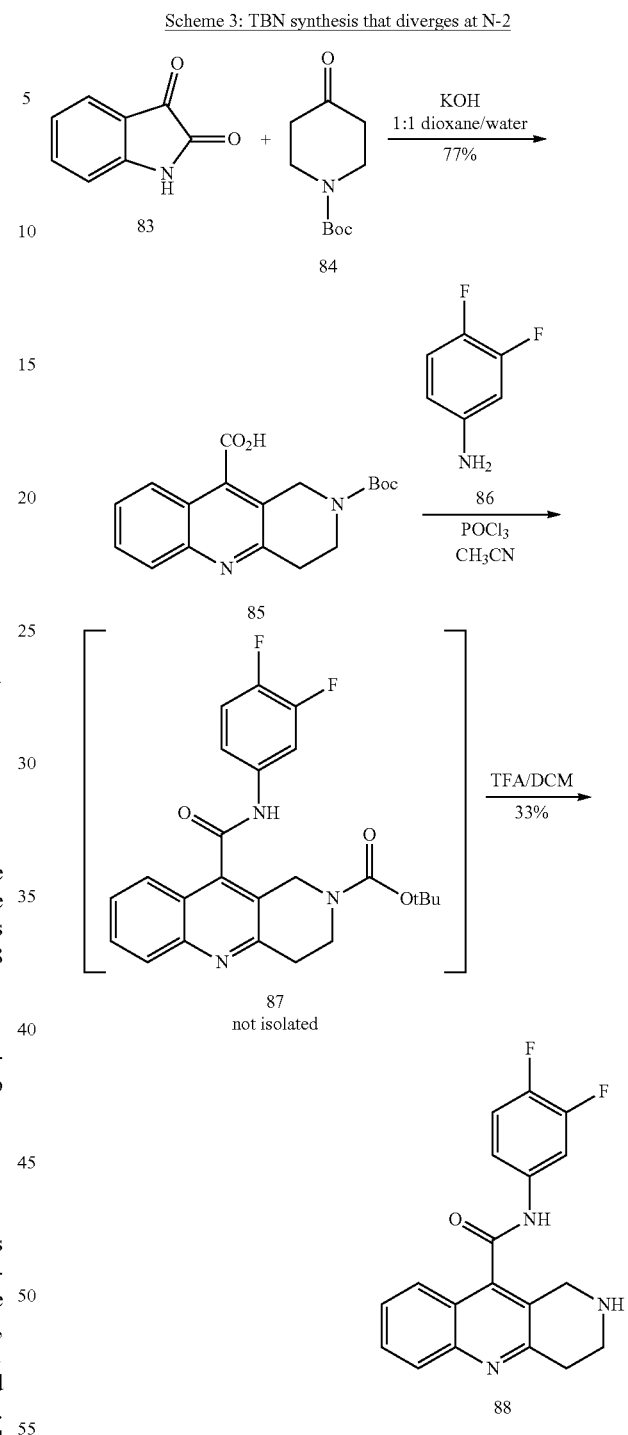

The deletion of the benzo group successfully reduced the crystallinity and solubility of the scaffold. For example, the melting point of 66 is 220° C. and the desbenzo analogue is 83.5° C. Despite the increased solubility versus 66, amide 68 has a modest $EC_{50}$ at 3,480 nM.

Structure-Activity Studies

SAR investigation around the TBN structure was performed at three sites: (1) the carboxanilide; (2) the benzo ring, and (3) the N–2 substituent.

1.2 Structure-Activity Studies of the N-Substituent

Compound 88 was prepared as a precursor of compounds having a variety of N–2 substituents. The tetrahydronaphthyridine core was synthesized in the first step by using the Pfitzinger reaction (Moskalenko, A. I.; Boeva, A. V.; Boev, V. I. Heterocyclic Ketones in the Pfitzinger Reaction. *Russ. J. Gen. Chem.* 2011, 81 (2), 397-404)). Isatin 83 was treated with potassium hydroxide followed by piperidinone 84. After workup, the carboxylic acid product (85) was isolated in over 70% yield via a simple filtration. The carboxylic acid was brought to the de-protected carboxamide in one process. Acid 85 was mixed with 3,4-difluoroaniline 86 and treated with phosphorous oxychloride without a base. After thirty minutes, the reaction was filtered without quenching. The $^2$N-boc amide 87 is normally not isolated from the resulting solid. Instead, the crude product is taken directly to the next step. Trifluoroacetic acid removes the carbamate protecting group to afford amine 88 as a white solid. The secondary amine precursor 88 was used for making multiple TBN analogues with varying functionalities at the N–2 position.

Substituents were installed at N–2 by using a variety of methods. Reductive alkylation (Abdel-Magid, A. F.; Mehrman, S. J. A Review on the Use of Sodium Triacetoxyborohydride in the Reductive Amination of Ketones and Aldehydes. *Org. Process Res. Dev.* 2006, 10 (5), 971-1031) was a dependable technique that produced over fifteen analogues. Conjugate additions and nucleophilic substitutions provided most of the others. A type of reductive alkylation that uses carboxylic acids instead of aldehydes (the Beller reduction) led to two analogues (Sorribes, I.; Junge, K.; Beller, M. Direct Catalytic N-Alkylation of Amines with Carboxylic Acids. *J. Am. Chem. Soc.* 2014, 136 (40), 14314-14319. Some of the compounds listed were synthesized through other means, or were derived from other TBNs. Compounds 66 and 128 were produced by the amidation of acids 132 and 133, which had the corresponding substitution already installed. TBNs 93, and 94 were produced from the Pfitzinger products formed from the condensation of isatin with (R)-1-(1-phenylethyl)piperidin-4-one (134) and (S)-1-(1-phenylethyl)piperidin-4-one (135), respectively. These compounds and their potency in the 3D7 and K1 (when available) strains are displayed in Table 1.

Results from Table 1 show nearly fifty TBNs with $EC_{50}$ values that range from 20 nanomolar to greater than 19 micromolar.

TABLE 1

SAR study of the TBNs at N-2

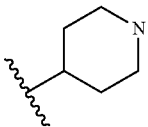

| Compound | $R^2$ | ClogP | 3D7 Mean $EC_{50}$ (μM) | K1 $EC_{50}$ (μM) | BJ $EC_{50}$ (μM) (cytotoxicity) |
|---|---|---|---|---|---|
| 89 | 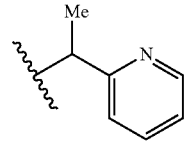 | 4.97 | 0.0257 ± 0.00583 (n = 2) | | |
| 90 | 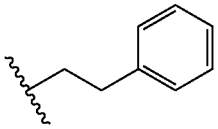 | 4.32 | 0.0603 ± 0.0234 (n = 4) | 0.0439 | >11.7 |
| 91 |  | 5.46 | 0.117 ± 0.102 (n = 3) | 0.0839 | |
| 92 | 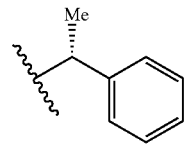 [SMILES: *[C@H](C)c1ccccc1] | 4.51 | 0.128 ± 0.0238 (n = 4) | 0.0719 | >23.3 |
| 93 | 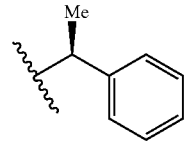 [SMILES: *[C@@H](C)c1ccccc1] | 5.81 | 0.131 ± 0.00623 (n = 5) | 0.064 | |
| 94 | 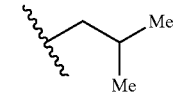 | 5.81 | 0.154 ± 0.0285 (n = 6) | 0.148 | |
| 95 | | 4.97 | 0.154 ± 0.162 (n = 6) | 0.121 | |

TABLE 1-continued

SAR study of the TBNs at N-2

| Compound | R² | ClogP | 3D7 Mean EC₅₀ (μM) | K1 EC₅₀ (μM) | BJ EC₅₀ (μM) (cytotoxicity) |
|---|---|---|---|---|---|
| 96 | iPr (Me, Me) | 4.36 | 0.215 ± 0.269 (n = 3) | 0.177 | |
| 97 | CH₂CH(Me)C(O)OMe | 4.15 | 0.328 ± 0.17 (n = 6) | 0.185 | |
| 98 | CH₂CH₂-(2-pyridyl) | 3.97 | 0.329 ± 0.0232 (n = 2) | | |
| 99 | n-butyl | 5.1 | 0.37 ± 0.376 (n = 3) | 0.102 | |
| 100 | CH₂-(3-fluorophenyl) | 5.65 | 0.412 ± 0.291 (n = 6) | 0.161 | |
| 101 | CH₂-cyclopropyl | 4.71 | 0.429 ± 0.303 (n = 6) | 0.272 | |
| 102 | CH₂CH₂CH₂-O-(tetrahydropyran-2-yl) | 4.33 | 0.441 ± 0.156 (n = 9) | 0.178 ± 0.0436 | |
| 103 | CH₂CH₂CH₂OEt | 4.09 | 0.451 ± 0.416 (n = 6) | 0.0391 | |
| 104 | CH(Me)-(2-pyrimidinyl) | 3.36 | 0.453 ± 0.238 (n = 6) | 0.117 ± 0.0339 | |

TABLE 1-continued

SAR study of the TBNs at N-2

| Compound | R² | ClogP | 3D7 Mean EC$_{50}$ (μM) | K1 EC$_{50}$ (μM) | BJ EC$_{50}$ (μM) (cytotoxicity) |
|---|---|---|---|---|---|
| 105 | CH₂-(2-pyridyl) | 4.01 | 0.456 ± 0.0964 (n = 2) | 0.129 | |
| 106 | CH₂-(3-pyridyl) | 4.01 | 0.475 ± 0.163 (n = 6) | 0.236 | |
| 107 | CH₂-(4-F-phenyl) | 5.65 | 0.569 ± 0.485 (n = 6) | 0.401 | |
| 108 | (CH₂)₃CF₃ | 4.62 | 0.665 ± 0.734 (n = 6) | 0.241 | |
| 109 | (CH₂)₂C(O)OMe | 3.84 | 0.673 ± 0.107 (n = 4) | 0.487 | >23.3 |
| 110 | (CH₂)₂C(O)NMe₂ | 3.26 | 0.888 ± 0.459 (n = 4) | 0.658 | >23.3 |
| 111 | CH₂-(4-pyridyl) | 4.01 | 0.983 ± 0.133 (n = 6) | 0.647 | |
| 112 | CH₂-(2-Me-thiazol-4-yl) | 4.35 | 1.03 ± 0.549 (n = 3) | 0.641 | |
| 113 | (CH₂)₂CN | 3.27 | 1.62 ± 1.25 (n = 4) | 2.05 ± 0.256 | >23.3 |
| 87 | | 5.2 | 1.67 ± 0.8 (n = 6) | | >23.3 |

TABLE 1-continued
SAR study of the TBNs at N-2
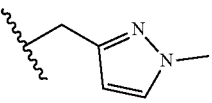 [SMILES: *Cc1ccn(C)n1]
| Compound | R² | ClogP | 3D7 Mean EC$_{50}$ (μM) | K1 EC$_{50}$ (μM) | BJ EC$_{50}$ (μM) (cytotoxicity) |
|---|---|---|---|---|---|
| 114 | 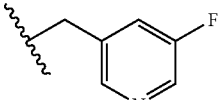 | 3.5 | 1.89 ± 0.817 (n = 3) | | |
| 115 | 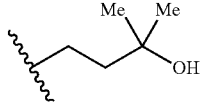 [SMILES: *CCC(C)(C)O] | 4.24 | 1.96 ± 2.34 (n = 3) | | |
| 116 | 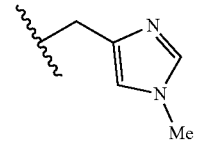 [SMILES: *Cc1cn(C)cn1] | 3.87 | 2.01 ± 0.277 (n = 6) | 1.44 ± 0.337 | |
| 117 | 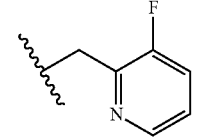 [SMILES: *Cc1ncccc1F] | 3.35 | 2.4 ± 1.39 (n = 3) | | |
| 118 | 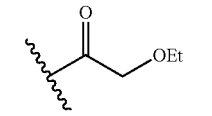 [SMILES: *C(=O)COCC] | 4.23 | 3.41 ± 2.9 (n = 3) | | |
| 119 | 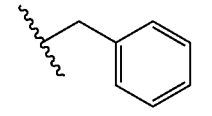 [SMILES: *Cc1ccccc1] | 2.97 | 3.49 ± 0.831 (n = 3) | | |
| 66 | 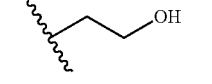 [SMILES: *CCO] | 5.51 | >3.49 ± 6.31 (n = 7) | 0.279 | |
| 120 | | 2.94 | 3.84 ± 2.08 (n = 9) | 2.2 ± 0.268 | |

TABLE 1-continued
SAR study of the TBNs at N-2
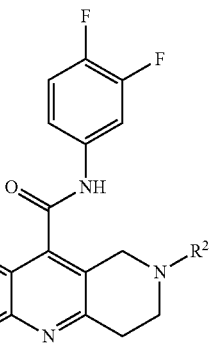
| Compound | R² | ClogP | 3D7 Mean EC₅₀ (μM) | K1 EC₅₀ (μM) | BJ EC₅₀ (μM) (cytotoxicity) |
|---|---|---|---|---|---|
| 121 | 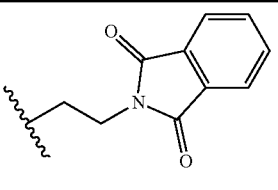 | 4.83 | 3.95 ± 1.07 (n = 4) | | |
| 122 | 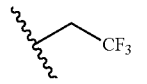 | 3.16 | 6.81 ± 2.54 (n = 9) | 4.64 ± 1.55 | |
| 123 | 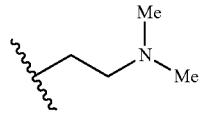 [SMILES: *CCN(C)C] | 4.53 | 7.69 ± 8.61 (n = 3) | | |
| 124 | 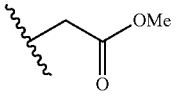 [SMILES: *CC(=O)OC] | 3.89 | 8.54 ± 1.84 (n = 6) | >19.2 | |
| 125 | 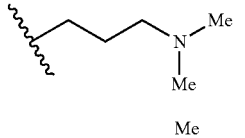 | 3.64 | 9.11 ± 7.61 (n = 3) | | |
| 126 | 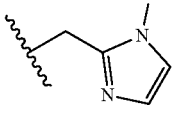 | 4.06 | 9.46 ± 2.17 (n = 6) | >19.2 | |
| 127 |  | 3.35 | 10.1 ± 6.39 (n = 3) | | |
| 88 | H | 3.07 | 10.3 ± 10.2 (n = 6) | | |
| 128 | 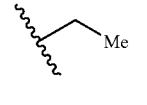 | 4.05 | >12.2 (n = 6) | | |
| 129 | 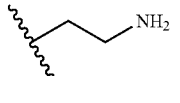 | 3.02 | 14.5 ± 4.73 (n = 9) | 9.46 ± 0.982 | |

TABLE 1-continued

SAR study of the TBNs at N-2

| Compound | R² | ClogP | 3D7 Mean EC$_{50}$ (μM) | K1 EC$_{50}$ (μM) | BJ EC$_{50}$ (μM) (cytotoxicity) |
| --- | --- | --- | --- | --- | --- |
| 130 | (propyl methyl sulfone) | 2.55 | > 14.7 (n = 6) | | |
| 131 | (propanoic acid) | 1.11 | > 19.2 (n = 6) | >19.2 | |

Based on the N-2 screen results, the N-phenethyl group was selected as a good substituent for further studies.

1.3 Synthesis of the Octohydrobenzonaphthyridine (OBN) Series

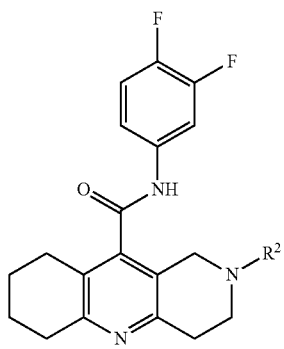

Additional efforts were given to modifications at the benzo-ring portion of the TBNs (site 2). A series of octohydrobenzonaphthyridne (OBN) analogues was prepared.

The synthesis of these compounds follows a synthetic pathway identical to that in Scheme 3 up through the protected amide, 87. As shown in Scheme 4, after amide 87 is isolated, a deprotection and hydrogenation occur concurrently in one step. In the presence of trifluoroacetic acid and platinum dioxide, TBN carboxamides selectively hydrogenate at the benzo ring at ambient pressure. The reaction must be closely monitored, or else over-reduction occurs. The deprotected OBN, 136, was isolated directly from this process and was alkylated by the agency of sodium triacetoxyborohydride in a manner parallel to the alkylation of 88. N-Ethyl OBN carboxamide 138 was produced via the amidation of hydrogenated acid 141, which had the N-ethyl substituent already installed. The OBN carboxamides and their potencies are listed in Table 2.

Scheme 4: Hydrogenation of TBN 87

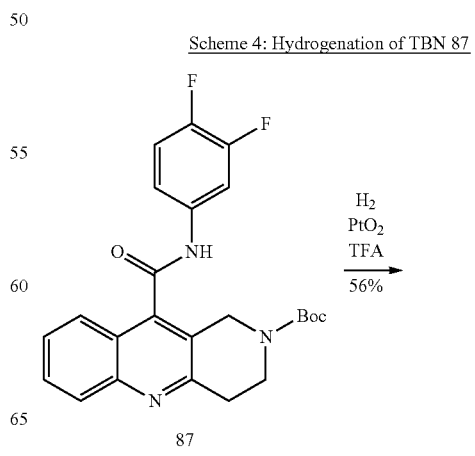

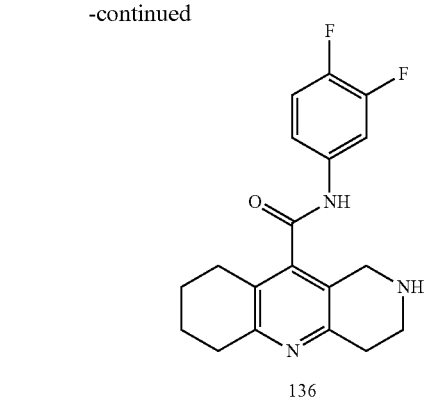

136

TABLE 2

Potencies of OBNs

| Compound | R[2] | ClogP | 3D7 Mean EC$_{50}$ (μM) | K1 EC$_{50}$ (μM) | 3D7 Mean EC$_{50}$ of the TBN (μM) |
|---|---|---|---|---|---|
| 137 | benzyl (CH$_2$Ph) | 5.69 | 0.0949 ± 0.0266 (n = 4) | 0.279 | >3.49 ± 6.31 (n = 7) |
| 138 | CH(Me)Et | 4.23 | 0.715 ± 0.29 (n = 6) | 0.64 | >12.2 (n = 6) |
| 139 | CH(Me)-pyrimidin-2-yl | 3.55 | 0.849 ± 0.52 (n = 10) | 0.266 ± 0.0462 | 0.453 ± 0.238 (n = 6) |
| 140 | CH(Me)-pyridin-2-yl | 4.51 | 1.50 ± 0.389 (n = 10) | 0.558 ± 0.123 | 0.0603 ± 0.0234 (n = 4) |

1.4 Development of a Divergent TBN Synthesis

Polar functionalities were introduced next in order to increase water solubility as shown in Scheme 5.

Acid 85 was esterified with iodomethane to form methyl ester 142. N-2 was liberated by one of two methods: either (1) an anhydrous mixture of trifluoroacetic acid and dichloromethane, or (2) anhydrous hydrochloric acid in dioxane were used to remove the N-Boc group. The newly formed secondary amine 143 was reductively alkylated with phenyl acetaldehyde in the presence of sodium triacetoxyborohydride, which produced 144. The ester was hydrolyzed with potassium hydroxide to give acid 145, which was be amidated to form the desired carboxanilide.

Scheme 5: TBN synthetic pathway via a methyl ester

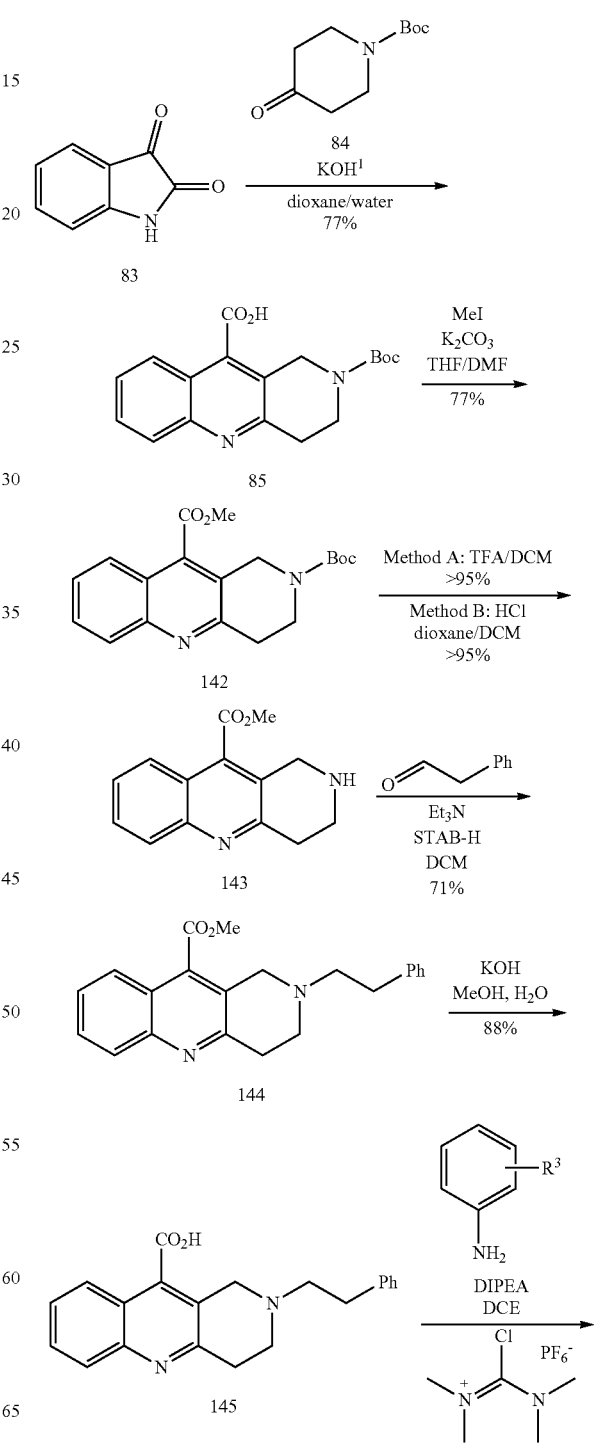

-continued

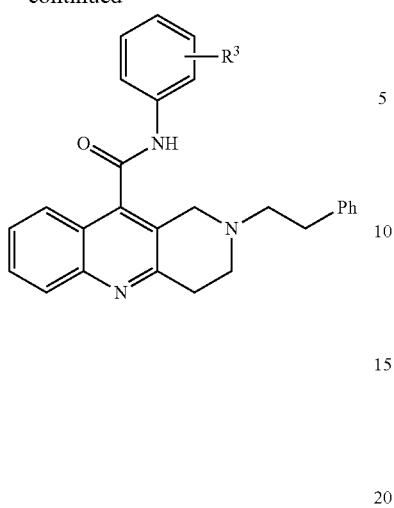

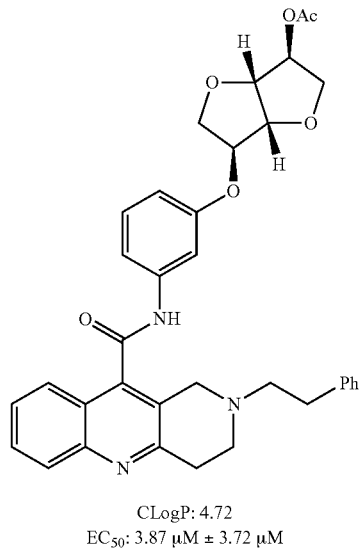

147

CLogP: 4.72
EC$_{50}$: 3.87 µM ± 3.72 µM

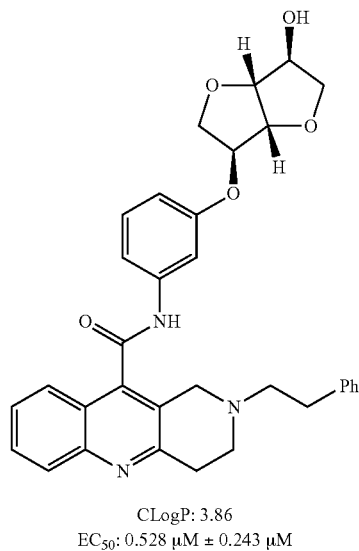

148

CLogP: 3.86
EC$_{50}$: 0.528 µM ± 0.243 µM

Initial attempts to amidate acid 145 were done with phosphorous oxychloride in manner similar to the amidation of acid 85. It was soon discovered that the phosphorous oxychloride conditions were specific to acid 85 and 3,4-difluoroaniline. The difficulty in amidating TBN acids can be explained by the steric bulk around the carboxylate; namely, the protons at C-1 and C-9 block the approach of nucleophiles towards the carbonyl carbon. A more general amidation procedure was discovered that overcomes the steric hindrance issue. N,N,N',N'-tetramethylchloroformamidinium hexafluorophosphate is a coupling reagent that activates sterically hindered acids (Beutner, G. L., et al. TCFH-NMI: Direct Access to N-Acyl Imidazoliums for Challenging Amide Bond Formations. *Org. Lett.* 2018, 20 (14), 4218-4222). This reagent effectively conjoined TBN acids with a variety of substituted anilines. Three TBN amides were synthesized via this route. The structures and EC$_{50}$ values are shown below.

1.5 Chlorine Scan and Structure-Activity Relationship Studies of the Carboxamide

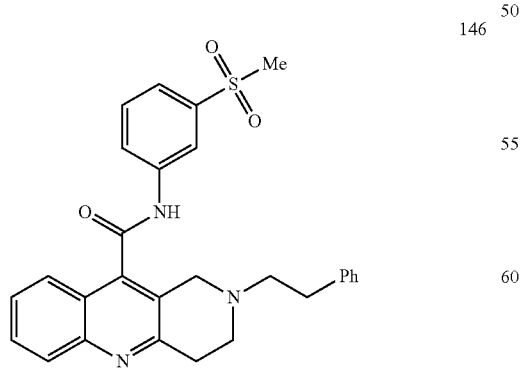

146

CLogP: 3.71
EC$_{50}$: 0.646 µM ± 0.00266 µM

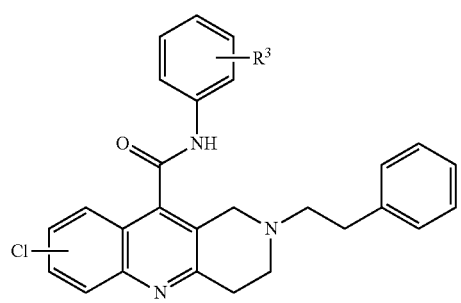

A series of chloro-substituted TBN analogues were developed.

The chlorine-containing analogues were synthesized through two separate routes. One route is analogous to Scheme 3 and features alkylation of the nitrogen as the final step (Scheme 6). By following this synthetic pathway, two compounds were produced that are chlorine substituted versions of TBN 91. The other route mimics the transformations of Scheme 5—the amide bond is formed in the last step (Scheme 7). Seven additional chloro-TBNs were synthesized by following this route.
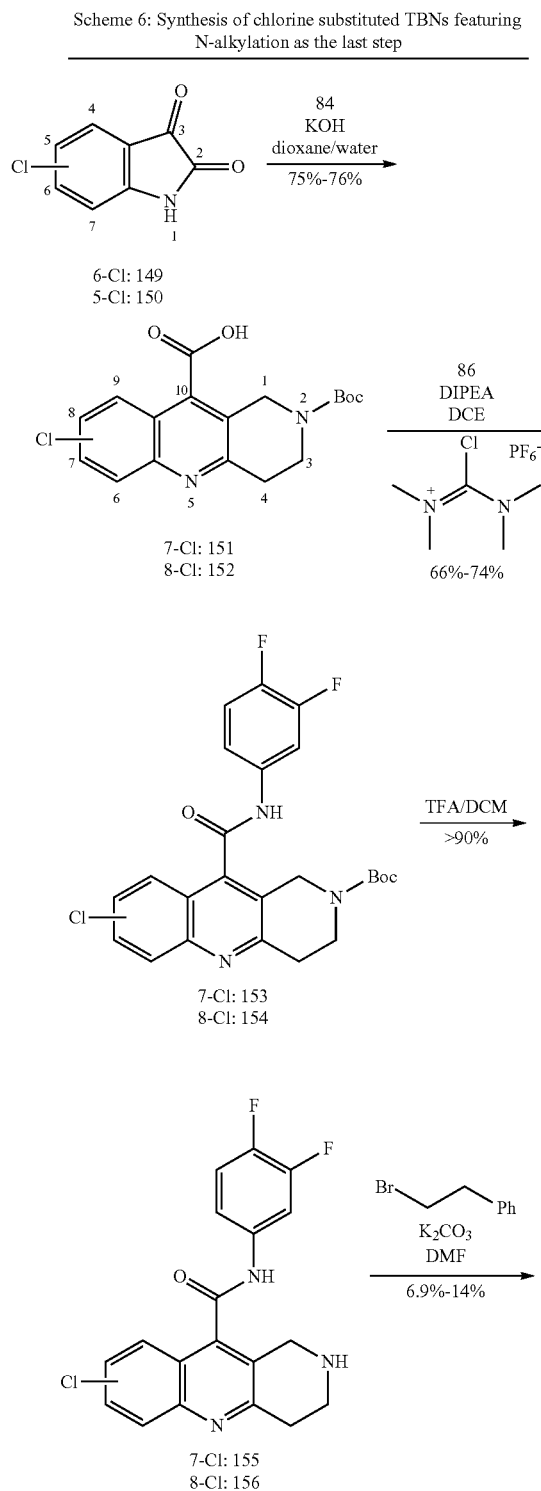
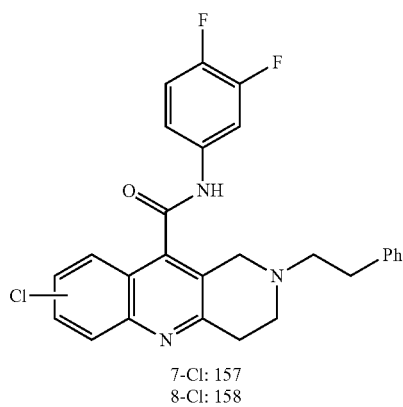
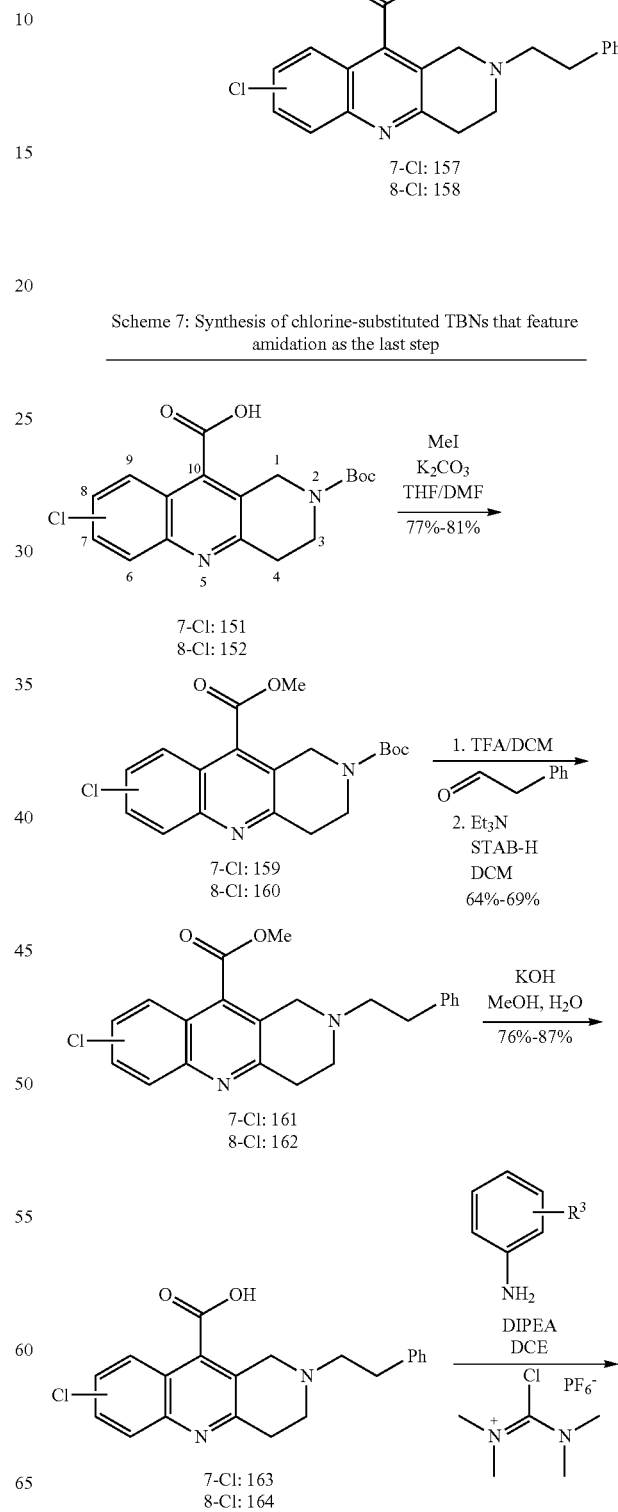

-continued

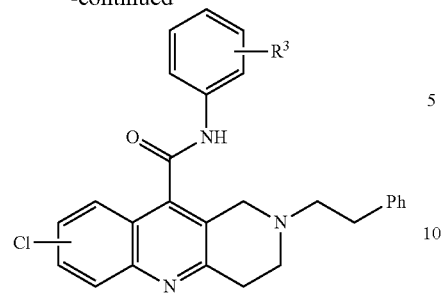

The EC$_{50}$ values of the chlorine substituted analogues are shown are Table 3.

TABLE 3

Potencies of chloro-TBNs with various carboxanilides

| Compound | R$^3$ | R$^2$ | ClogP | 3D7 Mean EC$_{50}$ (μM) | BJ EC$_{50}$ (μM) (cytotoxicity) |
|---|---|---|---|---|---|
| 165 | Cl (4-Cl phenyl) | 7-Cl | 6.67 | <0.00809 ± 0.007 (n = 3) | >24.0 (n = 4) |
| 166 | OMe, OMe (3,4-diOMe phenyl) | 7-Cl | 5.47 | <0.0132 ± 0.021 (n = 3) | >24.0 (n = 4) |
| 158 | F, F (3,4-diF phenyl) | 8-Cl | 6.19 | 0.0153 ± 0.00774 (n = 2) | — |
| 157 | F, F (3,4-diF phenyl) | 7-Cl | 6.19 | 0.0179 ± 0.0100 (n = 2) | — |

TABLE 3-continued

Potencies of chloro-TBNs with various carboxanilides

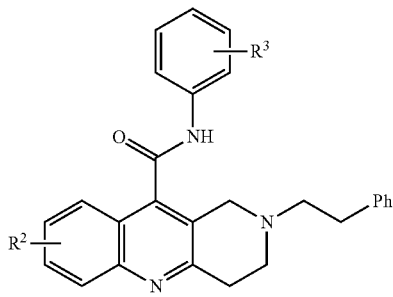

| Compound | R$^3$ | R$^2$ | ClogP | 3D7 Mean EC$_{50}$ (μM) | BJ EC$_{50}$ (μM) (cytotoxicity) |
|---|---|---|---|---|---|
| 167 | Cl (3-Cl phenyl) | 7-Cl | 6.67 | 0.0216 ± 0.012 (n = 3) | >24.0 (n = 4) |
| 168 | Cl (4-Cl phenyl) | 8-Cl | 6.67 | <0.0348 ± 0.059 (n = 3) | >24.0 (n = 4) |
| 169 | F, CN (4-F, 3-CN phenyl) | 7-Cl | 5.67 | 0.04 ± 0.032 (n = 3) | >24.0 (n = 4) |
| 170 | OMe, OMe (3,4-diOMe phenyl) | 8-Cl | 5.47 | 0.116 ± 0.025 (n = 3) | >24.0 (n = 4) |
| 171 | Br (4-Br phenyl) | 7-Cl | 6.82 | 0.37 ± 0.260 (n = 3) | >24.0 (n = 4) |

1.6 Pyrrolinone Derivatives

Scheme 8: Oxidation of TBNs to pyrrolinones via HgO

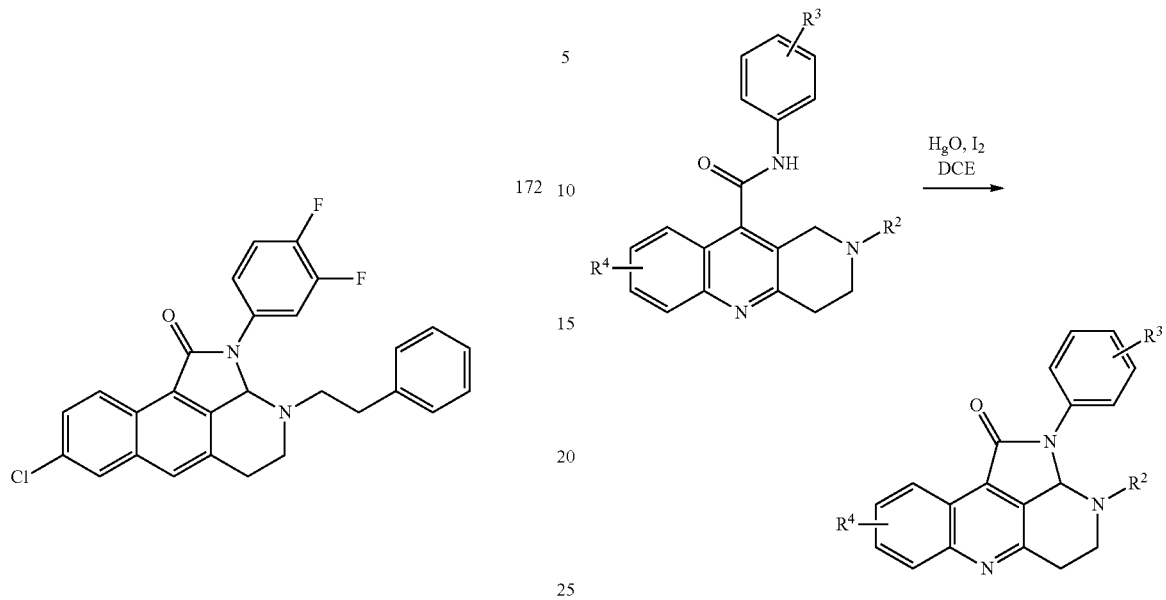

Pyrrolinones can be prepared by oxidation of TBNs as shown as Scheme 8. Thus, pyrrolinone derivative 172 was prepared by oxidation of 157. Compound 172 was assayed in the 3D7 strain of *P. falciparum*, and found to have an $EC_{50}$ of 7.1 nM±0.461 nM.

Additional pyrrolidinones were prepared by oxidation with mercuric oxide and iodine using the route of Scheme 8. The initial oxidation forms an iminium intermediate that acts as an electrophile toward the nearby amide nitrogen. The system undergoes cyclization to form the pyrrolinone. The measured $EC_{50}$ values are shown in Table 4.

TABLE 4

Potencies of TBN pyrrolinones

| Compound | $R^3$ | $R^4$ | $R^2$ | Clog P | 3D7 Mean $EC_{50}$ (μM) | BJ $EC_{50}$ (μM) (cytotoxicity) |
|---|---|---|---|---|---|---|
| 175 | 4-Br-phenyl | 7-Cl | CH₂CH₂Ph | 7.14 | <0.00192 (n = 3) | 15.2 ± 8.47 (n = 4) |
| 176 | 3-Cl-phenyl | 8-Cl | CH₂CH₂Ph | 6.99 | <0.00296 (n = 3) | >24.0 (n = 4) |

TABLE 4-continued
Potencies of TBN pyrrolinones
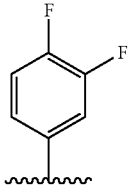 [SMILES: *c1ccc(F)c(F)c1]
| Compound | R³ | R⁴ | R² | Clog P | 3D7 Mean EC$_{50}$ (μM) | BJ EC$_{50}$ (μM) (cytotoxicity) |
|---|---|---|---|---|---|---|
| 177 | 3,4-diF-phenyl | H | CH₂Ph | 5.66 | 0.00328 ± 0.000533 (n = 2) | |
| 178 | 3,4-diOMe-phenyl | 7-Cl | CH₂CH₂Ph | 5.93 | 0.00446 ± 0.002 (n = 3) | 9.32 ± 6.69 (n = 4) |
| 179 | 4-Cl-phenyl | 7-Cl | CH₂CH₂Ph | 6.99 | 0.0059 ± 0.002 (n = 3) | 22.6 ± 0.373 (n = 4) |
| 172 | 3,4-diF-phenyl | 7-Cl | CH₂CH₂Ph | 6.49 | 0.0071 ± 0.000461 (n = 2) | |
| 180 | 3,4-diF-phenyl | H | CH(OEt)CH₂ | 4.38 | 0.0087 ± 0.001 (n = 3) | >24.0 (n = 4) |
| 181 | 4-Cl-phenyl | 8-Cl | CH₂CH₂Ph | 6.99 | 0.0126 ± 0.002 (n = 3) | >24.0 (n = 4) |

TABLE 4-continued

Potencies of TBN pyrrolinones

| Compound | R³ | R⁴ | R² | Clog P | 3D7 Mean EC$_{50}$ (μM) | BJ EC$_{50}$ (μM) (cytotoxicity) |
|---|---|---|---|---|---|---|
| 182 | 4-Br-phenyl | 8-Cl | -CH₂CH₂-Ph | 7.29 | 0.0396 ± 0.017 (n = 3) | >24.0 (n = 4) |
| 183 | 3-(hexahydrofuro[3,2-b]furan-OAc)oxy-phenyl | H | -CH₂CH₂-Ph | 5.07 | 0.0407 ± 0.012 (n = 3) | >24.0 (n = 4) |
| 184 | 4-F-3-CN-phenyl | 7-Cl | -CH₂CH₂-Ph | 5.85 | 0.0437 ± 0.021 (n = 3) | >24.0 (n = 4) |
| 185 | 3,4-diOMe-phenyl | 8-Cl | -CH₂CH₂-Ph | 5.94 | 0.049 ± 0.016 (n = 3) | >24.0 (n = 4) |

The potency of the pyrrolinone scaffold is highlighted by the activity of compound 183. The corresponding TBN (147) is among the least potent at 3.87 μM. Oxidation improves the potency of this structure nearly a hundred-fold to 40.7 nM.

Without wishing to be bound by any particular theory or mechanism of action, it can be contemplated that the unique aminal structure of the pyrrolinones imparts specific chemical behavior. Aminals are normally unstable functionalities that are prone to hydrolysis. To test the stability of the pyrrolidones, a solution of 177 in methanol-D₄ was treated dropwise with deuterated acetic acid. The experiment was followed by H-1 NMR analysis by observing the reduction of the peaks at 6.12 ppm and 8.73 ppm and the appearance of a peak at 9.42. Acidification causes the compound to begin conversion into another substance. Basifying the solution with sodium hydride returns the mixture to pyrrolinone.

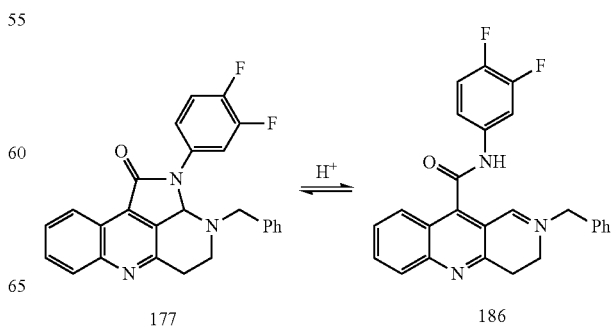

The Acid-Promoted Ring Opening of Pyrrolinone to Iminium

Compound 177 was acidified with hydrogen chloride in dioxane. The resulting hydrochloride salt fell out of solution and was isolated. The salt is identified as the TBN iminium ion (186). This suggests that the pyrrolinone is in an acid-mediated equilibrium with the ring-opened iminium ion. A likely mechanism for the interconversion includes the protonation of the carbonyl oxygen followed by the elimination of amido facilitated by the N–2 lone-pair electrons.

In summary, the TBNs and pyrrolinones are a promising series of compounds that were discovered to have antimalarial properties.

Additional compounds contemplated by the present invention are provided below. Preliminary data shows that a variety of groups are tolerated in different positions. Polar groups, such as triazoles and 3-cyano-4-fluorocarboxanilides (190), may improve water solubility and overall drug-likeness. The desbenzo analogue is oxidized (191) to determine whether the benzo-group is truly necessary for activity. The pyrrolinones were found to equilibrate with a ring-opened iminium form, which was isolated and characterized. Finally, it is possible that the active form is another metabolite that forms during the assay. Probable metabolites, such as the C-1 amide 192, are synthesized.

190

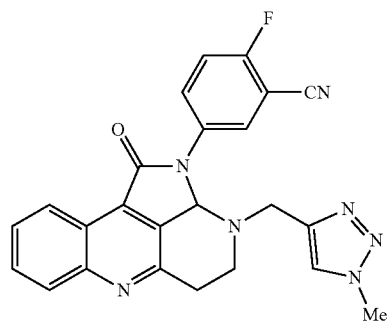

CLogP: 2.35

191

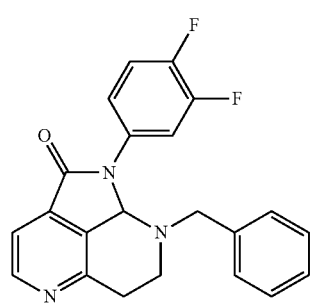

CLogP: 4.27

192

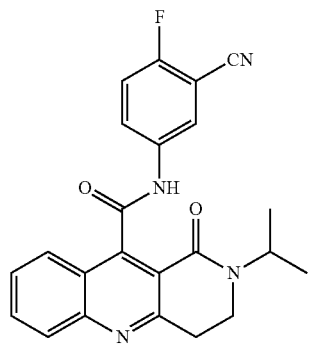

CLogP: 2.92

Additional novel compounds encompassed by the present invention are shown below:

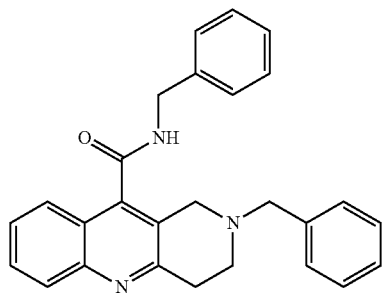

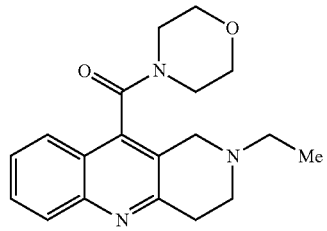

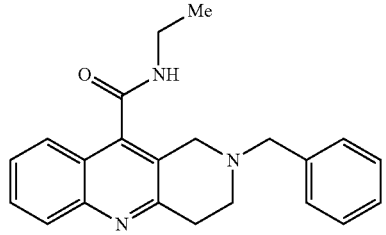

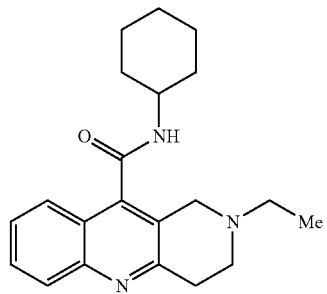

Example 2: Experimental

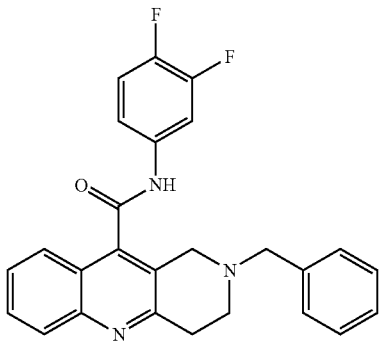

2-Benzyl-N-(3,4-difluorophenyl)-1,2,3,4-tetrahydrobenzo[b][1,6]naphthyridine-10-carboxamide (66)

A solution of acid 132 (500 mg, 1.57 mmol, 1.5 equiv) in acetonitrile (3.75 mL) was stirred at room temperature. 3,4-Difluoroaniline (180 µL, 1.0 mmol, 1 equiv) was added, followed by phosphorous oxychloride (120 µL, 1.3 mmol, 1.3 equiv), which caused the reaction to become cloudy. The suspension was heated at reflux for 16 h. The reaction was cooled to room temperature, concentrated, and then the residue was partitioned between ethyl acetate (50 mL) and saturated sodium bicarbonate (50 mL). The organic layer was collected, and the aqueous layer extracted once more with ethyl acetate (50 mL). The organic extracts were combined, dried over sodium sulfate, and concentrated to produce 66 as a yellow solid (267 mg, 58%), mp (decomposition): 222.4-231.3° C.: $^1$H NMR (500 MHz, DMSO-d$_6$) δ 10.95 (s, 1H), 7.97 (dd, J=8.9, 1.2 Hz, 1H), 7.80 (ddd, J=12.8, 7.4, 2.5 Hz, 1H), 7.76-7.71 (m, 2H), 7.57 (ddd, J=8.1, 6.9, 1.3 Hz, 1H), 7.45 (dt, J=10.5, 9.0 Hz, 1H), 7.36-7.31 (m, 3H), 7.28 (ddd, J=7.5, 6.7, 1.2 Hz, 2H), 7.24-7.20 (m, 1H), 3.79 (d, J=14.8 Hz, 1H), 3.75-3.66 (m, 3H), 3.15 (t, J=6.1 Hz, 2H), 2.87 (app q, J=6.3 Hz, 2H); $^{13}$C NMR (126 MHz, DMSO-d$_6$) δ 165.14, 157.08, 149.41 (dd, J=244.0, 14.0 Hz), 146.62, 146.40 (dd, J=242.8, 12.4 Hz), 139.64, 138.40, 135.57 (dd, J=9.0, 2.6 Hz), 129.93, 129.24, 128.87, 128.65, 127.48, 127.32, 124.90, 124.52, 122.88, 118.11 (d, J=18.3 Hz), 116.89, 109.61 (d, J=21.4 Hz), 61.70, 53.01, 50.09, 33.41; $^{19}$F NMR (470 MHz, DMSO-d$_6$) δ−137.00 (ddd, J=22.4, 12.6, 8.9 Hz), −143.38 (dddd, J=22.5, 11.2, 7.4, 4.0 Hz); ESI-MS [M+H]$^+$ m/z calcd for C$_{26}$H$_{22}$F$_2$N$_3$O$_1$, 430.17; found, 430.2

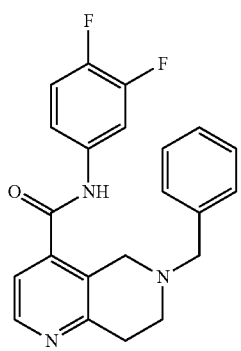 [SMILES: O=C(Nc1ccc(F)c(F)c1)c1ccnc2c1CN(Cc1ccccc1)CC2]

6-Benzyl-N-(3,4-difluorophenyl)-5,6,7,8-tetrahydro-1,6-naphthyridine-4-carboxamide (68)

A dry round bottom flask containing Na$_2$CO$_3$ (33 mg, 0.31 mmol, 1.5 equiv), XantPhos (24 mg, 0.042 mmol, 0.2 equiv), and Pd(AcO$_2$)$_2$ (9 mg, 0.042 mmol, 0.2 equiv) was placed under a carbon monoxide atmosphere. A solution of naphthyridine 75 (63 mg, 0.2 mmol, 1 equiv) in toluene (400 µL) was added via syringe, followed by 3,4-difluoroaniline (31 µL, 0.31 mmol, 1.5 equiv). The reaction mixture was heated to 90° C. and then was stirred for 16 h. The reaction mixture was cooled, diluted with 50 mL of diethyl ether, and then washed sequentially with water (50 mL) and brine (50 mL). The organic solution was dried over sodium sulfate, decanted, and concentrated to dryness. The residue was chromatographed (3% methanol and dichloromethane) to afford an off-white solid (17.6 mg, 23%), mp: 83.5-84.4° C.: $^1$H NMR (500 MHz, CDCl$_3$) δ 8.42 (d, 1H, J=4.91 Hz), 8.08 (s, 1H), 7.65 (ddd, 1H, J=11.25, 8.10, 1.85 Hz), 7.29-7.36 (m, 4H), 7.27 (tt, 1H, J=5.95, 1.70 Hz), 7.09-7.17 (m, 3H), 3.86 (s, 2H). 3.71 (s, 2H), 3.05 (t, 2H, J=6.03 Hz), 2.81 (t, 2H, J=6.01 Hz); $^{13}$C NMR (126 MHz, CDCl$_3$) δ 165.21, 156.96, 150.13 (dd, J=248.3, 13.4 Hz), 147.85, 147.47 (dd, J=246.2, 11.3 Hz), 140.80, 137.38, 133.85-133.50 (m), 129.15, 128.41, 127.85, 127.43, 117.80, 117.41 (d, J=18.4 Hz), 115.88, 110.08 (d, J=21.9 Hz), 62.37, 53.39, 49.37, 32.72, 29.69 (grease signal); $^{19}$F NMR (500 MHz, CDCl$_3$) δ−134.98—135.12 (m, 1F), −141.19 (dq, 1F, J=21.4, 7.1 Hz); ESI-MS [M+H]$^+$ m/z calcd for C$_{22}$H$_{20}$F$_2$N$_3$O, 241.13; found, 241.1.

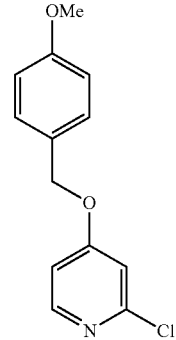 [SMILES: COc1ccc(COc2ccnc(Cl)c2)cc1]

2-chloro-4-((4-methoxybenzyl)oxy)pyridine (70)

A solution of 2-chloropyridin-4-ol (2 g, 15.44 mmol, 1 equiv) in acetone (50 mL) was stirred as room temperature. A portion of 1-chloromethyl-4-methoxybenzene (2.2 mL, 18 mmol, 1.2 equiv) was added followed by cesium carbonate (5.5 g, 17 mmol, 1.1 equiv). After 16 h of stirring the reaction was filtered, and the filtrate concentrated. The residue was chromatographed (4:1 hexane/ethyl acetate) to afford 70 as a white solid (2.048 g, 53%), mp: 74.7-76.7° C.: $^1$H NMR (500 MHz, CDCl$_3$) δ 8.19 (d, J=6.0 Hz, 1H), 7.33 (d, J=8.8 Hz, 1H), 6.93 (d, J=8.6 Hz, 1H), 6.90 (d, J=2.3 Hz, 1H), 6.80 (dd, J=5.8, 2.3 Hz, 1H), 5.03 (s, 2H), 3.83 (s, 3H); $^{13}$C NMR (126 MHz, CDCl$_3$) δ 162.49, 155.96, 148.59, 146.29, 125.49, 123.01, 110.26, 106.39, 106.29, 66.28, 51.38; ESI-MS [M+H]$^+$ m/z calcd for C$_{13}$H$_{13}$ClNO$_2$, 250.06; found, 249.9

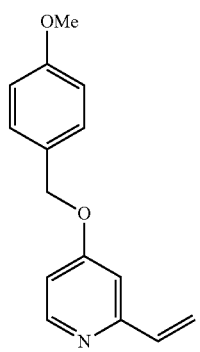 [SMILES: C=Cc1cc(OCc2ccc(OC)cc2)ccn1]

4-((4-Methoxybenzyl)oxy)-2-vinylpyridine (71)

A mixture of dioxane and water (9:1, 60 mL) was degassed by bubbling argon over a 10 min period. Pyridine 70 (1.5 g, 6 mmol, 1 equiv) was added, followed by potassium vinyltrifluoroborate (964 mg, 7.2 mmol, 1.2 equiv) and cesium carbonate (5.865 g, 18 mmol, 3 equiv), followed by Xphos Pd G2 (188 mg, 0.24 mmol, 0.04 equiv). The solution was heated at reflux for 16H, during which period the solution turned black in color. The reaction cooled to room temperature, and then was partitioned between dichloromethane (200 mL) and water (200 mL). The organic layer was collected, and the aqueous layer washed with additional dichloromethane (3×50 mL). The organic extracts were combined, dried over sodium sulfate, decanted, and concentrated. The residue was chromatographed (2:1 ethyl acetate/hexane) to produce 71 (927 mg, 64%); ESI-MS [M+H]$^+$ m/z calcd for $C_{15}H_{16}NO_2$, 242.11; found, 241.3.

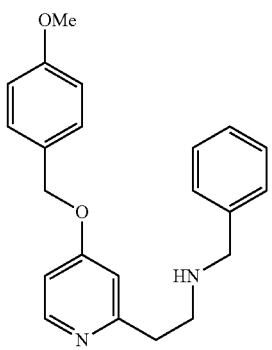 [SMILES: COc1ccc(COc2ccnc(CCNCc3ccccc3)c2)cc1]

N-Benzyl-2-(4-((4-methoxybenzyl)oxy)pyridin-2-yl)ethan-1-amine (72)

A solution of vinylpyridine 71 (275.5 mg, 1.14 mmol) in ethanol (5.7 mL) was stirred at room temperature. Benzylamine (250 μL, 2.28 mmol, 2 equiv) was added followed by acetic acid (65 μL, 1.14 mmol, 1 equiv), and then the reaction mixture was heated at reflux for 16 h. The reaction mixture was concentrated, and the residue was chromatographed (10%-20% methanol in dichloromethane) to produce a yellow oil that solidified on refrigeration (247 mg, 62%): $^1$H NMR (500 MHz, CD$_3$OD) δ 8.23 (d, J=5.8 Hz, 1H), 7.35 (d, J=8.8 Hz, 2H), 7.34-7.28 (m, 4H), 7.30-7.21 (m, 1H), 6.95-6.88 (m, 3H), 6.87 (dd, J=5.9, 2.5, Hz, 1H), 5.07 (s, 2H), 4.90-4.81 (Water signal), 3.80 (s, 2H), 3.78 (s, 3H), 2.94 (t, J=4.4 Hz, 4H); $^{13}$C NMR (126 MHz, CD$_3$OD) δ 166.06, 160.92, 159.82, 149.52, 138.34, 129.13, 128.22, 128.13, 127.89, 127.01, 113.57, 109.99, 108.78, 69.45, 54.29, 52.61, 36.52; ESI-MS [M+H]$^+$ m/z calcd for $C_{22}H_{25}N_2O_2$, 349.18; found, 349.1.

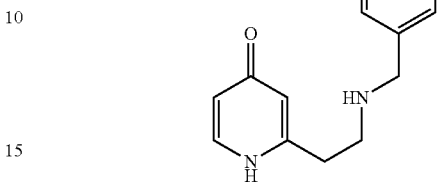

2-(2-(Benzylamino)ethyl)pyridin-4(1H)-one (73)

Method A: A solution of pyridine 72 (247 mg, 0.708 mmol, 1 equiv) in dichloromethane (1.5 mL) was stirred at room temperature. Trifluoroacetic acid was added (2.17 mL, 28.3 mmol, 40 equiv) and the reaction turned purple in color. After 45 min, the reaction was concentrated and the residue was chromatographed (3:2 ethyl acetate/hexane to 20% methanol in dichloromethane) producing the trifluoroacetate salt of 72 as a clear oil (253 mg, >95%): $^1$H NMR (500 MHz, MeOH-d4) $^1$H NMR (500 MHz, CD$_3$OD) δ 7.78 (d, J=7.0 Hz, 1H), 7.51-7.46 (m, 2H), 7.45-7.38 (m, 3H), 6.39 (dd, J=7.0, 2.5 Hz, 1H), 6.37 (d, J=2.5 Hz, 1H), 4.21 (s, 2H), 3.35 (t, J=7.7 Hz, 2H), 3.03 (t, J=7.7 Hz, 2H); $^{13}$C NMR (126 MHz, CD$_3$OD) δ 179.16, 161.76 (TFA C=O, q, J=34.3 Hz), 149.23, 139.74, 131.69, 129.51, 129.07, 128.79, 115.54, 114.95, 51.24, 45.58, 29.69 (the TFA CF$_3$ quartet was not observed); ESI-MS [M+H]$^+$ m/z calcd for $C_{14}H_{18}N_2O$, 229.13; found, 229.2.

Method B: A solution of octane thiol (683 μL, 3.93 mmol, 3.5 equiv) in DMF (9 mL) was prepared under an argon atmosphere. Sodium hydride (60% w/w, 170 mg, 4.25 mmol, 3.8 equiv) was added, causing the evolution of hydrogen gas. When bubbling stopped, pyridine 79 (273 mg, 1.12 mmol, 1 equiv) was added as a solution in DMF (2 mL), and the reaction mixture was heated at 130° C. for 20 min. The reaction was cooled to room temperature, quenched with water (10 mL), and then filtered. The filtrate was concentrated to a yellow oil that was taken to the next step without further purification; ESI-MS [M+H]$^+$ m/z calcd for $C_{14}H_{18}N_2O$, 229.13; found, 229.2.

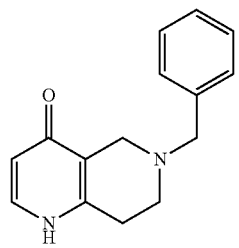 [SMILES: O=c1cc[nH]c2c1CN(Cc1ccccc1)CC2]

6-Benzyl-5,6,7,8-tetrahydro-1,6-naphthyridin-4(1H)-one (74)

A solution of pyridinone 73 (253 mg, 1.1 mmol, 1 equiv) in methanol (7.3 mL) was stirred at room temperature.

Formalin (37% w/w) was added (124 μL, 1.7 mmol, 1.5 equiv) and the solution was heated at reflux for 18 h. The reaction mixture was concentrated and the residue was chromatographed (10%-15% methanol in dichloromethane) to give the products as a hygroscopic white solid (230 mg, 87%): $^1$H NMR (500 MHz, MeOH-d4) δ 7.69 (d, 1H, J=7.19 Hz), 7.43-7.46 (m, 2H), 7.32-7.33 (m, 3H), 6.33 (d, 1H, J=7.18 Hz), 4.00 (s, 2H), 3.67 (s, 2H), 3.06 (t, 2H, J=6.07 Hz), 2.90 (t, 2H, J=5.95 Hz); $^{13}$C NMR (126 MHz, CD$_3$OD) δ 177.33, 143.99, 137.21, 134.31, 129.71, 128.38, 128.08, 113.73, 109.99, 61.23, 48.56, 47.93, 25.37; ESI-MS [M+H]$^+$ m/z calcd for $C_{15}H_{17}N_2O$, 241.13; found, 241.1.

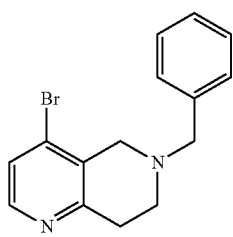 [SMILES: Brc1ccnc2c1CN(Cc1ccccc1)CC2]

6-Benzyl-4-bromo-5,6,7,8-tetrahydro-1,6-naphthyridine (75)

A suspension of naphthyridinone 74 (72 mg, 0.30 mmol, 1 equiv) in DMF (2.8 mL) was stirred under an argon atmosphere. Phosphorous oxybromide (129 mg, 0.45 mmol, 1.5 equiv) was added. The suspension cleared and the solution turned red in color. After a 30 min period, the reaction was checked for completion by TLC (1:1 ethyl acetate/hexane). If starting material remained, an additional portion of phosphorous oxybromide was added (1.5 equiv) and the reaction stirred for an additional 30 min. Upon completion, the reaction mixture was quenched with saturated aq. potassium carbonate (20 mL) and washed twice with ethyl acetate (20 mL). The combined organic extract was dried over sodium sulfate, decanted, and concentrated to a dark oil. The crude product was of sufficient purity to bring to the next step (63.2 mg, 69%): $^1$H NMR (500 MHz, CDCl$_3$) δ 8.18 (d, 1H, J=5.27 Hz), 7.33-7.41 (m, 4H), 7.30 (d, 1H, J=5.28 Hz), 7.29 (tt, 1H, J=7.00, 2.40 Hz), 3.76 (s, 2H), 3.67 (s, 2H), 3.03 (t, 2H, J=5.90 Hz), 2.80 (t, 2H, J=5.93 Hz); $^{13}$C NMR (126 MHz, CDCl$_3$) δ 157.21, 147.56, 137.76, 133.21, 130.51, 128.99, 128.41, 127.33, 125.12, 62.23, 55.65, 49.52, 32.81; ESI-MS [M+H]$^+$ m/z calcd for $C_{15}H_{16}BrN_2$, 303.04; found, 303.1.

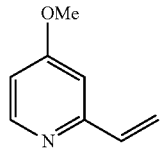

4-Methoxy-2-vinylpyridine (78)

A mixture of dioxane and water (9:1, 39 mL) was degassed by bubbling argon for 10 min. 2-Chloro-4-methoxypyridine (559 mg, 3.9 mmol, 1 equiv) was added, followed by potassium vinyltrifluoroborate (627 mg, 4.7 mmol, 1.2 equiv), cesium carbonate (3.812 g, 11.7 mmol, 3 equiv), and then Xphos Pd G2 (122 mg, 0.156 mmol, 0.04 equiv). The solution was heated at reflux for 16 h; the solution turned black in color. The reaction was cooled, and then was partitioned between dichloromethane (200 mL) and water (200 mL). The organic layer was collected, and the aqueous layer washed with additional dichloromethane (3×50 mL). The combined organic extract was dried over sodium sulfate, decanted, and concentrated. The residue was chromatographed (2:1 ethyl acetate/hexane) to produce 78 as a yellow oil (101 mg, 42%): $^1$H NMR (500 MHz, CDCl$_3$) δ 8.39 (d, 1H, J=5.69 Hz), 6.84 (d, 1H, J=2.45 Hz), 6.75, (dd, 1H, J=10.77, 17.43 Hz), 6.64 (dd, 1H, J=2.47, 5.68 Hz), 6.18 (dd, 1H, J=1.21, 17.46 Hz), 5.46 (dd, 1H, J=1.17, 10.74), 3.85 (s, 3H); ESI-MS [M+H]$^+$ m/z calcd for $C_8H_9NO$, 136.07; found, 136.0.

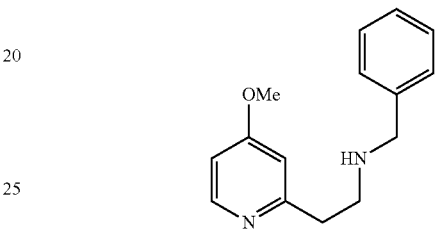

N-Benzyl-2-(4-methoxypyridin-2-yl)ethan-1-amine (79)

A solution of pyridine 78 (834 mg, 5.43 mmol) in ethanol (27 mL) was prepared at room temperature. Benzyl amine (890 μL, 8.16 mmol, 1.5 equiv) was added followed by acetic acid (311 μL, 5.43 mmol, 1 equiv). The reaction mixture was heated at reflux for 16 h. The reaction was cooled, concentrated, and then the residue was chromatographed twice (10% methanol in dichloromethane) to produce 79 as a clear oil (423.6 mg, 32%): $^1$H NMR (500 MHz, CDCl$_3$) δ 7.25-7.36 (m, 1H), 7.25-7.36 (m, 5H), 6.65-6.69 (m, 2H), 6.32-6.57 (br s, 1.5H), 3.95 (s, 2H), 3.81 (s, 3H), 3.13, (t, 2H, J=6.45 Hz), 3.02 (t, 2H, J=6.47 Hz), 2.00 (acetic acid residue, s); ESI-MS [M+H]$^+$ m/z calcd for $C_{15}H_{19}N_2O$, 243.14; found, 243.4.

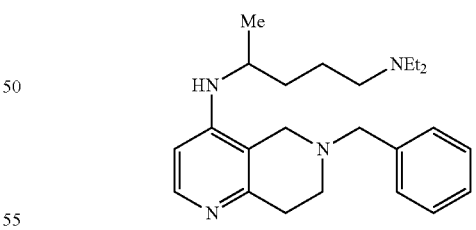

N$^4$-(6-Benzyl-5,6,7,8-tetrahydro-1,6-naphthyridin-4-yl)-N$^1$,N$^1$-diethylpentane-1,4-diamine (80)

Freshly prepared bromopyridine 75 (50 mg, 0.165 mmol, 1 equiv) was put under an argon atmosphere. Potassium phosphate (88 mg, 0.413 mmol, 2.5 equiv) was added, followed by Pd(OAc)$_2$ (1.5 mg, 0.0066 mmol, 0.04 equiv), DPEphos (7.1 mg, 0.0132 mmol, 0.08 equiv), 2-amino-5-diethylaminopentane (48 μL, 0.248 mmol, 1.5 equiv) and dioxane (1 mL). The reaction mixture was heated at 85° C.

for 16 h. The reaction mixture was cooled and concentrated and the residue was chromatographed (1:1 hexane/ethyl acetate to 6:1.6:0.3 ethyl acetate/methanol/30% ammonium hydroxide) to produce 80 as a yellow solid (13 mg, 20%): $^1$H NMR (400 MHz, CDCl$_3$) δ 8.09 (d, J=5.8 Hz, 1H), 7.41-7.27 (m, 5H), 6.35 (d, J=5.9 Hz, 1H), 3.75 (s, 2H), 3.61-3.52 (m, 1H), 3.35 (s, 2H), 2.94 (t, J=5.9 Hz, 2H), 2.76 (t, J=5.8 Hz, 2H), 2.57 (q, J=7.2 Hz, 4H), 2.47 (t, J=6.9 Hz, 2H), 1.56 (m, 5H), 1.20 (d, J=6.3 Hz, 3H), 1.04 (t, J=7.2 Hz, 6H); ESI-MS [M+H]$^+$ m/z calcd for C$_{24}$H$_{37}$CN$_4$, 381.29; found, 381.4.

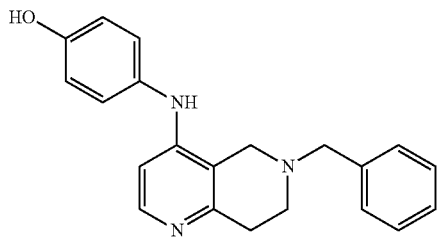 [SMILES: Oc1ccc(Nc2ccnc3c2CN(Cc2ccccc2)CC3)cc1]

4-((6-Benzyl-5,6,7,8-tetrahydro-1,6-naphthyridin-4-yl)amino)phenol (81)

Freshly prepared bromopyridine 75 (50 mg, 0.165 mmol, 1 equiv) was put under an argon atmosphere. Potassium phosphate (88 mg, 0.413 mmol, 2.5 equiv) was added, followed by Pd(OAc)$_2$ (1.5 mg, 0.0066 mmol, 0.04 equiv), DPEphos (7.1 mg, 0.0132 mmol, 0.08 equiv), 4-aminophenol (27 mg, 0.248 mmol, 1.5 equiv) and dioxane (1 mL). The reaction mixture was heated to 85° C. for 16 h. The reaction mixture was cooled and concentrated and the residue was chromatographed (30% methanol in dichloromethane) to produce 81 as a dark red oil (7.1 mg, 13%): $^1$H NMR (500 MHz, CDCl$_3$) δ 7.97 (d, J=5.9 Hz, 1H), 7.39 (br d, J=7.0 Hz, 2H), 7.34 (br t, J=7.0 Hz, 2H), 7.28 (app tt, J=7.3, 1.5 Hz, 1H), 6.95 (d, J=9.1 Hz, 2H), 6.83 (d, J=9.1 Hz, 2H), 6.48 (d, J=5.9 Hz, 1H), 5.52 (br s, 1H), 3.90 (br s, 6H), 3.78 (s, 2H), 3.48 (s, 4H, overlapped with methanol), 3.03 (t, J=5.9 Hz, 2H), 2.84 (t, J=5.8 Hz, 2H); ESI-MS [M+H]$^+$ m/z calcd for C$_{15}$H$_{21}$N$_2$O$_2$, 261.15; found, 261.4.

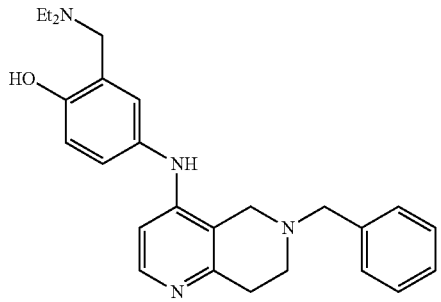

4-((6-Benzyl-5,6,7,8-tetrahydro-1,6-naphthyridin-4-yl)amino)-2-((diethylamino)methyl)phenol (82)

A solution of 81 (50 mg, 0.15 mmol, 1 equiv) in ethanol (300 μL) was stirred at room temperature. Diethylamine (21 μl, 0.2 mmol, 1.4 equiv) and paraformaldehyde (6 mg, 0.15 mmol, 1 equiv) were dissolved in ethanol (200 μL), and the solution was added via syringe. The reaction mixture was heated at reflux for 16H, cooled, concentrated, and then diluted with methanol. A solution 1N HCl was added until the solution reached a pH of 1 (pH paper). The reaction was concentrated, and then acetone was added, creating a black suspension. The suspension was filtered, and the filtrate was concentrated. The residue was chromatographed (15% methanol in dichloromethane) to produce an off-white solid (2.3 mg, 3.6%): $^1$H NMR (500 MHz, CD$_3$OD) δ 7.89 (d, J=6.5 Hz, 1H), 7.44-7.41 (m, 2H), 7.35 (app t, J=7.3 Hz, 2H), 7.29 (app tt, J=7.3, 1.4 Hz, 1H), 7.08 (dd, J=8.5, 2.6 Hz, 1H), 7.06 (d, J=2.6 Hz, 1H), 6.86 (d, J=8.4 Hz, 1H), 6.59 (d, J=6.5 Hz, 1H), 3.99 (s, 2H), 3.83 (s, 2H), 3.60 (s, 2H), 2.93 (t, J=5.8 Hz, 2H), 2.91-2.81 (m, 6H), 1.21 (t, J=7.2 Hz, 6H); ESI-MS [M+H]$^+$ m/z calcd for C$_{26}$H$_{33}$N$_4$O, 417.26; found, 417.2. The base peak is 209.4, which corresponds to [(M+2H)/2]$^{2+}$.

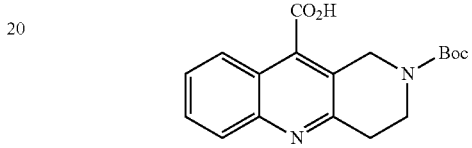

2-(tert-Butoxycarbonyl)-1,2,3,4-tetrahydrobenzo[b][1,6]naphthyridine-10-carboxylic acid (85)

A solution of isatin (1.47 g, 10 mmol) and potassium hydroxide (5.6 g, 100 mmol, 10 equiv) in 50% aq dioxane (20 mL) was stirred for 20 min at room temperature. A solution of 1-Boc-4-piperidone in 50% aq dioxane (2.40 g, 12 mmol, 1.2 M, 1.2 equiv.) was added, and the reaction mixture was heated at reflux for 16 h. The heterogeneous mixture was cooled, diluted with water (60 mL), and then extracted sequentially with toluene (30 mL) and ether (30 mL). The aqueous layer was collected and acidified dropwise with 37% aq hydrochloric acid until a thick yellow precipitate formed (pH≈2). The suspension was filtered, and the cake was washed with water. The resulting solid was dried in vacuo to afford 85 as an off-white solid (2.53 g, 77%), mp: 189.6° C. (decomposition): $^1$H NMR (500 MHz, DMSO-d6) δ 7.97 (dd, 1H, J=8.5, 0.5 Hz), 7.85 (dd, 1H, J=8.4, 0.6 Hz), 7.76 (ddd, 1H, J=8.3, 6.9, 1.4 Hz), 7.62 (ddd, 1H, J=8.3, 6.9, 1.3 Hz), 4.73 (s, 2H), 3.74 (t, 2H, J=6.2 Hz), 3.13 (t, 2H, J=6.2 Hz), 1.41 (s, 9H); $^{13}$C NMR (126 MHz, DMSO-d6) δ 168.2, 156.9, 146.5, 130.2, 129.0, 127.6, 125.1, 123.6, 122.4, 79.9, 28.5; ESI-MS [M+H]$^+$ calcd for C$_{18}$H$_{20}$N$_2$O$_4$, 329.14; found, 329.1.

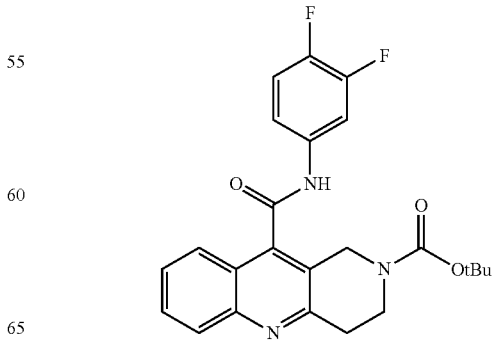

tert-Butyl 10-((3,4-difluorophenyl)carbamoyl)-3,4-dihydrobenzo[b][1,6]naphthyridine-2(1H)-carboxylate (87)

A suspension of acid 85 (53 mg, 0.16 mmol, 1 equiv) in acetonitrile (540 µL) was stirred at room temperature. 3,4-Difluoroaniline (24 µL, 0.24 mmol, 1.5 equiv) was added, followed by phosphorous oxychloride (17 µL, 0.18 mmol, 1.1 equiv). After 30 min, saturated sodium bicarbonate was added (10 mL), which cleared the suspension. The aqueous solution was extracted with ethyl acetate (10 mL). The organic layer was collected, dried over sodium sulfate, decanted, and concentrated. The residue was chromatographed (2:1 ethyl acetate/hexane) to give 87 as a white solid (16 mg, 23%), mp: 216.4-217.2° C.: $^1$H NMR (500 MHz, CDCl$_3$) δ 9.03 (br s, 1H), 8.03-7.86 (m, 2.6H), 7.72 (t, J=7.7 Hz, 1H), 7.60-7.52 (m, 1H), 7.45 (d, J=10.3 Hz, 1H), 7.20 (app q, J=9.3 Hz, 1H), 4.72 (br s, 2H), 3.73 (br s, 2H), 3.12 (s, 2H), 1.40 (s, 9H); $^{19}$F NMR (470 MHz, CDCl$_3$) δ −135.09, −141.48; ESI-MS [M+H]$^+$ m/z calcd for C$_{24}$H$_{24}$F$_2$N$_3$O$_3$, 440.17; found, 440.0 taken to the next step despite some residual trifluoroacetic acid and 9% 3,4-difluoroaniline: $^1$H NMR (500 MHz, MeOH-d4) δ 7.99 (d, 1H, J=8.2 Hz), 7.87 (ddd, 1H, J=12.5, 7.3, 2.6 Hz), 7.84 (dd, 1H, J=8.6, 0.7 Hz), 7.75 (ddd, 1H, J=8.4, 6.9, 1.4 Hz), 7.59 (ddd, 1H, J=8.2, 6.9, 1.2 Hz), 7.38 (dddd, 1H, J=8.9, 4.0, 2.6, 1.7 Hz), 7.25 (dt, 1H, J=10.3, 8.9 Hz), 4.19 (d, 2H, J=25.3 Hz), 3.33-3.29 (m, 4H, includes residual MeOH peak), 3.21 (t, 2H, J=6.1 Hz); $^{13}$C NMR (126 MHz, MeOH-d4) δ 165.54, 156.53, 146.19, 140.04, 129.79, 127.46, 127.08, 124.65, 124.22, 123.16, 117.14 (d, J=17.9 Hz), 115.95 (dd, J=6.1, 3.6 Hz), 109.43 (d, J=22.0 Hz), 44.81, 42.71, 32.26; $^{13}$C NMR (126 MHz, DMSO-d$_6$) δ 165.25, 157.52, 149.46 (dd, J=243.9, 13.3 Hz), 146.50, 146.35 (dd, J=242.4, 12.5 Hz), 139.26, 135.81 (dd, J=9.0, 2.9 Hz), 129.80, 128.88, 127.27, 125.48, 124.88, 123.08, 118.16 (d, J=17.9 Hz), 116.66 (dd, J=6.3, 3.4 Hz), 109.41 (d, J=21.5 Hz), 45.56, 43.39, 33.45; $^{19}$F NMR (500 MHz, MeOH-d4) δ−76.76 (s, trifluoroacetic acid), −137.94 (dddd, J=20.5, 12.2, 8.5, 2.6 Hz), −144.05 (dddd, J=22.7, 11.4, 7.8, 4.2 Hz); ESI-MS [M+H]$^+$ calcd for C$_{19}$H$_{15}$F$_2$N$_3$O, 340.12; found, 340.1.

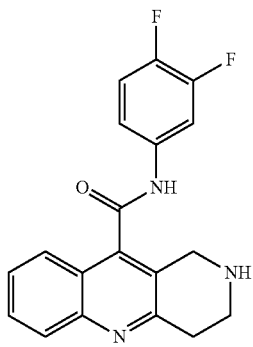 [SMILES: O=C(Nc1ccc(F)c(F)c1)c1c2c(nc3ccccc13)CCNC2]

N-(3,4-Difluorophenyl)-1,2,3,4-tetrahydrobenzo[b][1,6]naphthyridine-10-carboxamide (88)

3,4-Difluoroaniline (200 µL, 2.0 mmol, 1.6 equiv) was added to a suspension of carboxylic acid 85 (403 mg, 1.2 mmol, 1 equiv) in acetonitrile (4 mL). The mixture was cooled to 0° C. and then treated with phosphorus oxychloride (137 µL, 1.5 mmol, 1.2 equiv). After 30 min, the suspension was filtered, and the resulting solid was rinsed with acetonitrile. Sodium hydroxide (30 mL of a 1N solution) was added to the solid, and the resulting solution was extracted three times with 30 mL of dichloromethane. The combined organic layer was dried over anhydrous sodium sulfate, decanted, and then concentrated. A solution of the residue in dichloromethane (2 mL) was treated with trifluoroacetic acid (1 mL), and the solution was stirred at room temperature. After 1H, the reaction was concentrated, and the residue dissolved in 20 mL of 1N sodium hydroxide. The aqueous solution was exhaustively extracted, first with 20 mL of 25% methanol in dichloromethane, and then twice more with 20 mL of dichloromethane. This extraction procedure was repeated approximately five times until the product was no longer visible in the aqueous layer according to TLC analysis. The combined organic extract was dried over anhydrous sodium sulfate, decanted, and concentrated. The resulting white solid was triturated with 50% ethyl ether in hexanes, and then dried in vacuo to afford the crude product as a white solid (140 mg, 33%). The product was

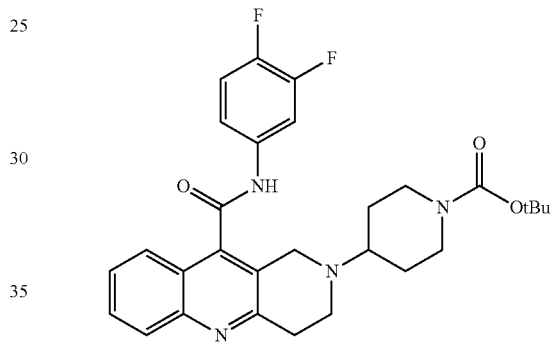

tert-Butyl 4-(10-((3,4-difluorophenyl)carbamoyl)-3,4-dihydrobenzo[b][1,6]naphthyridin-2(1H)-yl)piperidine-1-carboxylate (89)

A solution of amine 88 (31 mg, 0.091 mmol, 1 equiv) in dichloroethane (600 µL) was stirred at room temperature. tert-butyl 4-oxopiperidine-1-carboxylate (22 mg, 0.11 mmol, 1.2 equiv) was added, followed by acetic acid (5.2 µL, 0.091 mmol, 1 equiv). The reaction was stirred for 1H, then sodium triacetoxyborohydride (39 mg, 0.18 mmol, 2 equiv) was added. After 16H, the reaction was quenched with saturated sodium bicarbonate and the mixture extracted with ethyl acetate. The organic extract was collected, dried over sodium sulfate, decanted, and concentrated. The residue was chromatographed twice (5% methanol in dichloromethane) to produce 89 with 5% oxidized impurity (16.8 mg, 35%), mp: 213.0-215.0° C.: 1H NMR (500 MHz, CD$_3$OD) δ 8.00 (d, J=8.5 Hz, 1H), 7.90 (ddd, J=12.5, 7.3, 2.6 Hz, 1H), 7.84 (ddd, J=8.4, 1.4, 0.7 Hz, 1H), 7.77 (ddd, J=8.4, 6.9, 1.4 Hz, 1H), 7.61 (ddd, J=8.2, 6.9, 1.2 Hz, 1H), 7.40 (dddd, J=8.9, 4.0, 2.6, 1.6 Hz, 1H), 7.30 (dt, J=10.3, 8.9 Hz, 1H), 4.17-4.04 (m, 3H), 3.98 (d, J=14.7 Hz, 1H), 3.26 (t, J=6.1 Hz, 2H), 3.11 (t, J=6.1 Hz, 2H), 2.87-2.70 (m, 3H), 1.92 (d, J=12.1 Hz, 2H), 1.55-1.45 (m, 2H), 1.44 (s, 9H); $^1$H NMR (500 MHz, CDCl$_3$) δ 8.77 (s, 1H), 8.01 (ddd, J=11.9, 7.1, 2.6 Hz, 1H), 7.91 (d, J=8.4 Hz, 1H), 7.76 (d, J=8.6 Hz, 1H), 7.65 (ddd, J=8.4, 6.9, 1.4 Hz, 1H), 7.49 (ddd, J=8.3, 6.9, 1.1 Hz, 1H), 7.50-7.43 (m, 1H), 7.22 (dt, J=9.8, 8.7 Hz, 1H), 4.17 (br s, 2H), 3.87 (br s, 2H), 3.11 (t, J=6.0 Hz, 2H), 2.87 (t, J=5.9 Hz, 2H), 2.76-2.62 (m, 3H), 1.82 (d, J=11.8 Hz, 2H), 1.51-1.46 (m, 2H), 1.44 (s, 9H); ¹³C NMR (126 MHz, CDCl₃) δ 164.74, 156.83, 154.61, 150.28 (dd, J=248.2, 13.3 Hz), 147.79 (dd, J=246.6, 12.8 Hz), 146.53, 138.83, 134.22 (dd, J=8.8, 3.2 Hz), 129.91, 128.34, 127.32, 124.51, 124.15, 122.56, 117.63 (d, J=18.1 Hz), 115.48 (dd, J=6.0, 3.7 Hz), 109.72 (d, J=21.9 Hz), 79.73, 61.51, 49.17, 45.27, 43.07, 33.31, 28.40, 28.34; ¹⁹F NMR (470 MHz, CDCl₃) δ−134.72 (dt, J=21.4, 10.5 Hz), −141.07−−141.40 (m); ESI-MS [M+H]⁺ m/z calcd for $C_{29}H_{33}F_2N_4O_3$, 523.24; found, 523.1.

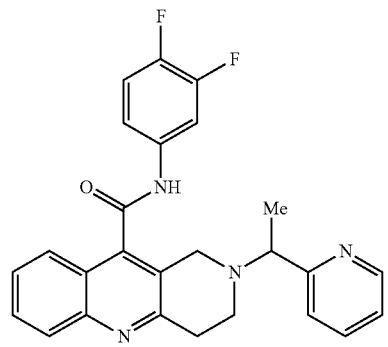

N-(3,4-Difluorophenyl)-2-(1-(pyridin-2-yl)ethyl)-1, 2,3,4-tetrahydrobenzo[b][1,6]naphthyridine-10-carboxamide (90)

A suspension of amine 88 (50 mg, 0.147 mmol) in dichloroethane (1.5 mL) was stirred under a nitrogen atmosphere. 2-Acetylpyridine (20 μL, 0.177 mmol, 1.2 equiv) was added followed by sodium triacetoxyborohydride (47 mg, 0.221 mmol, 1.5 equiv). The reaction stirred for 16H, then was heated to 70° C. for 3 h. An additional portion of sodium triacetoxyborohydride (1.5 equiv) was added before continuing to stir at 70° C. for 2.5 h. The reaction was cooled and stirred at room temperature for 16 h. Saturated sodium bicarbonate (10 mL) was added, and the resulting mixture extracted with dichloromethane (2×10 mL). The organic layers were combined and concentrated. The residue was chromatographed (2% methanol in 1:1 ethyl acetate/hexane) to produce 90 (17 mg, 26%): 1H NMR (500 MHz, CDCl₃) δ 8.88 (br s, 1H), 8.48 (ddd, J=4.9, 1.8, 0.9 Hz, 1H), 7.97 (ddd, J=8.5, 1.3, 0.7 Hz, 1H), 7.85 (ddd, J=11.7, 7.1, 2.5 Hz, 1H), 7.81 (ddd, J=8.4, 1.4, 0.6 Hz, 1H), 7.70-7.64 (m, 3H), 7.51 (ddd, J=8.2, 6.8, 1.2 Hz, 1H), 7.42 (dt, J=7.9, 1.1 Hz, 1H), 7.37-7.32 (m, 1H), 7.18 (dt, J=9.8, 8.8 Hz, 2H), 7.16-7.14 (m, 1H), 4.14 (d, J=15.0 Hz, 1H), 4.03 (q, J=6.8 Hz, 1H), 3.94 (d, J=15.3 Hz, 1H), 3.30-3.06 (m, 4H), 2.45 (br s, 3H), 1.59 (d, J=6.7 Hz, 3H). ¹⁹F NMR (470 MHz, CDCl₃) δ−135.10 (dt, J=21.3, 10.3 Hz), −141.26−−141.56 (m); ESI-MS [M+H]⁺ m/z calcd for $C_{26}H_{23}F_2N_4O$, 445.18; found, 444.8.

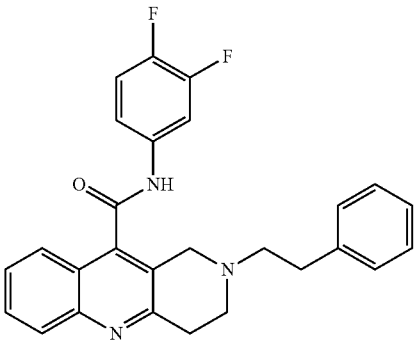 [SMILES: O=C(Nc1ccc(F)c(F)c1)c1c2c(nc3ccccc13)CCN(CCc1ccccc1)C2]

N-(3,4-Difluorophenyl)-2-phenethyl-1,2,3,4-tetrahydrobenzo[b][1,6]naphthyridine-10-carboxamide (91)

A solution of karstedt's catalyst (2% in xylenes, 7.3 μL, 0.05 equiv) in dioxane (450 μL) was stirred under a nitrogen atmosphere. In quick succession, phenylsilane (125 μL, 1 mmol, 8 equiv) was added, followed by secondary amine 88 (43 mg, 0.127 mmol, 1 equiv) and phenylacetic acid (78 mg, 0.57 mmol, 4.5 equiv). The reaction mixture was heated at 60° C. for 1.5H, cooled, then partitioned between ethyl acetate (15 mL) and 1N sodium hydroxide (7 mL) and stirred for 3 h. The organic layer was collected, and the aqueous layer extracted twice more with ethyl acetate. The combined organics were dried over sodium sulfate, decanted, and concentrated. The residue was chromatographed (3:1 ethyl acetate/hexane) to produce 91 as a yellow solid (13.6 mg, 24%), mp (decomposition): 164.1-172.0° C.: 1H NMR (500 MHz, CDCl₃) δ 8.76 (br s, 1H), 8.00-7.92 (m, 2H), 7.80 (ddd, J=8.4, 1.3, 0.6 Hz, 1H), 7.66 (ddd, J=8.4, 6.9, 1.4 Hz, 1H), 7.50 (ddd, J=8.2, 6.9, 1.2 Hz, 1H), 7.42-7.37 (m, 1H), 7.31-7.26 (m, 2H), 7.23-7.15 (m, 3H), 3.97 (s, 2H), 3.28 (t, J=6.0 Hz, 2H), 3.07 (br s, 2H), 2.96 (s, 4H); ¹³C NMR (126 MHz, CDCl₃) δ 164.60, 150.20 (dd, J=248.1, 13.3 Hz), 147.45 (dd, J=246.7, 13.0 Hz), 146.90, 139.18, 138.69, 134.08 (dd, J=8.3, 3.5 Hz), 130.11, 128.67, 128.62, 127.40, 126.56, 124.35, 122.72, 117.52 (d, J=18.2 Hz), 115.64, 109.81 (d, J=21.9 Hz), 59.38, 52.87, 49.93, 32.93, 32.44, 29.69 (grease); ¹⁹F NMR (470 MHz, CDCl₃) δ−75.95 (trifluoroacetic acid), −134.90 (dt, J=20.8, 10.8 Hz), −141.26 (dddd, J=21.1, 10.3, 7.2, 3.8 Hz); ESI-MS [M+H]⁺ m/z calcd for $C_{27}H_{24}F_2N_3O$, 444.18; found, 444.5.

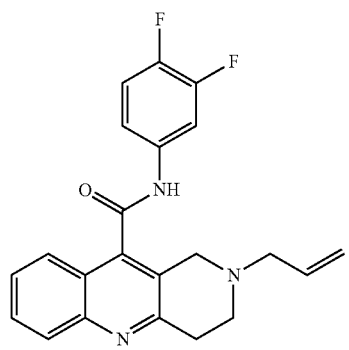 [SMILES: C=CCN1CCc2nc3ccccc3c(C(=O)Nc3ccc(F)c(F)c3)c2C1]

2-Allyl-N-(3,4-difluorophenyl)-1,2,3,4-tetrahydrobenzo[b][1,6]naphthyridine-10-carboxamide (92)

A solution of amine 88 (39 mg, 0.12 mmol, 1 equiv) in acetone (3.5 mL) was stirred at room temperature. Allyl bromide (11 µL, 0.13 mmol, 1.1 equiv) was added followed by potassium carbonate (16 mg, 0.12 mmol, 1 equiv). The reaction was stirred for 3H, then heated at reflux and stirred for another 2 h. The reaction was cooled to room temperature, filtered, and the filtrate concentrated. The residue was chromatographed (5% methanol in dichloromethane) to produce 92 (6.4 mg, 15%): $^1$H NMR (500 MHz, CDCl$_3$) δ 8.93 (s, 1H), 8.03 (d, J=7.3 Hz, 1H), 7.93 (s, 1H), 7.87 (d, J=7.8 Hz, 1H), 7.77-7.70 (m, 1H), 7.56 (t, J=7.3 Hz, 1H), 7.37 (s, 1H), 7.21-7.11 (m, 1H), 6.07-5.95 (m, 1H), 5.46-5.36 (m, 2H), 4.08 (s, 2H), 3.47 (s, 2H), 3.38 (d, J=6.8 Hz, 2H), 3.21 (s, 2H); ESI-MS [M+H]$^+$ m/z calcd for C$_{22}$H$_{20}$F$_2$N$_3$O, 380.15; found, 380.4.

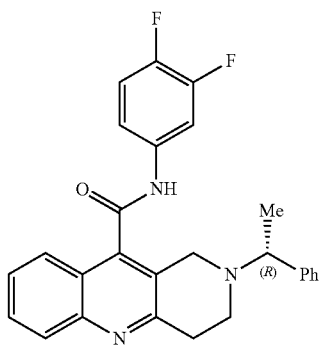

(R)—N-(3,4-Difluorophenyl)-2-(1-phenylethyl)-1,2,3,4-tetrahydrobenzo[b][1,6]naphthyridine-10-carboxamide (93)

A solution of potassium hydroxide (139 mg, 2.5 mmol, 4.5 equiv) in 50% aq dioxane (3 mL) was stirred at room temperature. Isatin (121 mg, 0.83 mmol, 1.5 equiv) was added, whereupon the solution turned black in color. After 20 min the solution cleared to a yellow color. R-piperidinone 134 (111 mg, 0.55 mmol, 1 equiv) was added as a solution in dioxane (1 mL). The reaction mixture was heated at reflux for 16 h. The reaction mixture was cooled, and then 1N hydrochloric acid (3 mL) was added until solids formed. The suspension was filtered, and the filtrate was concentrated. The residue was dissolved in ethanol and acidified with hydrochloric acid (37% w/w) until a precipitate formed. The suspension was filtered, and the solids were taken to the next step without further purification. A portion of the solids (40 mg, 0.12 mmol, 1 equiv) was suspended in acetonitrile (400 µL). 3,4-Difluoroaniline (18 µL, 0.18 mmol, 1.5 equiv) was added followed by phosphorous oxychloride (12 µL, 0.13 mmol, 1.1 equiv). The reaction mixture was heated at reflux for 3H, cooled, and then quenched with saturated sodium bicarbonate (5 mL). A white precipitate formed. The suspension was filtered giving 93 as a white solid (5.7 mg, 11%), mp (decomposition): 230.6-234.6° C.: 1H NMR (500 MHz, CDCl$_3$) δ 8.00 (d, J=8.0 Hz, 1H), 7.78 (d, J=8.0 Hz, 1H), 7.69-7.66 (m, 2H), 7.52-7.49 (m, 2H), 7.35-7.13 (m, 13H, overlapped with chloroform), 3.95 (d, J=15 Hz, 1H), 3.79 (d, J=14.5 Hz, 1H), 3.73-3.61 (m, 1H), 3.23-3.21 (m, 2H), 3.00-2.82 (m, 2H), 1.48 (d, J=6.0 Hz, 4H); $^{19}$F NMR (470 MHz, CDCl$_3$) δ−134.89, −140.89; ESI-MS [M+H]$^+$ m/z calcd for C$_{27}$H$_{24}$F$_2$N$_3$O, 444.18; found, 444.1.

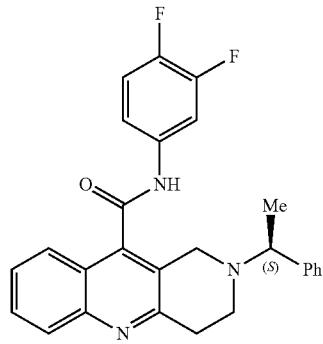

(S)—N-(3,4-Difluorophenyl)-2-(1-phenylethyl)-1,2,3,4-tetrahydrobenzo[b][1,6]naphthyridine-10-carboxamide (94)

A solution of potassium hydroxide (673 mg, 12 mmol, 12 equiv) in 50% aq dioxane (3 mL) was stirred at room temperature. Isatin (177 mg, 1.2 mmol, 1.2 equiv) was added, whereupon the solution turned black in color. After 20 min, the solution cleared to a yellow color and a solution of S-piperidinone 135 (206 mg, 1.0 mmol, 1 equiv) in dioxane (1 mL) was added. The reaction mixture was heated at reflux and stirred for 16 h. The reaction mixture was cooled, and then 1N hydrochloric acid (3 mL) was added until solids formed. The suspension was filtered, and the filtrate concentrated. The residue was dissolved in ethanol and acidified with hydrochloric acid (37% w/w) until precipitate formed. The suspension was filtered, and the solids brought to the next step without further purification. A portion of the solids (26 mg, 0.078 mmol, 1 equiv) was suspended in acetonitrile (800 µL). 3,4-Difluoroaniline (11.6 µL, 0.12 mmol, 1.5 equiv) was added followed by phosphorous oxychloride (8 µL, 0.086 mmol, 1.1 equiv). The reaction mixture was heated at reflux for 3H, cooled, then quenched with saturated sodium bicarbonate. The reaction was extracted with ethyl acetate and the resulting organic layer was dried over sodium sulfate, decanted, and concentrated. The residue was chromatographed (2:1 ethyl acetate/hexane) to produce a white solid (4.7 mg, 14%): $^1$H NMR (300 MHz, CDCl$_3$) δ 7.91 (d, J=8.4 Hz, 1H), 7.86 (s, 1H), 7.71 (dd, J=8.1, 1.3 Hz, 1H), 7.67-7.53 (m, 2H), 7.47-7.38 (m, 1H), 7.33-7.05 (m, 10H), 3.87 (d, J=15.7 Hz, 1H), 3.70 (d, J=15.6 Hz, 1H), 3.60 (q, J=6.8 Hz, 1H), 3.17-3.07 (m, 2H), 2.95-2.73 (m, 2H), 1.41 (d, J=6.7 Hz, 3H).

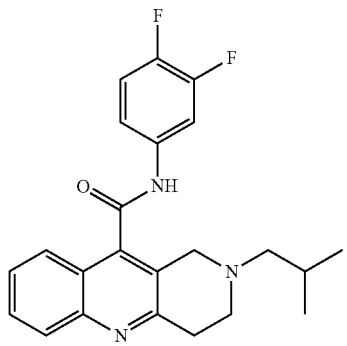 [SMILES: CC(C)CN1CCc2nc3ccccc3c(C(=O)Nc3ccc(F)c(F)c3)c2C1]

N-(3,4-Difluorophenyl)-2-isobutyl-1,2,3,4-tetrahydrobenzo[b][1,6]naphthyridine-10-carboxamide (95)

A solution of amine 88 (16.4 mg, 0.0483 mmol, 1 equiv) in dichloroethane 480 µL) is stirred at room temperature. Isobutyraldehyde (4.85 µL, 0.0531 mmol, 1.1 equiv) is added followed by sodium triacetoxyborohydride (14.8 mg, 0.0698 mmol, 1.4 equiv). The reaction is monitored by TLC to check for the disappearance of starting material. After completion, the reaction is quenched with saturated sodium bicarbonate (10 mL) and extracted with dichloromethane (5×10 mL). The organics are combined, dried over sodium sulfate, and concentrated. The residue was chromatographed (24:1 dichloromethane/methanol) to afford a yellow solid (11.7 mg, 61.3%), mp: 187.6-191.6° C.: $^1$H NMR (400 MHz, CDCl$_3$) δ 8.52 (br s, 1H), 7.99 (d, 1H, J=8.7 Hz), 7.95 (ddd, 1H, J=11.9, 7.1, 2.6 Hz), 7.81 (dd, 1H, J=8.4, 0.8 Hz), 7.69 (ddd, 1H, J=8.4, 6.9, 1.4 Hz), 7.52 (ddd, 1H, 8.3, 6.9, 1.2 Hz), 7.37 (dddd, 1H, J=8.9, 3.9, 2.6, 1.7 Hz), 7.19 (dt, 1H, J=9.8, 8.7 Hz), 3.89 (s, 2H), 3.27 (t, 2H, J=6.1 Hz), 2.97 (br s, 2H), 2.44 (d, 2H, J=7.4 Hz), 0.98 (d, 6H, J=6.6 Hz), 0.83-0.90 (m, 1H); ESI-MS [M+H]$^+$ calcd for C$_{23}$H$_{23}$F$_2$N$_3$O, 396.45; found, 396.0.

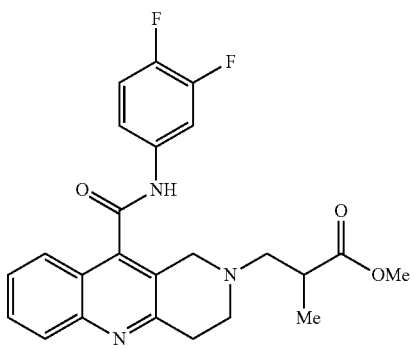

Methyl 3-(10-((3,4-difluorophenyl)carbamoyl)-3,4-dihydrobenzo[b][1,6]naphthyridin-2(1H)-yl)-2-methylpropanoate (97)

A mixture of amide 88 (49.7 mg, 0.147 mmol, 1 equiv) and neat methyl methacrylate (200 µL, 1.88 mmol, 12.8 equiv) was stirred at room temperature for 15 h. The reaction mixture was heated to 60° C. and stirred at that temperature for 24 h. DBU (44 µL, 0.293 mmol, 2 equiv) was added, and the mixture stirred for an additional 15 h. The solution was concentrated, and the residue chromatographed (1:1 ethyl acetate/hexanes) to afford the product as a white solid (23.9 mg, 37.1% yield), mp: 169.1-177.8° C.: $^1$H NMR (400 MHz, CDCl$_3$) δ 8.82 (s, 1H), 7.97 (ddd, 1H, J=11.9, 7.1, 2.5 Hz), 7.89 (d, 1H, J=8.4 Hz), 7.75 (d, 1H, J=8.3 Hz), 7.64 (ddd, 1H, J=8.2, 7.0, 1.2 Hz), 7.46 (ddd, 1H, J=8.0, 6.9, 0.8 Hz), 7.43-7.46 (m, 1H), 7.20 (dt, 1H, J=9.8, 8.9 Hz), 3.75 (app dd (ab q), 2H, J=15.6 Hz), 3.63 (s, 3H), 3.09 (app t, 2H, J=5.89 Hz), 2.88 (app dd, 2H, J=11.9, 9.0 Hz), 2.74-2.81 (m, 2H), 2.50 (dd, 1H, J=12.1, 5.5 Hz), 1.16 (d, 3H, J=6.8 Hz); ESI-MS [M+H]$^+$ calcd for C$_{24}$H$_{23}$F$_2$N$_3$O$_4$, 440.46; found, 440.4

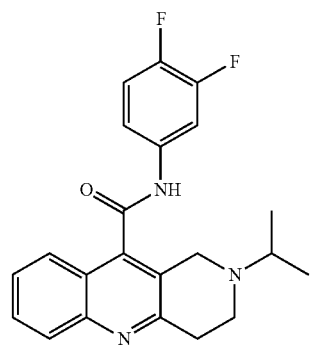 [SMILES: CC(C)N1CCc2nc3ccccc3c(C(=O)Nc3ccc(F)c(F)c3)c2C1]

N-(3,4-Difluorophenyl)-2-isopropyl-1,2,3,4-tetrahydrobenzo[b][1,6]naphthyridine-10-carboxamide (96)

A solution of amine 88 (50 mg, 0.15 mmol, 1 equiv) in dichloroethane (1.5 mL) is stirred at room temperature. Acetone (21 µL, 0.29 mmol, 2 equiv) is added followed by sodium triacetoxyborohydride (43 mg, 0.21 mmol, 1.4 equiv). The reaction is monitored by TLC to check for the disappearance of starting material. After completion, the reaction is quenched with saturated sodium bicarbonate (10 mL) and extracted with dichloromethane (2×10 mL). The combined organics were dried over sodium sulfate, decanted, and concentrated. The residue is chromatographed (15% methanol in dichloromethane) to produce 96 as a solid (17 mg, 30%), mp: 173.5-176.7° C.: 1H NMR (500 MHz, CD$_3$OD) δ 8.00 (dt, J=8.5, 0.9 Hz, 1H), 7.89 (ddd, J=12.5, 7.3, 2.6 Hz, 1H), 7.85 (d, J=8.3 Hz, 1H), 7.77 (ddd, J=8.4, 6.9, 1.4 Hz, 1H), 7.61 (ddd, J=8.3, 6.9, 1.2 Hz, 1H), 7.40 (dddd, J=9.0, 4.1, 2.6, 1.6 Hz, 1H), 7.30 (dt, J=10.3, 8.8 Hz, 1H), 4.01 (br s, 1H), 3.95 (br s, 1H), 3.28 (t, J=6.2 Hz, 2H), 3.11-2.99 (m, 3H), 1.17 (d, J=6.6 Hz, 6H); ESI-MS [M+H]$^+$ m/z calcd for C$_{22}$H$_{22}$F$_2$N$_3$O, 382.17; found, 382.4.

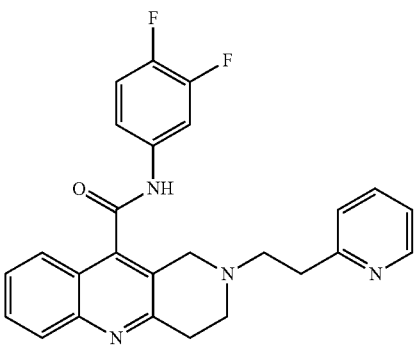 [SMILES: O=C(Nc1ccc(F)c(F)c1)c1c2c(nc3ccccc13)CCN(CCc1ccccn1)C2]

N-(3,4-Difluorophenyl)-2-(2-(pyridin-2-yl)ethyl)-1,2,3,4-tetrahydrobenzo[b][1,6]naphthyridine-10-carboxamide (98)

A suspension of amine 88 (30 mg, 0.089 mmol, 1 equiv) in ethanol (500 µL) was stirred in a thick-walled glass tube under a nitrogen atmosphere at room temperature. Acetic acid (5 µL, 0.089 mmol, 1 equiv) was added followed by vinyl pyridine (20 mg, 2.1 equiv). The reaction was sealed and heated to 100° C. for 16 h. The reaction was then concentrated and the residue was chromatographed (10% methanol in dichloromethane) to produce 98 as a white solid (25 mg, 63%), mp: 212.0-216.0° C.: 1H NMR (500 MHz, CDCl$_3$) δ 9.12 (s, 1H), 8.38 (d, J=4.9 Hz, 1H), 7.97 (ddd, J=12.1, 6.9, 2.6 Hz, 1H), 7.88 (d, J=8.5 Hz, 1H), 7.76 (d, J=8.3 Hz, 1H), 7.61 (dd, J=8.4, 7.0 Hz, 1H), 7.55 (t, J=7.7 Hz, 1H), 7.48-7.43 (m, 2H), 7.21 (q, J=9.1 Hz, 1H), 7.15 (d, J=7.6 Hz, 1H), 7.06-7.02 (m, 1H), 3.83 (s, 2H), 3.12 (t, J=6.1 Hz, 2H), 3.06-2.98 (m, 2H), 2.98-2.92 (m, 2H), 2.88 (d, J=6.4 Hz, 2H); $^{13}$C NMR (126 MHz, CDCl$_3$) δ 164.89, 159.57, 156.61, 150.25 (dd, J=247.8, 13.2 Hz), 147.70 (dd, J=246.7, 13.2 Hz), 146.47, 138.74, 136.58, 134.40 (dd, J=8.6, 3.2 Hz), 129.81, 128.33, 127.17, 124.32, 124.20, 123.24, 122.59, 121.40, 117.54 (d, J=17.7 Hz), 115.50 (dd, J=5.8, 3.7 Hz), 109.72 (d, J=21.9 Hz), 57.45, 52.67, 50.05, 35.67, 32.89; $^{19}$F NMR (470 MHz, CDCl$_3$) δ−134.93 (ddd, J=21.3, 12.0, 8.6 Hz), −141.45 (dddd, J=21.1, 10.5, 7.1, 3.7 Hz); ESI-MS [M+H]$^+$ m/z calcd for C$_{26}$H$_{23}$F$_2$N$_4$O$_1$, 445.18; found, 445.2.

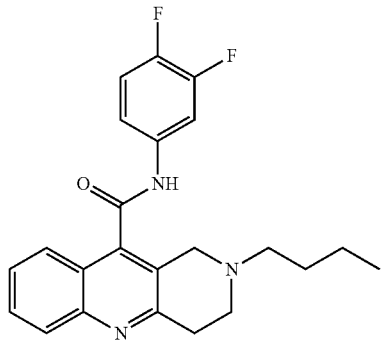 [SMILES: CCCCN1CCc2nc3ccccc3c(C(=O)Nc3ccc(F)c(F)c3)c2C1]

2-Butyl-N-(3,4-difluorophenyl)-1,2,3,4-tetrahydrobenzo[b][1,6]naphthyridine-10-carboxamide (99)

The TBN was prepared from amine 88 (30 mg, 0.088 mmol, 1 equiv) and butyraldehyde (8.8 µL, 0.097 mmol, 1.1 equiv) by following the procedure for 95. Chromatography with 5% methanol in dichloromethane afforded the product as a yellow solid with 8% oxidized impurity (35 mg, 44%), mp: 149.6-155.6° C.: $^1$H NMR (400 MHz, CDCl$_3$) δ 8.72 (br s, 1H), 8.02 (ddd, J=8.5, 1.3, 0.7 Hz, 1H), 7.95 (ddd, J=12.0, 7.1, 2.6 Hz, 1H), 7.85 (d, J=8.4 Hz, 1H), 7.72 (ddd, J=8.4, 6.9, 1.4 Hz, 1H), 7.54 (ddd, J=8.3, 6.9, 1.2 Hz, 1H), 7.40-7.35 (m, 1H), 7.18 (dt, J=10.0, 8.8 Hz, 1H), 4.01 (s, 2H), 3.36 (t, J=6.3 Hz, 2H), 3.14 (s, 2H), 2.82-2.72 (m, 2H), 1.68 (p, J=7.5 Hz, 2H), 1.40 (h, J=7.5, 7.1 Hz, 2H), 0.95 (t, J=7.3 Hz, 3H); ESI-MS [M+H]$^+$ m/z calcd for C$_{23}$H$_{24}$F$_2$N$_3$O, 396.18; found, 396.1.

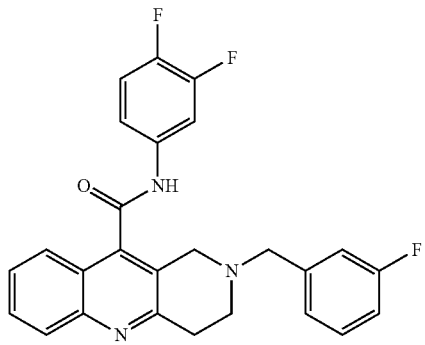 [SMILES: O=C(Nc1ccc(F)c(F)c1)c1c2c(nc3ccccc13)CCN(Cc1cccc(F)c1)C2]

N-(3,4-Difluorophenyl)-2-(3-fluorobenzyl)-1,2,3,4-tetrahydrobenzo[b][1,6]naphthyridine-10-carboxamide (100)

The TBN was prepared from amine 88 (20 mg, 0.059 mmol, 1 equiv) and 3-fluorobenzaldehyde (6.8 µL, 0.065 mmol, 1.1 equiv) by following the procedure for 95. Chromatography with 5% methanol in dichloromethane afforded the product as a yellow solid (12 mg, 45%), mp: 228.0-230.6° C.: $^1$H NMR (400 MHz, CDCl$_3$) δ 8.49 (br s, 1H), 8.02 (d, J=8.5 Hz, 1H), 7.85 (d, J=7.2 Hz, 1H), 7.82 (ddd, J=11.6, 7.0, 2.4 Hz, 1H), 7.72 (ddd, J=8.4, 6.7, 1.4 Hz, 1H), 7.55 (ddd, J=8.2, 6.8, 1.1 Hz, 1H), 7.34-7.26 (m, 2H), 7.25-7.13 (m, 3H), 7.00 (t, J=8.3 Hz, 1H), 4.02 (s, 2H), 3.90 (s, 2H), 3.32 (d, J=6.7 Hz, 2H), 3.09 (s, 2H); ESI-MS [M+H]$^+$ m/z calcd for C$_{26}$H$_{21}$F$_3$N$_3$O, 448.16; found, 448.3.

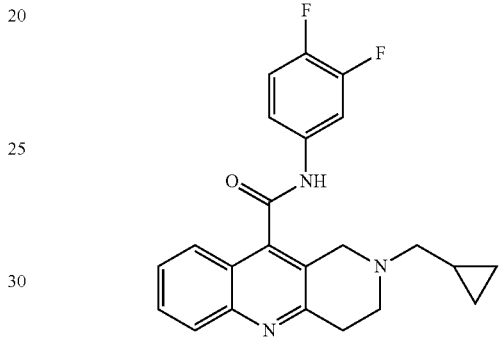

2-(Cyclopropylmethyl)-N-(3,4-difluorophenyl)-1,2,3,4-tetrahydrobenzo[b][1,6]naphthyridine-10-carboxamide (101)

A solution of amine 88 (14.9 mg, 0.0439 mmol, 1.0 equiv.) in dichloroethane (440 µL) was stirred at room temperature. Cyclopropane-carboxaldehyde (3.6 µL, 0.0482 mmol, 1.1 equiv.) was added, followed by sodium triacetoxyborohydride (14.2 mg, 0.0670 mmol, 1.5 equiv). The reaction mixture was stirred for 24H, then additional portions of cyclopropane-carboxaldehyde (2.0 µL, 0.0268 mmol, 0.6 equiv.) and sodium triacetoxyborohydride (14.0 mg, 0.0661 mmol, 1.5 equiv.) were added. The reaction mixture was heated at 50° C. for another 18 h, cooled to room temperature, and quenched with saturated sodium bicarbonate solution (5 mL). The mixture was extracted with dichloromethane (5×10 mL), and the combined organic solution dried over anhydrous sodium sulfate, decanted, and concentrated. The residue was chromatographed (24:1 dichloromethane/methanol) to afford a yellow solid (8.5 mg, 49.2% produce), mp (decomposition): 144.1-151.8° C.: $^1$H NMR (400 MHz, CDCl$_3$) δ 8.05 (d, 1H, J=8.4 Hz), 7.99 (ddd, 1H, J=11.9, 7.1, 2.4 Hz), 7.91 (dd, 1H, J=8.5, 0.8 Hz), 7.75 (ddd, 1H, J=8.3, 6.9, 1.4 Hz), 7.58 (ddd, 1H, J=8.0, 6.6, 0.9 Hz), 7.42-7.48 (m, 1H), 7.16 (dt, 1H, J=9.8, 8.9 Hz), 3.52 (br s, 1H), 2.90 (br d, 2H, J=7.0 Hz), 1.15 (d, 1H, J=6.4 Hz), 0.90-0.80 (m, 6H, includes residual grease peak), 0.71 (br d, 2H, J=5.29 Hz), 0.41 (br d, 2H, J=3.74 Hz); ESI-MS [M+H]$^+$ calcd for C$_{23}$H$_{21}$F$_2$N$_3$O, 394.44; found, 394.3.

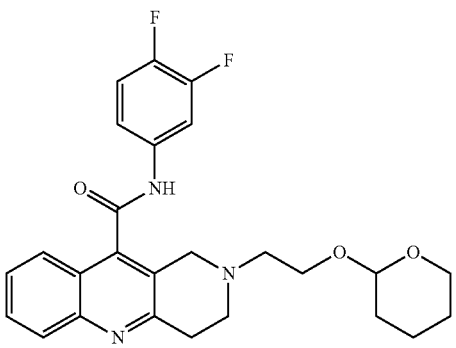 [SMILES: O=C(Nc1ccc(F)c(F)c1)c1c2c(nc3ccccc13)CCN(CCOC1CCCCO1)C2]

N-(3,4-Difluorophenyl)-2-(2-((tetrahydro-2H-pyran-2-yl)oxy)ethyl)-1,2,3,4-tetrahydrobenzo[b][1,6]naphthyridine-10-carboxamide (102)

A suspension of amine 88 (102 mg, 0.30 mmol, 1 equiv) in DMF (2 mL) was stirred at room temperature. A portion of 2-(2-bromoethoxy)tetrahydro-2H-pyran (59 μL, 0.39 mmol, 1.3 equiv) was added followed by potassium carbonate (125 mg, 0.90 mmol, 3 equiv). The reaction mixture was heated at reflux for 8 h, cooled to room temperature, and stirred for 16 h. After heating at reflux for an additional 5H, the reaction was cooled, filtered, and quenched with saturated sodium bicarbonate (25 mL), which formed a suspension. The resulting solids were collected via filtration and partitioned between ethyl acetate and water. The organic layer was collected, dried over sodium sulfate, decanted, and concentrated. The residue was chromatographed (4% methanol in dichloromethane) to produce 102 as a yellow solid (16.5 mg, 12%), mp: 143.4-145.3° C.: $^1$H NMR (500 MHz, CDCl$_3$) δ 8.87 (s, 1H), 8.01 (ddd, J=11.9, 7.2, 2.5 Hz, 1H), 7.88 (d, J=8.5 Hz, 1H), 7.74 (d, J=8.4 Hz, 1H), 7.64 (ddd, J=8.3, 6.9, 1.4 Hz, 1H), 7.50-7.43 (m, 2H), 7.20 (q, J=9.0 Hz, 1H), 4.55 (t, J=3.6 Hz, 1H), 3.98-3.78 (m, 4H), 3.62 (dt, J=10.9, 5.5 Hz, 1H), 3.49-3.41 (m, 1H), 3.13 (t, J=6.3 Hz, 2H), 2.95-2.86 (m, 2H), 2.82 (t, J=5.5 Hz, 2H), 1.79-1.70 (m, 1H), 1.68-1.60 (m, 1H), 1.57-1.39 (m, 4H); ESI-MS [M+H]$^+$ m/z calcd for C$_{26}$H$_{28}$F$_2$N$_3$O$_3$, 468.20; found, 468.0.

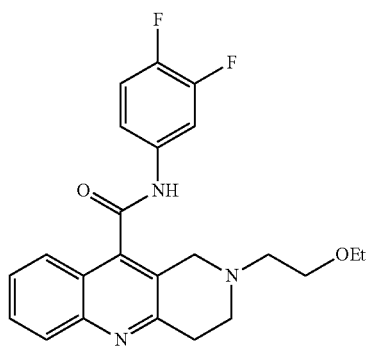 [SMILES: CCOCCN1CCc2nc3ccccc3c(C(=O)Nc3ccc(F)c(F)c3)c2C1]

N-(3,4-Difluorophenyl)-2-(2-ethoxyethyl)-1,2,3,4-tetrahydrobenzo[b][1,6]naphthyridine-10-carboxamide (103)

a suspension of amine 88 (50 mg, 0.15 mmol, 1 equiv) in DMF (500 μL) was stirred at room temperature. 1-Bromo-2-ethoxyethane (20 μL, 0.18 mmol, 1.2 equiv) was added followed by potassium carbonate (61 mg, 0.44 mmol, 3 equiv). The reaction was stirred at room temperature for 16 h then heated to 50° C. TLC was used to monitor the disappearance of starting material. After starting material was consumed, the reaction was filtered, and the filtrate concentrated. The residue was chromatographed twice (5% methanol in dichloromethane) to produce a white solid (32 mg, 53%): $^1$H NMR (500 MHz, CDCl$_3$) δ 8.83 (s, 1H), 7.99 (ddd, J=12.0, 7.1, 2.6 Hz, 1H), 7.87 (d, J=8.5 Hz, 1H), 7.73 (d, J=8.4 Hz, 1H), 7.63 (ddd, J=8.3, 6.7, 1.4 Hz, 1H), 7.49-7.43 (m, 2H), 7.20 (app q, J=9.1 Hz, 1H), 3.81 (s, 2H), 3.61 (t, J=5.4 Hz, 2H), 3.46 (q, J=7.0 Hz, 2H), 3.12 (t, J=6.1 Hz, 2H), 2.87 (t, J=6.1 Hz, 2H), 2.76 (t, J=5.4 Hz, 2H), 1.14 (t, J=7.0 Hz, 3H); ESI-MS [M+H]$^+$ m/z calcd for C$_{23}$H$_{24}$F$_2$N$_3$O$_2$, 412.18; found, 412.4.

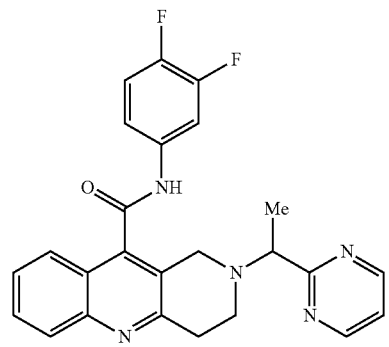

N-(3,4-Difluorophenyl)-2-(1-(pyrimidin-2-yl)ethyl)-1,2,3,4-tetrahydrobenzo[b][1,6]naphthyridine-10-carboxamide (104)

The TBN was prepared from amine 88 (56 mg, 0.165 mmol, 1 equiv) and 2-acetylpyrimidine (26 mg, 0.22 mmol, 1.3 equiv) by following the procedure for 95. Chromatography with 5% methanol in dichloromethane afforded the product as a yellow solid (24.1 mg, 33%), mp (decomposition): 183.6-191.2° C.: $^1$H NMR (500 MHz, CDCl$_3$) δ 8.67 (br t, J=4.4 Hz, 2H), 8.64 (s, 1H), 7.93 (dd, J=8.5, 3.4 Hz, 1H), 7.91-7.85 (m, 1H), 7.78 (dd, J=8.5, 3.4 Hz, 1H), 7.67-7.62 (m, 1H), 7.51-7.45 (m, 1H), 7.37-7.30 (m, 1H), 7.23-7.12 (m, 2H), 4.23-4.18 (m, 1H), 4.16 (d, J=16.4 Hz, 1H), 4.00 (d, J=15.9 Hz, 1H), 3.15 (s, 4H), 1.60 (app dd, J=7.1, 3.6 Hz, 3H); $^{19}$F NMR (470 MHz, CDCl$_3$) δ−134.96 (dt, J=21.7, 10.4 Hz), −141.13--141.80 (m); ESI-MS [M+H]$^+$ m/z calcd for C$_{25}$H$_{22}$F$_2$N$_5$O, 446.17; found, 446.1.

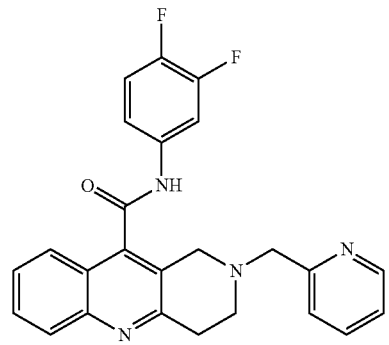

N-(3,4-Difluorophenyl)-2-(pyridin-2-ylmethyl)-1,2,3,4-tetrahydrobenzo[b][1,6]naphthyridine-10-carboxamide (105)

The TBN was prepared from amine 88 (12.5 mg, 0.037 mmol, 1 equiv) and picolinaldehyde (3.9 µL, 0.04 mmol, 1.1 equiv) by following the procedure for 95. Chromatography with 10% methanol in ethyl acetate afforded the product as a yellow solid (4.6 mg, 29%): 1H NMR (500 MHz, CDCl$_3$) δ 8.59 (s, 1H), 8.47 (ddt, J=5.0, 1.8, 0.9 Hz, 1H), 7.95 (d, J=8.5 Hz, 1H), 7.84-7.75 (m, 1H), 7.78 (d, J=8.3 Hz, 1H), 7.65 (q, J=7.7 Hz, 2H), 7.49 (ddt, J=8.1, 6.9, 1.1 Hz, 1H), 7.40 (dd, J=7.9, 1.1 Hz, 1H), 7.32-7.28 (m, 1H), 7.20-7.13 (m, 2H), 3.88 (s, 2H), 3.83 (s, 2H), 3.18 (t, J=6.1 Hz, 2H), 2.92 (t, J=6.1 Hz, 2H).

N-(3,4-Difluorophenyl)-2-(4-fluorobenzyl)-1,2,3,4-tetrahydrobenzo[b][1,6]naphthyridine-10-carboxamide (107)

The TBN was prepared from amine 88 (20 mg, 0.059 mmol, 1 equiv) and 4-fluorobenzaldehyde (6.94 µL, 0.065 mmol, 1.1 equiv) by following the procedure for 95. Chromatography with 12:1 dichloromethane/methanol afforded the product as a yellow solid (17.4 mg, 65.9% produce), mp (decomposition): 220.2-236.4° C.: $^1$H NMR (400 MHz, CDCl$_3$) δ 8.59 (br s, 1H), 8.03 (d, 1H, J=8.6 Hz), 7.86 (dd, 1H, J=8.3, 0.6 Hz), 7.80-7.86 (m, 1H), 7.73 (ddd, 1H, J=8.1, 6.7, 1.0 Hz), 7.55 (ddd, 1H, J=8.3, 7.0, 1.0 Hz), 7.45 (ddd, 2H, J=7.7, 5.6, 0.6 Hz), 7.22-7.25 (m, 1H), 7.17 (dt, 1H, J=9.9, 8.9 Hz), 7.03 (t, 2H, J=8.5 Hz), 4.06 (br s, 2H), 3.93 (s, 2H), 3.37 (br s, 2H), 3.13 (br s, 2H); ESI-MS [M+H]$^+$ calcd for C$_{26}$H$_{20}$F$_3$N$_3$O, 447.46; found, 447.8.

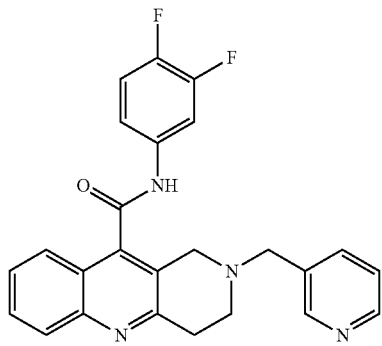 [SMILES: O=C(Nc1ccc(F)c(F)c1)c1c2c(nc3ccccc13)CCN(Cc1cccnc1)C2]

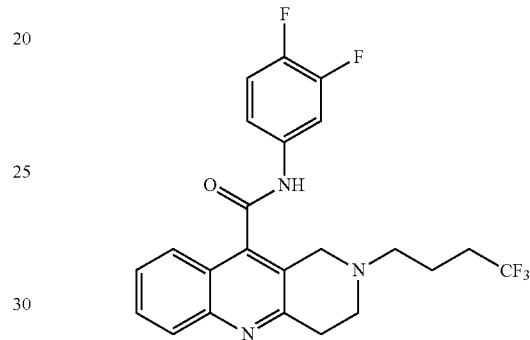

N-(3,4-Difluorophenyl)-2-(pyridin-3-ylmethyl)-1,2,3,4-tetrahydrobenzo[b][1,6]naphthyridine-10-carboxamide (106)

The TBN was prepared from amine 88 (8 mg, 0.024 mmol, 1 equiv) and nicotinaldehyde (2.5 µL, 0.026 mmol, 1.1 equiv) by following the procedure for 95. Chromatography with 10% methanol in ethyl acetate afforded the product as a yellow solid with 28% impurity by NMR (4.5 mg, 44%): 1H NMR (500 MHz, CDCl$_3$) δ 9.02 (s, 1H), 8.43 (s, 1H), 8.35 (d, J=5.0 Hz, 1H), 7.91 (d, J=8.5 Hz, 1H), 7.77 (d, J=8.4 Hz, 1H), 7.76-7.72 (m, 1H), 7.71-7.68 (m, 1H), 7.60 (d, J=8.0 Hz, 1H), 7.48 (t, J=7.9 Hz, 1H), 7.30-7.25 (m, 2H), 7.20-7.13 (m, 2H), 3.82 (s, 2H), 3.68 (s, 2H), 3.17 (t, J=6.1 Hz, 2H), 2.85 (s, 2H).

N-(3,4-Difluorophenyl)-2-(4,4,4-trifluorobutyl)-1,2,3,4-tetrahydrobenzo[b][1,6]naphthyridine-10-carboxamide (108)

The TBN was prepared from amine 88 (30 mg, 0.088 mmol, 1 equiv) and 4,4,4-trifluorobutanol (10.2 µL, 0.097 mmol, 1.1 equiv) by following the procedure for 95. Chromatography with 4% methanol in dichloromethane afforded the product as a white solid (26 mg, 65%), mp: 190.1-192.7° C.: 1H NMR (400 MHz, CDCl$_3$) δ 8.53 (br s, 1H), 7.97 (ddd, J=11.9, 7.0, 2.6 Hz, 1H), 7.93 (d, J=8.8 Hz, 1H), 7.77 (d, J=8.3 Hz, 1H), 7.66 (ddd, J=8.3, 6.9, 1.4 Hz, 1H), 7.50 (ddd, J=8.1, 6.9, 1.3 Hz, 1H), 7.44-7.38 (m, 1H), 7.22 (dt, J=9.9, 8.7 Hz, 1H), 3.77 (d, J=2.9 Hz, 2H), 3.16 (t, J=6.0 Hz, 2H), 2.83 (s, 2H), 2.62 (t, J=7.2 Hz, 2H), 2.27-2.09 (m, 3H), 1.84 (p, J=7.3 Hz, 2H); ESI-MS [M+H]$^+$ m/z calcd for C$_{24}$H$_{21}$F$_2$N$_4$OS, 451.13; found, 451.2.

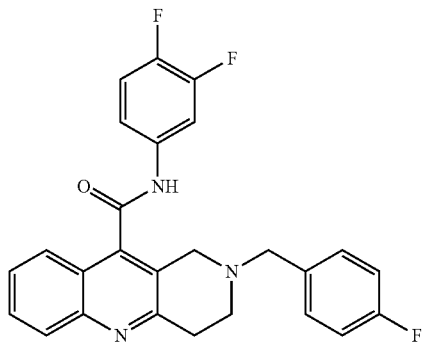 [SMILES: O=C(Nc1ccc(F)c(F)c1)c1c2c(nc3ccccc13)CCN(Cc1ccc(F)cc1)C2]

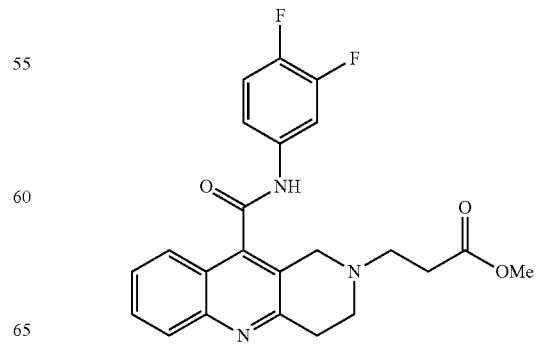

Methyl 3-(10-((3,4-difluorophenyl)carbamoyl)-3,4-dihydrobenzo[b][1,6]naphthyridin-2(1H)-yl)propanoate (109)

A solution of amine 88 (37.2 mg, 0.110 mmol, 1 equiv) in 1:1 methanol/acetonitrile (1.1 mL) was stirred at room temperature. Methyl acrylate (19.9 µL, 0.219 mmol, 2 equiv) was added, followed by DBU (16.4 µL, 0.110 mmol, 1 equiv). After 15H, the reaction mixture was condensed. The residue was chromatographed (19:1 dichloromethane/methanol) to afford the product as a yellow solid (13 mg, 47.8% yield): $^1$H NMR (500 MHz, CDCl$_3$) δ 8.70 (s, 1H), 7.97 (ddd, 1H, J=11.9, 7.1, 2.6 Hz), 7.92 (d, 1H, J=8.2 Hz), 7.78 (dd, 1H, J=6.7, 0.6 Hz), 7.66 (ddd, 1H, J=8.4, 6.9, 1.3 Hz), 7.49 (ddd, 1H, J=8.2, 6.9, 1.1 Hz), 7.43-7.46 (m, 1H), 7.21 (dt, 1H, J=7.9, 7.0 Hz), 3.82 (s, 2H), 3.66 (s, 3H), 3.16 (t, 2H, J=6.1 Hz), 2.94 (t, 2H, J=7.1 Hz), 2.89 (br s, 2H), 2.61 (t, 2H, J=7.1 Hz); ESI-MS [M+H]$^+$ calcd for C$_{24}$H$_{23}$F$_2$N$_3$O$_4$, 440.46; found, 440.4; ESI-MS [M+H]$^+$ calcd for C$_{23}$H$_{21}$F$_2$N$_3$O$_3$, 426.4; found, 426.3

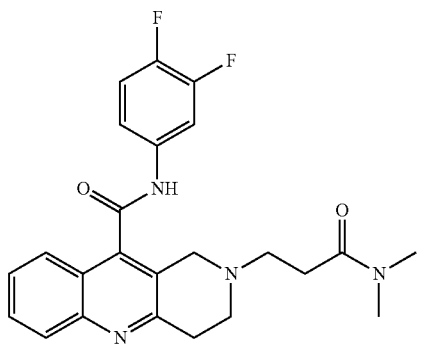 [SMILES: CN(C)C(=O)CCN1CCc2nc3ccccc3c(C(=O)Nc3ccc(F)c(F)c3)c2C1]

N-(3,4-Difluorophenyl)-2-(3-(dimethylamino)-3-oxopropyl)-1,2,3,4-tetrahydrobenzo[b][1,6]naphthyridine-10-carboxamide (110)

A suspension of amine 88 (30 mg, 0.09 mmol) in acetonitrile (740 µL) was stirred at room temperature under a nitrogen atmosphere. DBU (40 µL, 0.13 mmol, 1.5 equiv) was added followed by N,N-dimethylacrylamide (14 µL, 0.13 mmol, 1.5 equiv). The reaction mixture was heated at reflux for 3 h. The reaction mixture was cooled, concentrated, and the residue partitioned between ethyl acetate (10 mL) and water (10 mL). The organic layer was collected, and the aqueous layer washed with ethyl acetate (2×10 mL). The combined organics were dried over sodium sulfate, decanted, and concentrated. The residue was chromatographed twice. Once with 4% methanol in dichloromethane and one with 10% methanol in 2:1 dichloromethane/ethyl acetate. The resulting product contained 15% impurity by NMR (29.7 mg, 75%): ($^1$H NMR (500 MHz, CDCl$_3$) δ 9.40 (s, 1H), 7.95-7.90 (m, 1H), 7.93 (d, J=8.5 Hz, 1H), 7.78 (dd, J=8.4, 0.7 Hz, 1H), 7.64 (ddd, J=8.4, 6.8, 1.4 Hz, 1H), 7.46 (ddd, J=8.2, 6.8, 1.1 Hz, 1H), 7.49-7.42 (m, 1H), 7.17 (dt, J=9.9, 8.7 Hz, 1H), 3.82 (s, 2H), 3.16 (t, J=6.1 Hz, 2H), 2.86 (s, 5H), 2.81 (t, J=7.3 Hz, 2H), 2.62 (s, 3H), 2.49 (s, 2H), 2.45 (t, J=7.3 Hz, 2H); $^{19}$F NMR (470 MHz, CDCl$_3$) δ −134.26-−136.51 (m), −141.65 (dddd, J=21.2, 10.6, 7.1, 3.7 Hz); ESI-MS [M+H]$^+$ m/z calcd for C$_{24}$H$_{25}$F$_2$N$_4$O$_2$, 439.19; found, 439.1.

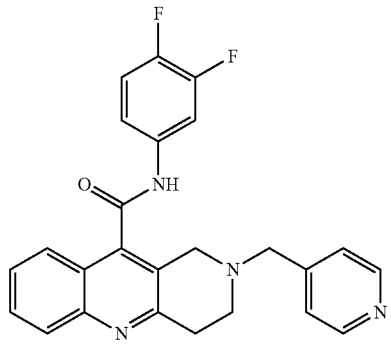 [SMILES: O=C(Nc1ccc(F)c(F)c1)c1c2c(nc3ccccc13)CCN(Cc1ccncc1)C2]

N-(3,4-Difluorophenyl)-2-(pyridin-4-ylmethyl)-1,2,3,4-tetrahydrobenzo[b][1,6]naphthyridine-10-carboxamide (111)

The TBN was prepared from amine 88 (8 mg, 0.024 mmol, 1 equiv) and isonicotinaldehyde (2.4 µL, 0.026 mmol, 1.1 equiv) by following the procedure for 95. Chromatography with 5% methanol in dichloromethane afforded the product as a yellow solid (4.7 mg, 45%): $^1$H NMR (500 MHz, CDCl$_3$) δ 8.49-8.40 (m, 3H), 7.96 (d, J=8.5 Hz, 1H), 7.85 (ddt, J=11.7, 7.5, 1.6 Hz, 1H), 7.79 (d, J=8.4 Hz, 1H), 7.68 (ddt, J=8.5, 6.9, 1.6 Hz, 1H), 7.52 (td, J=8.4, 7.0, 1.1 Hz, 1H), 7.27 (s, 1H), 7.23-7.12 (m, 1H), 3.86 (s, 2H), 3.70 (s, 2H), 3.18 (t, J=6.0 Hz, 2H), 2.81 (br t, J=6.1 Hz, 2H); ESI-MS [M+H]$^+$ m/z calcd for C$_{25}$H$_{21}$F$_2$N$_4$O, 431.16; found, 431.3.

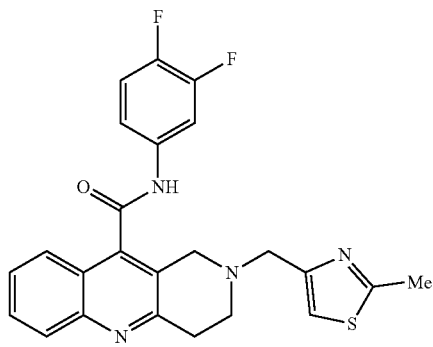 [SMILES: Cc1nc(CN2CCc3nc4ccccc4c(C(=O)Nc4ccc(F)c(F)c4)c3C2)cs1]

N-(3,4-Difluorophenyl)-2-((2-methylthiazol-4-yl)methyl)-1,2,3,4-tetrahydrobenzo[b][1,6]naphthyridine-10-carboxamide (112)

The TBN was prepared from amine 88 (30 mg, 0.088 mmol, 1 equiv) and 2-methylthiazole-4-carbaldehyde (12.3 mg, 0.097 mmol, 1.1 equiv) by following the procedure for 95. Chromatography with 6% methanol in dichloromethane afforded the product as an orange solid (28.2 mg, 70%), mp: 91.0-94.6° C.: 1H NMR (500 MHz, CDCl$_3$) δ 8.93 (s, 1H), 7.87 (d, J=7.8 Hz, 1H), 7.85 (ddd, J=11.9, 7.0, 2.6 Hz, 1H), 7.74 (ddd, J=8.4, 1.4, 0.6 Hz, 1H), 7.61 (ddd, J=8.4, 6.9, 1.4 Hz, 1H), 7.45 (ddd, J=8.2, 6.9, 1.2 Hz, 1H), 7.36 (dddd, J=9.0, 4.0, 2.6, 1.5 Hz, 1H), 7.17 (dt, J=9.9, 8.7 Hz, 1H), 6.99 (s, 1H), 3.82 (s, 2H), 3.76 (s, 2H), 3.12 (t, J=6.1 Hz, 2H), 2.88 (br s, 2H), 2.61 (s, 3H); ESI-MS [M+H]$^+$ m/z calcd for C$_{24}$H$_{21}$F$_2$N$_4$OS, 451.13; found, 451.2.

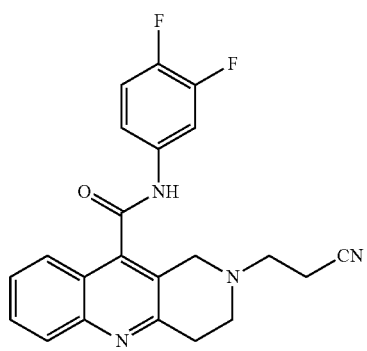 [SMILES: N#CCCN1CCc2nc3ccccc3c(C(=O)Nc3ccc(F)c(F)c3)c2C1]

2-(2-Cyanoethyl)-N-(3,4-difluorophenyl)-1,2,3,4-tetrahydrobenzo[b][1,6]naphthyridine-10-carboxamide (113)

A suspension of amine 88 (47.4 mg, 0.140 mmol, 1 equiv) in methanol (3 mL) was stirred at room temperature. Acrylonitrile (18.3 µL, 0.280 mmol, 2 equiv.) was added, followed by N,N-diisopropylethylamine (48.8 µL, 0.280 mmol, 2 equiv.). The reaction mixture was heated at 60° C. for 48 h. The reaction mixture was condensed and chromatographed (24:1 dichloromethane/methanol) to afford the product as a yellow solid (7.7 mg, 14.0% yield): $^1$H NMR (400 MHz, CD$_3$OD) δ 8.01 (d, 1H, J=8.4 Hz), 7.90 (ddd, 1H, J=12.4, 7.2, 2.4 Hz), 7.86 (dd, 1H, J=8.4, 0.8 Hz), 7.79 (ddd, 1H, J=8.8, 7.2, 1.6 Hz), 7.40 (dddd, 1H, J=9.2, 4.0, 2.4, 1.6 Hz), 7.29 (dt, 1H, J=10.0, 8.8 Hz), 4.00 (d, 2H, J=2.8 Hz), 3.29-3.32 (m, 5H, includes MeOH solvent peak), 3.05 (br s, 2H), 2.96 (t, 2H, J=6.8 Hz), 2.76 (t, 2H, J=6.8 Hz); ESI-MS [M+H]$^+$ calcd for C$_{22}$H$_{18}$F$_2$N$_4$O, 393.41; found, 393.5.

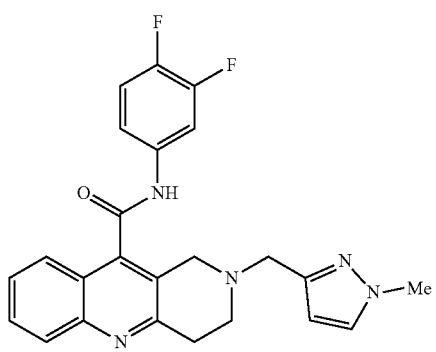 [SMILES: Cn1ccc(CN2CCc3nc4ccccc4c(C(=O)Nc4ccc(F)c(F)c4)c3C2)n1]

N-(3,4-Difluorophenyl)-2-((1-methyl-1H-pyrazol-3-yl)methyl)-1,2,3,4-tetrahydrobenzo[b][1,6]naphthyridine-10-carboxamide (114)

The TBN was prepared from amine 88 (19.2 mg, 0.057 mmol, 1 equiv) and 1-methyl-1H-pyrazole-3-carbaldehyde (6.01 µL, 0.062 mmol, 1.1 equiv) by following the procedure for 95. Chromatography with 19:1 dichloromethane/methanol afforded the product as a yellow solid (14.8 mg, 60% yield), mp (decomposition): 106.9-114.6° C.: $^1$H NMR (400 MHz, CDCl$_3$) δ 8.60 (s, 1H), 7.94 (d, 1H, J=8.5 Hz), 7.83 (ddd, 1H, J=12.0, 7.1, 2.7 Hz), 7.78 (ddd, 1H, J=8.4, 1.3, 0.5 Hz), 7.65 (ddd, 1H, J=8.4, 6.9, 1.4 Hz), 7.49 (ddd, 1H, J=8.2, 6.9, 1.2 Hz), 7.34 (dddd, 1H, J=8.9, 3.9, 2.6, 1.7 Hz), 7.26 (d, 1.6H, J=2.0 Hz, includes solvent CDCl$_3$ peak), 7.18 (dt, 1H, J=9.9, 8.8 Hz), 6.22 (d, 1H, J=2.2 Hz), 3.91 (s, 2H), 3.79 (s, 3H), 3.76 (s, 2H), 3.20 (t, 2H, J=6.2 Hz), 2.98 (app t, 2H, J=6.3 Hz); ESI-MS [M+H]$^+$ calcd for C$_{24}$H$_{21}$F$_2$N$_5$O, 434.46; found, 434.5

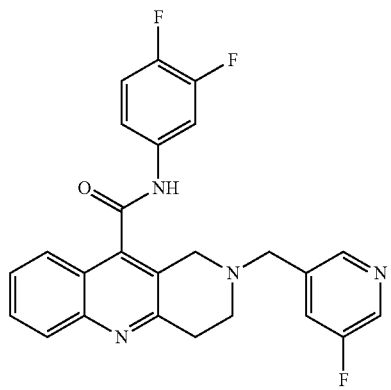 [SMILES: O=C(Nc1ccc(F)c(F)c1)c1c2c(nc3ccccc13)CCN(Cc1cncc(F)c1)C2]

N-(3,4-Difluorophenyl)-2-((5-fluoropyridin-3-yl)methyl)-1,2,3,4-tetrahydrobenzo[b][1,6]naphthyridine-10-carboxamide (115)

The TBN was prepared from amine 88 (21.5 mg, 0.063 mmol, 1 equiv) and 3-fluoro-5-formylpyridine (6.87 µL, 0.070 mmol, 1.1 equiv) by following the procedure for 95. Chromatography with 24:1 dichloromethane/methanol afforded the product as a yellow solid (9.8 mg, 34.5% yield), mp: 226.3-230.5° C.: $^1$H NMR (400 MHz, CDCl$_3$) δ 8.37-8.40 (m, 2H), 7.99 (d, 1H, J=8.6 Hz), 7.84 (d, 1H, J=8.4 Hz), 7.81-7.87 (m, 1H), 7.70 (ddd, 1H, J=8.0, 6.5, 0.8 Hz), 7.56 (ddd, 1H, J=7.8, 6.7, 0.6 Hz), 7.52 (br d, 1H, J=9.47 Hz), 7.28-7.31 (m, 1H), 7.19 (dt, 1H, J=9.5, 8.6 Hz), 3.97 (s, 2H), 3.82 (s, 2H), 3.25 (t, 2H, J=5.6 Hz), 2.93 (br s, 2H); ESI-MS [M+H]$^+$ calcd for C$_{25}$H$_{19}$F$_3$N$_4$O, 449.45; found, 449.1

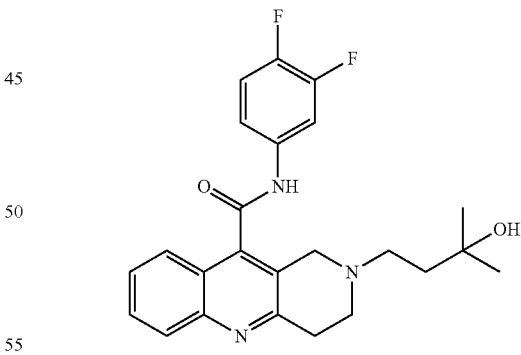

N-(3,4-Difluorophenyl)-2-(3-hydroxy-3-methylbutyl)-1,2,3,4-tetrahydrobenzo[b][1,6]naphthyridine-10-carboxamide (116)

A solution of TBN 109 (37 mg, 0.087 mmol, 1 equiv) in THF (500 µL) was stirred under a nitrogen atmosphere. Methyl magnesium bromide (3.0 M in Et$_2$O, 156 µL, 0.468 mmol, 5.4 equiv) was added and the reaction stirred at room temperature for 16 h. Water (10 mL) was added followed by saturated ammonium chloride (20 mL) and the resulting solution was extracted with ethyl acetate (3×20 mL). The organic extracts were combined, dried over sodium sulfate, and concentrated. The residue was chromatographed (10% methanol in dichloromethane) to produce 116 with 8% oxidized impurity by NMR (6.1 mg, 16%): $^1$H NMR (500 MHz, CDCl$_3$) δ 9.05 (br s, 1H), 8.02 (d, J=8.5 Hz, 1H), 7.96 (ddd, J=12.0, 7.1, 2.6 Hz, 1H), 7.86 (ddd, J=8.5, 1.4, 0.7 Hz, 1H), 7.72 (ddd, J=8.4, 6.9, 1.4 Hz, 1H), 7.55 (ddd, J=8.3, 6.9, 1.2 Hz, 1H), 7.44-7.39 (m, 1H), 7.18 (dt, J=9.8, 8.7 Hz, 1H), 4.07 (br s, 2H), 3.39 (d, J=15.0 Hz, 2H), 3.21 (br s, 2H), 3.02 (t, J=6.3 Hz, 2H), 1.80 (d, J=14.6 Hz, 2H), 1.26-1.24 (m, 1H), 1.22 (s, 5H); $^{19}$F NMR (470 MHz, CDCl$_3$) δ-134.89--135.33 (m), -141.30 (dddd, J=21.0, 10.3, 6.9, 3.8 Hz); ESI-MS [M+H]$^+$ m/z calcd for C$_{24}$H$_{26}$F$_2$N$_3$O$_2$, 426.19; found, 426.1.

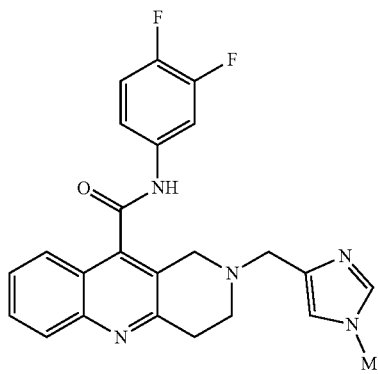

N-(3,4-Difluorophenyl)-2-((1-methyl-1H-imidazol-4-yl)methyl)-1,2,3,4-tetrahydrobenzo[b][1,6]naphthyridine-10-carboxamide (117)

The TBN was prepared from amine 88 (20 mg, 0.059 mmol, 1 equiv) and 1-methyl-1H-imidazole-4-carbaldehyde (7.1 mg, 0.065 mmol, 1.1 equiv) by following the procedure for 95. Chromatography with 10% methanol in dichloromethane afforded the product as a solid (7 mg, 28%): 1H NMR (500 MHz, CDCl$_3$) δ 9.81 (s, 1H), 7.95 (ddd, J=8.5, 1.3, 0.6 Hz, 1H), 7.83 (d, J=8.4 Hz, 1H), 7.86-7.77 (m, 1H), 7.65 (ddd, J=8.4, 6.9, 1.4 Hz, 1H), 7.48 (ddd, J=8.3, 6.9, 1.2 Hz, 1H), 7.40-7.34 (m, 1H), 7.15 (dt, J=9.9, 8.7 Hz, 1H), 7.04 (s, 1H), 6.77 (d, J=1.0 Hz, 1H), 3.94 (br s, 2H), 3.63 (s, 2H), 3.19 (t, J=6.3 Hz, 2H), 3.02 (br s, 3H); $^{19}$F NMR (470 MHz, CDCl$_3$) δ-135.31--135.67 (m), -141.82 (dddd, J=21.4, 10.6, 7.3, 3.9 Hz); ESI-MS [M+H]$^+$ m/z calcd for C$_{24}$H$_{22}$F$_2$N$_5$O, 434.17; found, 434.4.

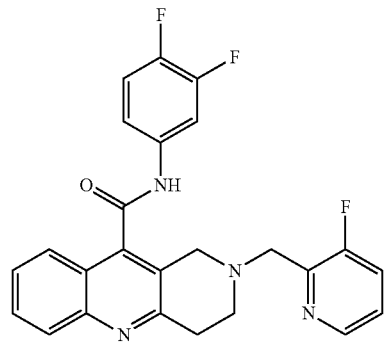 [SMILES: O=C(Nc1ccc(F)c(F)c1)c1c2c(nc3ccccc13)CCN(Cc1ncccc1F)C2]

N-(3,4-difluorophenyl)-2-((3-fluoropyridin-2-yl)methyl)-1,2,3,4-tetrahydrobenzo[b][1,6]naphthyridine-10-carboxamide (118)

The TBN was prepared from amine 88 (50 mg, 0.15 mmol, 1 equiv) and 3-fluoropicolinaldehyde (20 mg, 0.16 mmol, 1.1 equiv) by following the procedure for 95. Chromatography with 4% methanol in dichloromethane afforded the product as a yellow solid (46.7 mg, 69%), mp (decomposition): 142.5-149.0° C.: $^1$H NMR (400 MHz, CD$_3$OD) δ 8.32 (dt, J=4.7, 1.4 Hz, 1H), 7.98 (ddd, J=8.6, 1.2, 0.6 Hz, 1H), 7.82 (ddd, J=8.4, 1.5, 0.7 Hz, 1H), 7.86-7.76 (m, 1H), 7.75 (ddd, J=8.5, 6.9, 1.4 Hz, 1H), 7.61-7.55 (m, 2H), 7.38 (ddd, J=8.4, 4.7, 4.2 Hz, 1H), 7.34-7.26 (m, 2H), 4.02-3.98 (m, 2H), 3.96 (d, J=5.8 Hz, 2H), 3.27 (d, J=6.1 Hz, 2H), 3.11 (d, J=11.1 Hz, 2H). $^{19}$F NMR (376 MHz, CD$_3$OD) δ-125.12--125.37 (m), -138.34--138.65 (m), -144.33--144.77 (m); ESI-MS [M+H]$^+$ m/z calcd for C$_{25}$H$_{20}$F$_3$N$_4$O, 449.15; found, 449.3.

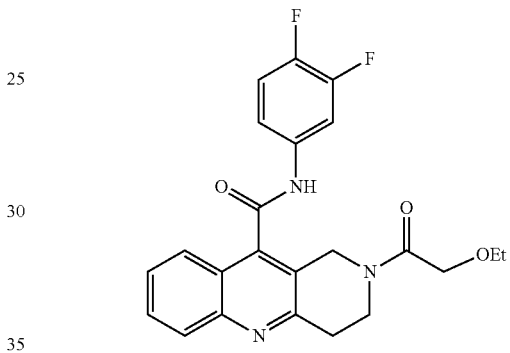

N-(3,4-Difluorophenyl)-2-(2-ethoxyacetyl)-1,2,3,4-tetrahydrobenzo[b][1,6]naphthyridine-10-carboxamide (119)

A mixture of ethoxyacetic acid (14 µL, 0.15 mmol, 1.5 equiv) and dichloromethane (1 mL) was stirred at room temperature. Amine 88 (34 mg, 0.10 mmol, 1 equiv) was added, followed by Hydroxybenzotriazole (15 mg, 0.11 mmol, 1.1 equiv), N-methylmorpholine (24 µL, 0.22 mmol, 2.2 equiv), and 1-Ethyl-3-(3-dimethylaminopropyl)carbodiimide (32 mg, 0.17 mmol, 1.7 equiv). The reaction was stirred for 16 h, then partitioned between dichloromethane (10 mL) and half saturated ammonium chloride (10 mL). The organic layer was collected, and the aqueous layer washed twice more with dichloromethane. The combined organic extracts were dried over sodium sulfate, decanted, and concentrated. The residue was chromatographed (ethyl acetate) to produce 119 as a yellow solid with 38% impurity (28 mg, 66%): 1H NMR (500 MHz, CDCl$_3$) δ 9.76 (s, 1H), 9.22 (s, 0.3H), 8.00 (d, J=8.4 Hz, 1H), 7.92-7.86 (m, 2H), 7.72 (ddd, J=8.4, 6.9, 1.4 Hz, 1H), 7.55 (ddd, J=8.2, 6.8, 1.2 Hz, 1H), 7.43-7.38 (m, 1H), 7.20 (q, J=9.1 Hz, 0.4H), 7.07 (q, J=8.9 Hz, 1H), 5.16 (br s, 2H), 4.79 (s, 0.7H), 4.45 (br s, 2H), 4.13-4.08 (m, 0.7H), 3.75 (br s, 2H), 3.55 (s, 2H), 3.36 (q, J=6.7 Hz, 0.7H), 3.25 (q, J=7.0 Hz, 2H), 3.18 (t, J=6.3 Hz, 2H), 3.08 (t, J=6.4 Hz, 1H), 1.25-1.24 (m, 0.5H), 1.11 (t, J=7.0 Hz, 3H), 0.92 (t, J=6.9 Hz, 1H); $^{13}$C NMR (126 MHz, CDCl$_3$) δ 169.15, 164.09, 155.29, 150.02 (dd, J=247.4, 13.9 Hz), 147.31 (dd, J=246.5, 12.3 Hz), 146.61, 139.87, 134.26 (dd, J=8.7, 2.5 Hz), 130.29, 128.45, 127.56, 124.95, 123.21, 122.46, 117.27 (d, J=18.4 Hz), 115.66, 109.68 (d, J=21.9 Hz), 69.84, 66.93, 42.63, 41.98, 33.29, 14.88; $^{19}$F NMR (470 MHz, CDCl$_3$) δ−134.76 (dt, J=21.1, 10.0 Hz), −135.15--135.48 (m), −140.73--141.10 (m), −141.66 (dddd, J=21.6, 10.8, 7.4, 3.9 Hz); ESI-MS [M+H]$^+$ m/z calcd for C$_{23}$H$_{22}$F$_2$N$_3$O$_3$, 426.16; found, 426.3.

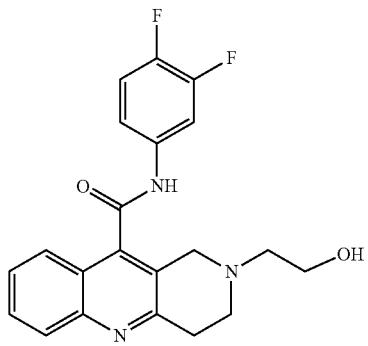 [SMILES: O=C(Nc1ccc(F)c(F)c1)c1c2c(nc3ccccc13)CCN(CCO)C2]

N-(3,4-Difluorophenyl)-2-(2-hydroxyethyl)-1,2,3,4-tetrahydrobenzo[b][1,6]naphthyridine-10-carboxamide (120)

A 700 μL, 4:2:1 mixture of acetic acid/THF/water was prepared. TBN 102 (13.1 mg, 0.028 mmol) was added and the solution was heated to 53° C. for 24 h. After cooling to room temperature, the solution was concentrated and the residue was chromatographed (10% methanol in dichloromethane) to produce 120 as a yellow solid (15 mg, >95%): $^1$H NMR (500 MHz, Methanol-d$_4$) δ 8.01 (d, J=8.5 Hz, 1H), 7.90 (ddd, J=12.4, 7.4, 2.4 Hz, 1H), 7.86 (d, J=8.5 Hz, 1H), 7.78 (ddd, J=8.5, 6.9, 1.4 Hz, 1H), 7.62 (ddd, J=8.3, 6.9, 1.2 Hz, 1H), 7.40 (dddd, J=9.1, 4.0, 2.6, 1.6 Hz, 1H), 7.30 (dt, J=10.4, 8.8 Hz, 1H), 4.07 (d, J=10.0 Hz, 2H), 3.79 (t, J=5.6 Hz, 2H), 3.33 (t, J=6.5 Hz, 2H), 3.18 (t, J=6.3 Hz, 2H), 2.87 (t, J=5.7 Hz, 2H).

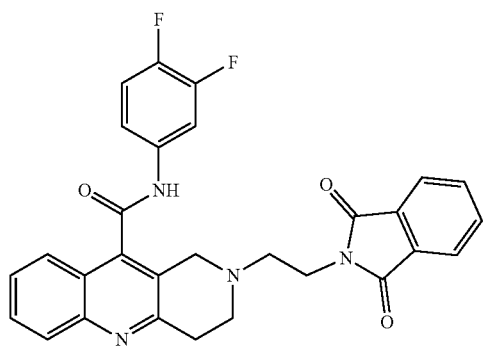 [SMILES: O=C(Nc1ccc(F)c(F)c1)c1c2c(nc3ccccc13)CCN(CCN1C(=O)c3ccccc3C1=O)C2]

N-(3,4-Difluorophenyl)-2-(2-(1,3-dioxoisoindolin-2-yl)ethyl)-1,2,3,4-tetrahydrobenzo[b][1,6]naphthyridine-10-carboxamide (121)

A suspension of amine 88 (100 mg, 0.29 mmol, 1 equiv) in DMF (1.45 mL) was stirred at room temperature. N-(2-Bromoethyl)phthalamide (97 mg, 0.38 mmol, 1.3 equiv) was added followed by potassium carbonate (120 mg, 0.87 mmol, 3 equiv). The reaction mixture was heated at 50° C. for 24 h, cooled, and stirred at room temperature for 48 h. Saturated sodium bicarbonate (15 mL) was added causing a solid to precipitate. The suspension was filtered, and the resulting solids partitioned between water (20 mL) and ethyl acetate (20 mL). The organic layer was collected, and the aqueous layer washed with ethyl acetate (2×20 mL). The combined organic extracts were dried over sodium sulfate, decanted, and concentrated. The residue was chromatographed (ethyl acetate) to produce 121 as a yellow solid (46 mg, 31%): $^1$H NMR (500 MHz, CDCl$_3$) δ 8.87 (br s, 1H), 7.99 (d, J=8.3 Hz, 1H), 7.98-7.94 (m, 1H), 7.90 (d, J=8.3 Hz, 1H), 7.77 (dd, J=5.5, 3.1 Hz, 2H), 7.70-7.66 (m, 3H), 7.55 (t, J=7.6 Hz, 1H), 7.52-7.47 (m, 1H), 7.18 (app q, J=9.0 Hz, 1H), 4.51 (br s, 2H), 3.92 (s, 2H), 3.18 (s, 2H), 3.15-2.80 (m, 4H); ESI-MS [M+H]$^+$ m/z calcd for C$_{29}$H$_{23}$F$_2$N$_4$O$_3$, 513.17; found, 513.0.

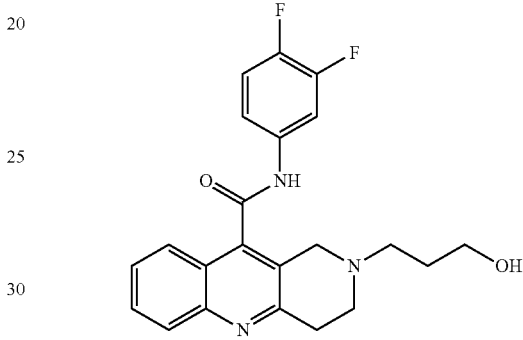

N-(3,4-Difluorophenyl)-2-(3-hydroxypropyl)-1,2,3,4-tetrahydrobenzo[b][1,6]naphthyridine-10-carboxamide (122)

A solution of amide 109 (20.3 mg, 0.0477 mmol, 1 equiv) in THF (1 mL) is cooled to 0° C. Lithium aluminum hydride (2.1 mg, 0.0553 mmol, 1.2 equiv) is added, and the reaction is warmed to room temperature. After 24 h, an additional portion of lithium aluminum hydride (9.0 mg, 0.237 mmol, 5 equiv) was added. After 3 h, the reaction was quenched with 2N sodium hydroxide (200 μL) and water (500 μL), cooled to 0° C., and stirred for 30 min. The mixture was filtered, and the resulting solids rinsed with dichloromethane. The filtrate and dichloromethane were combined then washed with water (2×20 mL). The organic layer was dried over sodium sulfate, decanted, and concentrated. The residue was chromatographed (12:1 dichloromethane/methanol) to afford the product as a yellow solid (5.4 mg, 28.5% yield): $^1$H NMR (500 MHz, CDCl$_3$) δ 9.23 (s, 1H), 7.97 (d, 1H, J=8.5 Hz), 7.93 (ddd, 1H, J=12.0, 7.2, 2.3 Hz), 7.83 (d, 1H, J=7.8 Hz), 7.69 (ddd, 1H, J=8.4, 6.9, 1.3 Hz), 7.53 (ddd, 1H, J=8.2, 7.0, 1.1 Hz), 7.37-7.40 (m, 1H), 7.18 (dt, 1H, J=7.8, 7.0 Hz), 3.99 (br s, 2H), 3.71 (t, 2H, J=5.3 Hz), 3.46 (br s, 2H), 3.26 (t, 2H, J=6.2 Hz), 2.90 (t, 2H, J=6.0 Hz), 1.81 (p, 2H, J=5.7 Hz); $^{19}$F NMR (470 MHz, CDCl$_3$) δ−75.09 (impurity), −75.95 (trifluoroacetic acid), −135.07 (ddd, J=21.2, 12.1, 8.9 Hz), −141.36 (dddd, J=21.3, 10.5, 7.2, 3.8 Hz); ESI-MS [M+H]$^+$ calcd for C$_{22}$H$_{21}$F$_2$N$_3$O, 398.43; found, 398.1

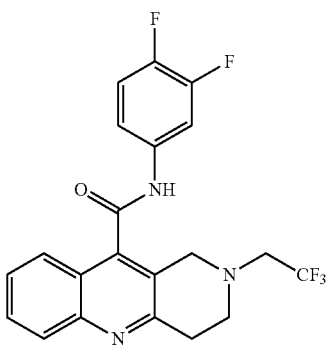 [SMILES: O=C(Nc1ccc(F)c(F)c1)c1c2c(nc3ccccc13)CCN(CC(F)(F)F)C2]

N-(3,4-Difluorophenyl)-2-(2,2,2-trifluoroethyl)-1,2,3,4-tetrahydrobenzo[b][1,6]naphthyridine-10-carboxamide (123)

A solution of karstedt's catalyst (2% in xylenes, 8.5 µL, 0.05 equiv) in dioxane (520 µL) was stirred under a nitrogen atmosphere. In quick succession, phenylsilane (145 µL, 1.2 mmol, 8 equiv) was added, followed by secondary amine 88 (50 mg, 0.15 mmol, 1 equiv) and trifluoroacetic acid (51 µL, 0.66 mmol, 4.5 equiv). The reaction mixture was heated to 60° C. for 4 h, cooled. Then partitioned between ethyl acetate (4.5 mL) and 1N sodium hydroxide (2 mL) and stirred for 16 h. The organic layer was collected, and the aqueous layer extracted with ethyl acetate (2×10 mL). The combined organics were dried of sodium sulfate, decanted, and concentrated. The residue was chromatographed (1:1 ethyl acetate/hexane) to produce 123 as a yellow solid (24.5 mg, 39%), mp: 195.0-196.5° C.: $^1$H NMR (300 MHz, CDCl$_3$) δ 8.93 (s, 1H), 7.98-7.92 (m, 1H), 7.75 (d, J=8.7 Hz, 1H), 7.63 (d, J=8.4 Hz, 1H), 7.57 (t, J=7.2 Hz, 1H), 7.48-7.38 (m, 2H), 7.22-7.13 (m, 1H), 3.82 (br s, 2H), 3.13-2.91 (m, 6H); ESI-MS [M+H]$^+$ m/z calcd for C$_{21}$H$_{27}$F$_5$N$_3$O, 422.12; found, 422.4.

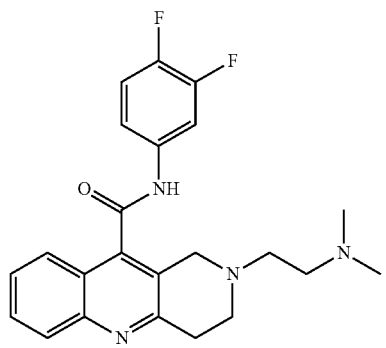 [SMILES: CN(C)CCN1CCc2nc3ccccc3c(C(=O)Nc3ccc(F)c(F)c3)c2C1]

N-(3,4-Difluorophenyl)-2-(2-(dimethylamino)ethyl)-1,2,3,4-tetrahydrobenzo[b][1,6]naphthyridine-10-carboxamide (124)

A solution of amine 88 (35 mg, 0.10 mmol, 1 equiv) in dimethylformamide (1.5 mL) was stirred under an argon atmosphere. A portion of 2-chloro-N,N-dimethylethylamine hydrochloride (14.8 mg, 0.10 mmol, 1 equiv) was added, followed by sodium carbonate (34 mg, 0.32 mmol, 3.1 equiv) and sodium iodide (3 mg, 0.019 mmol, 0.18 equiv). The reaction mixture was heated at 80° C. for 16 h. The reaction was cooled to room temperature and concentrated. The residue was chromatographed (10% methanol in dichloromethane to 6:1.6:0.3 ethyl acetate/methanol/NH$_4$OH(aq)) to produce 124 (3.7 mg, 8.8%): 1H NMR (300 MHz, CD$_3$CN) δ 9.21-9.14 (br s, 1H), 8.01 (dd, 1H, J=8.4, 0.4 Hz), 7.91 (ddd, 1H, J=12.8, 7.4, 2.6 Hz), 7.85 (dd, 1H, J=7.9, 0.6 Hz), 7.75 (ddd, 1H, J=8.5, 6.9, 1.5 Hz), 7.58 (ddd, 1H, J=8.3, 6.6, 1.2 Hz), 7.40-7.37 (m, 1H), 7.35 (app dt, 1H, J=8.8, 1.5 Hz), 3.92-3.88 (br s, 2H), 3.22 (t, 2H, J=6.1 Hz), 2.98 (t, 2H, J=5.9 Hz), 2.69 (t, 2H, J=6.8 Hz), 2.48 (t, 2H, J=6.8 Hz), 2.19 (s, 4H), 2.19-2.18 (app br s, 3H); ESI-MS [M+H]$^+$ m/z calcd for C$_{23}$H$_{25}$F$_2$N$_4$O, 411.19; found, 411.1.

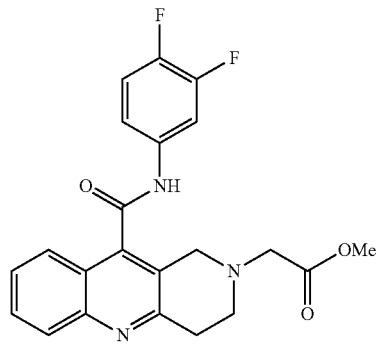 [SMILES: COC(=O)CN1CCc2nc3ccccc3c(C(=O)Nc3ccc(F)c(F)c3)c2C1]

Methyl 2-(10-((3,4-difluorophenyl)carbamoyl)-3,4-dihydrobenzo[b][1,6]naphthyridin-2(1H)-yl)acetate (125)

A solution of secondary amine 88 (50 mg, 0.15 mmol, 1 equiv) in dimethylformamide (490 µL) was stirred under a nitrogen atmosphere. Methyl bromoacetate (15 µL, 0.16 mmol, 1.1 equiv) was added followed by cesium carbonate (53 mg, 0.16 mmol, 1.1 equiv). After 2 h the reaction was filtered, and the filtrate concentrated. The residue was chromatographed (4:1 ethyl acetate/hexane) and the product triturated with ethyl acetate to produce a white solid (41.7 mg, 68%), mp: 142.8-155.9° C.: $^1$H NMR (500 MHz, CD$_3$OD) δ 8.00 (d, J=8.6 Hz, 1H), 7.88 (ddd, J=12.6, 7.3, 2.6 Hz, 1H), 7.84 (d, J=8.4 Hz, 1H), 7.77 (ddd, J=8.5, 6.9, 1.4 Hz, 1H), 7.61 (ddd, J=8.3, 6.9, 1.2 Hz, 1H), 7.39 (dddd, J=8.5, 4.1, 2.6, 1.6 Hz, 1H), 7.29 (dt, J=10.4, 8.9 Hz, 1H), 4.04 (d, J=17.0 Hz, 2H), 3.71 (s, 3H), 3.32-3.28 (m, 4H), 3.16 (s, 1H), 3.10 (s, 1H); $^{13}$C NMR (126 MHz, Methanol-d$_4$) δ 170.77, 165.45, 156.14, 149.84 (dd, J=245.6, 13.3 Hz), 147.08 (dd, J=244.6, 12.8 Hz), 146.24, 140.23, 134.73 (dd, J=8.7, 3.3 Hz), 129.79, 127.38, 127.03, 124.20, 123.87, 122.95, 117.10 (d, J=18.1 Hz), 116.05, 109.37 (d, J=22.0 Hz), 57.35, 51.94, 50.77 (d, J=3.8 Hz), 49.75, 32.39; $^{19}$F NMR (470 MHz, CD$_3$OD) δ −138.55 (ddd, J=21.6, 12.4, 9.2 Hz), −144.45--144.79 (m); ESI-MS [M+H]$^+$ m/z calcd for C$_{22}$H$_{20}$F$_2$N$_3$O$_3$, 412.14; found, 412.2.

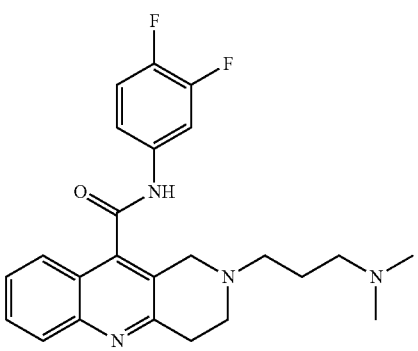 [SMILES: CN(C)CCCN1CCc2nc3ccccc3c(C(=O)Nc3ccc(F)c(F)c3)c2C1]

N-(3,4-Difluorophenyl)-2-(3-(dimethylamino)propyl)-1,2,3,4-tetrahydrobenzo[b][1,6]naphthyridine-10-carboxamide (126)

A solution of amide 110 (17 mg, 0.039 mmol, 1 equiv) in THF (500 μL) was cooled to 0° C. Lithium aluminum hydride (1.9 mg, 0.050 mmol, 1.3 equiv) was added, and the solution stirred for 2.5 h. An additional portion of lithium aluminum hydride (1.9 mg, 1.3 equiv) was added, and the reaction stirred at room temperature for 16 h. The reaction was quenched with 1N sodium hydroxide (400 μL) and water (300 μL), which formed a suspension. After 30 min, the suspension was filtered, and the filtrate concentrated. The residue was chromatographed (6:1.6:0.3 ethyl acetate/methanol/NH$_4$OH(aq)) to produce 126 (4.5 mg, 27%): 1H NMR (400 MHz, ACN-d3) δ 9.76-9.73 (br s, 1H), 7.99 (dd, 1H, J=8.1, 0.7 Hz), 7.95 (ddd, 1H, J=12.7, 7.4, 2.5 Hz), 7.84 (dd, 1H, J=8.2, 0.8 Hz), 7.74 (ddd, 1H, J=8.3, 6.8, 1.4 Hz), 7.57 (ddd, 1H, J=8.2, 6.8, 1.2 Hz), 7.46 (dddd, 1H, J=9.0, 4.0, 2.7, 1.8 Hz), 7.32 (dt, 1H, J=10.6, 9.0 Hz), 4.00-3.81 (br s, 2H), 3.23 (t, 2H, J=5.6 Hz), 3.13 (t, 2H, J=6.8 Hz), 2.99 (t, 2H, J=6.2 Hz), 2.73 (s, 6H), 2.71 (t, 2H, J=6.1 Hz); ESI-MS [M+H]$^+$ m/z calcd for C$_{24}$H$_{27}$F$_2$N$_4$O, 425.20; found, 425.3.

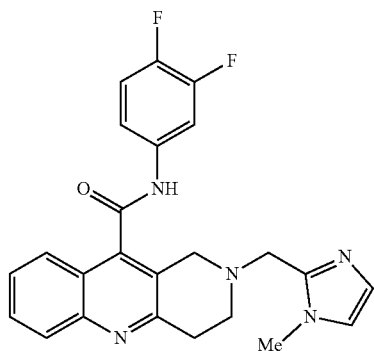 [SMILES: Cn1ccnc1CN1CCc2nc3ccccc3c(C(=O)Nc3ccc(F)c(F)c3)c2C1]

N-(3,4-Difluorophenyl)-2-((1-methyl-1H-imidazol-2-yl)methyl)-1,2,3,4-tetrahydrobenzo[b][1,6]naphthyridine-10-carboxamide (127)

The TBN was prepared from amine 88 (8.5 mg, 0.077 mmol, 1 equiv) and 1-methyl-2-imidazole-carboxaldehyde (8.5 mg, 0.077 mmol, 1.6 equiv) by following the procedure for 95. Chromatography with 19:1 dichloromethane/methanol afforded the product as a yellow solid (10.9 mg, 51.8% yield), mp (decomposition): 207.5-216.6° C.: $^1$H NMR (400 MHz, CDCl$_3$) δ 9.90 (s, 1H), 7.98 (d, 1H, J=8.4 Hz), 7.85 (ddd, 1H, J=12.1, 7.3, 2.6 Hz), 7.82 (dd, 1H, J=8.4, 0.7 Hz), 7.67 (ddd, 1H, J=8.4, 6.9, 1.4 Hz), 7.50 (ddd, 1H, J=8.2, 6.9, 1.2 Hz), 7.39 (dddd, 1H, J=8.7, 4.1, 2.5, 1.2 Hz), 7.15 (dt, 1H, J=9.9, 8.8 Hz), 6.78 (d, 1H, J=1.3 Hz), 6.71 (d, 1H, J=1.3 Hz), 3.89 (s, 2H), 3.72 (s, 2H), 3.67 (2, 3H), 3.16 (t, 2H, J=5.9 Hz), 3.06 (t, 2H, J=5.9 Hz); ESI-MS [M+H]$^+$ calcd for C$_{24}$H$_{21}$F$_2$N$_5$O, 434.46; found, 434.7

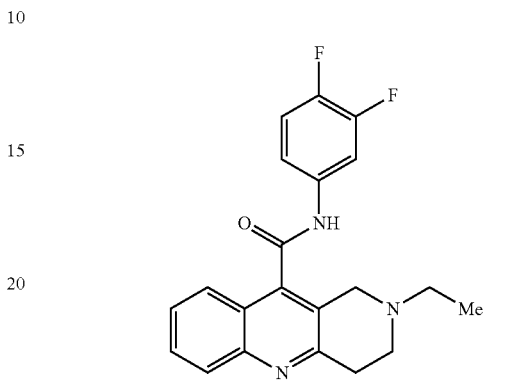

N-(3,4-Difluorophenyl)-2-ethyl-1,2,3,4-tetrahydrobenzo[b][1,6]naphthyridine-10-carboxamide (128)

A solution of acid 133 (100 mg, 0.342 mmol, 1 equiv) in acetonitrile (2.1 mL) was stirred at room temperature. 3,4-Difluoroaniline (51 μL, 0.5 mmol, 1.5 equiv) was added followed by phosphorous oxychloride (47 μL, 0.5 mmol, 1.5 equiv), which caused the reaction to become cloudy. The suspension was heated at reflux for 16 h. The reaction mixture was cooled and concentrated, and the residue was partitioned between ethyl acetate (20 mL) and saturated sodium bicarbonate (20 mL). The organic layer was collected, and the aqueous layer extracted once more with ethyl acetate (20 mL). The organic extracts were combined, dried over sodium sulfate, and concentrated. The residue was chromatographed (5% methanol in dichloromethane) to afford the hydrochloride salt of 128 as an orange solid (11 mg, 8.7%), mp (decomposition): 216.5-219.1° C. $^1$H NMR (500 MHz, CD$_3$OD) δ 8.00 (d, J=8.6 Hz, 1H), 7.89 (ddd, J=12.6, 7.3, 2.6 Hz, 1H), 7.85 (d, J=8.5 Hz, 1H), 7.77 (ddd, J=8.5, 6.9, 1.4 Hz, 1H), 7.61 (ddd, J=8.3, 6.8, 1.2 Hz, 1H), 7.40 (dddd, J=9.0, 4.0, 2.5, 1.6 Hz, 1H), 7.30 (dt, J=10.4, 8.9 Hz, 1H), 3.91 (br d, J=14.4 Hz, 1H), 3.83 (br d, J=14.2 Hz, 1H), 3.30-3.28 (m, 2H), 3.01 (app q, J=6.0 Hz, 2H), 2.69 (q, J=7.2 Hz, 2H), 1.19 (t, J=7.2 Hz, 3H); ESI-MS [M+H]$^+$ m/z calcd for C$_{21}$H$_{20}$F$_2$N$_3$O, 368.15; found, 368.4.

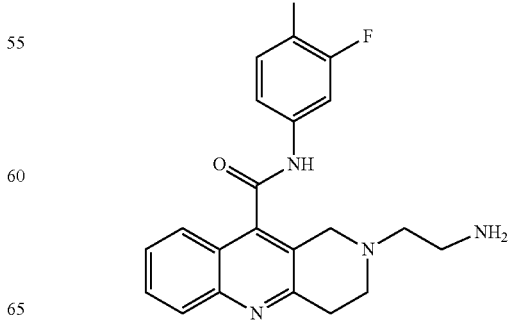

2-(2-Aminoethyl)-N-(3,4-difluorophenyl)-1,2,3,4-tetrahydrobenzo[b][1,6]naphthyridine-10-carboxamide (129)

A suspension of TBN 121 (25 mg, 0.049 mmol, 1 equiv) in ethanol (1 mL) was stirred at room temperature. Hydrazine hydrate (2.6 μL, 0.054 mmol, 1.1 equiv) was added and the reaction heated at reflux. After 7 h, the reaction was cooled and stirred at room temperature for an additional 16 h. The reaction was filtered, and the filtrate concentrated. The residue was chromatographed (6:1.6:0.3 ethyl acetate/methanol/NH$_4$OH(aq)) to produce 129 as a yellow oil (7.9 mg, 42%): $^1$H NMR (500 MHz, CDCl$_3$) δ 8.99 (s, 1H), 7.90 (d, J=8.1 Hz, 1H), 7.93-7.84 (m, 1H), 7.76 (d, J=8.4 Hz, 1H), 7.62 (dd, J=8.6, 6.7 Hz, 1H), 7.47 (t, J=7.6 Hz, 1H), 7.41-7.36 (m, 1H), 7.17 (q, J=9.1 Hz, 1H), 3.79 (s, 2H), 3.15 (t, J=6.2 Hz, 2H), 2.84-2.77 (m, 6H), 2.58 (t, J=5.8 Hz, 2H).

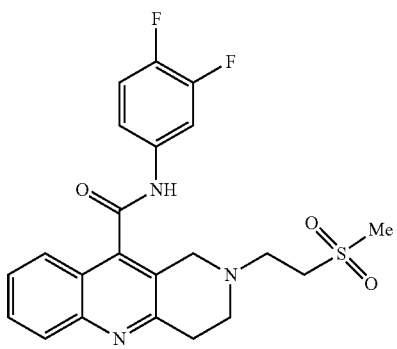 [SMILES: CS(=O)(=O)CCN1CCc2nc3ccccc3c(C(=O)Nc3ccc(F)c(F)c3)c2C1]

N-(3,4-Difluorophenyl)-2-(2-(methylsulfonyl)ethyl)-1,2,3,4-tetrahydrobenzo[b][1,6]naphthyridine-10-carboxamide (130)

A suspension of amine 88 (50 mg, 0.15 mmol, 1 equiv) in ethanol (1.7 mL) was stirred at room temperature. Methyl vinyl sulfone (19 μL, 0.22 mmol, 1.4 equiv) was added and the reaction heated at 73° C. The suspension cleared after 30 min. After an additional 2.5 h of heating, a solid precipitated and the reaction was cooled. Isolation of the solid via filtration produced 130 as a pure white solid (24 mg, 35%), mp: 241.2-242.6° C.: $^1$H NMR (500 MHz, CDCl$_3$) δ 8.56 (s, 1H), 7.96 (d, J=8.3 Hz, 1H), 7.95-7.89 (m, 1H), 7.83 (d, J=8.1 Hz, 1H), 7.69 (t, J=7.8 Hz, 1H), 7.55 (t, J=7.6 Hz, 1H), 7.40-7.35 (m, 1H), 7.26-7.16 (m, 1H), 3.91 (s, 2H), 3.29-3.18 (m, 4H), 3.11 (t, J=6.4 Hz, 2H), 3.00-2.94 (m, 5H); $^{19}$F NMR (470 MHz, CDCl$_3$) δ−134.50−−134.96 (m), −140.74−−141.07 (m); ESI-MS [M+H]$^+$ m/z calcd for C$_{22}$H$_{22}$F$_2$N$_3$O$_3$S$_1$, 446.13; found, 446.6.

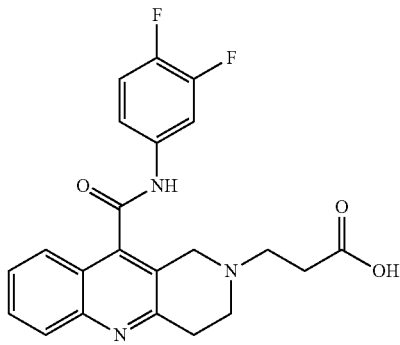 [SMILES: O=C(O)CCN1CCc2nc3ccccc3c(C(=O)Nc3ccc(F)c(F)c3)c2C1]

3-(10-((3,4-Difluorophenyl)carbamoyl)-3,4-dihydrobenzo[b][1,6]naphthyridin-2(1H)-yl)propanoic acid (131)

A solution of amide 109 (80 mg, 0.19 mmol, 1 equiv) in 3:8 methanol/dichloromethane (1.6 mL) was stirred at room temperature. A solution of aqueous lithium hydroxide (3 M, 0.6 mL, 10 equiv) was added, and the mixture stirred for 1.5 h. Ten drops of 20% citric acid solution was added. The reaction mixture was partitioned between ethyl acetate (20 mL) and 1 M sodium hydroxide (20 mL). The aqueous layer was collected and acidified with 20% citric acid solution to a pH of 5 (pH paper). The aqueous layer was extracted with ethyl acetate, and the resulting organic extract condensed to afford 131 (54.9 mg, 71%): 1H NMR (400 MHz, CD$_3$OD) δ 8.01 (d, J=8.7 Hz, 1H), 7.90 (ddd, J=12.4, 7.3, 2.5 Hz, 1H), 7.86 (d, J=9.0 Hz, 1H), 7.78 (ddd, J=8.4, 6.9, 1.4 Hz, 1H), 7.62 (ddd, J=8.3, 6.9, 1.2 Hz, 1H), 7.43-7.38 (m, 1H), 7.30 (dt, J=10.4, 8.8 Hz, 1H), 4.04 (br s, 2H), 3.34-3.31 (m, 2H), 3.22-3.12 (m, 2H), 3.03 (t, J=6.9 Hz, 2H), 2.61 (t, J=6.9 Hz, 2H); ESI-MS [M+H]$^+$ m/z calcd for C$_{22}$H$_{20}$F$_2$N$_3$O$_3$, 412.14; found, 414.0 (extra mass due to deuterium exchange with CD$_3$OOD).

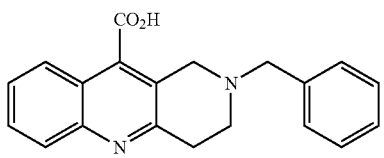 [SMILES: O=C(O)c1c2c(nc3ccccc13)CCN(Cc1ccccc1)C2]

2-Benzyl-1,2,3,4-tetrahydrobenzo[b][1,6]naphthyridine-10-carboxylic acid (132)

A solution of potassium hydroxide (2.83 g, 50.4 mmol, 10 equiv) in 50% aqueous dioxane (10 mL) was stirred at room temperature. Isatin (750 mg, 5 mmol, 1 equiv) was added which turned the solution black in color. After twenty min the solution had lightened to a yellow color. 1-Benzyl-4-piperidinone (2.2 mL, 12 mmol, 2.4 equiv) was added. The reaction mixture was heated at reflux and allowed to stir at this temperature for 16 h. The reaction was cooled, and then was brought to a pH of approximately 6 by adding aq hydrochloric acid (37% w/w, 4.1 mL, 10 equiv). The reaction was concentrated, and the residue suspended in ethanol (10 mL) The suspension was filtered, and the filtrate was acidified with aq hydrochloric acid (37% w/w, 1 mL) to a pH of one. The filtrate was refrigerated for 16 h, whereupon the product precipitated. The suspension was filtered, and the light-brown solid was collected (547 mg, 34%), mp (decomposition): 216.1-225.0° C.: $^1$H NMR (300 MHz, DMSO-$d_6$) δ 12.20 (br s, 1H), 8.03 (d, J=8.4 Hz, 1H), 7.97 (dd, J=8.5, 1.3 Hz, 1H), 7.83 (ddd, J=8.4, 6.8, 1.4 Hz, 1H), 7.77-7.63 (m, 3H), 7.54-7.42 (m, 3H), 4.11-3.19 (m, 8H); $^{13}$C NMR (75 MHz, DMSO-$d_6$) δ 167.46, 153.47, 146.89, 138.20, 131.88, 131.04, 130.21, 130.05, 129.31, 128.86, 128.11, 125.37, 122.40, 119.35, 58.62, 50.22, 48.06, 29.60; ESI-MS [M–H]$^-$ m/z calcd for $C_{20}H_{17}N_2O_2$, 317.14; found, 317.2.

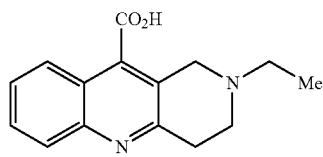 [SMILES: CCN1CCc2nc3ccccc3c(C(=O)O)c2C1]

2-Ethyl-1,2,3,4-tetrahydrobenzo[b][1,6]naphthyridine-10-carboxylic acid (133)

A solution of potassium hydroxide (449 mg, 8 mmol, 3.2 equiv) in a 4:1 mixture of ethanol and water (5 mL) was stirred at room temperature. Isatin (386 mg, 2.5 mmol, 1 equiv) was added, which turned the solution black in color. After 15 min the solution had lightened to a yellow color. 1-Ethyl-4-piperidinone (370 μL, 2.75 mmol, 1.1 equiv) was added. The reaction mixture was heated at reflux for 16 h. The reaction was cooled and then was brought to a pH of approximately five with acetic acid (1.5 mL), causing a solid to precipitate. The suspension was filtered, and the filtrate was acidified further with concentrated hydrochloric acid (33% w/w, 1 mL), which resulted in further precipitation. The suspension was filtered, and the filtrate was concentrated. The residue was chromatographed (2% to 30% methanol in dichloromethane) to give 133 as a white solid (136 mg, 21%), mp (decomposition): 262.3-266.9° C.: $^1$H NMR (500 MHz, $D_2O$) δ 7.93 (dt, J=8.8, 0.7 Hz, 1H), 7.90-7.87 (m, 1H), 7.87-7.83 (m, 1H), 7.66 (ddd, J=8.3, 6.9, 1.3 Hz, 1H), 4.55-4.46 (m, 2H), 3.75 (br s, 2H), 3.48 (t, J=6.4 Hz, 2H), 3.37 (q, J=7.3 Hz, 2H), 1.34 (t, J=7.3 Hz, 3H); ESI-MS [M–H]$^-$ m/z calcd for $C_{15}H_{15}N_2O_2$, 255.12; found, 255.2.

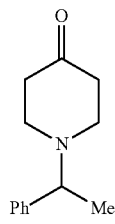 [SMILES: CC(c1ccccc1)N1CCC(=O)CC1]

1-(1-Phenylethyl)piperidin-4-one (R and S)

A solution of potassium carbonate (271 mg, 2.0 mmol, 2.2 equiv) in water (750 μL) was stirred at room temperature. 1-Phenylethylamine (R or S, 113 μL, 0.89 mmol, 1 equiv) was added as a solution in ethanol (3.2 mL). The reaction mixture was heated at reflux, and 1,1-dimethyl-4-oxo-piperidinium (250 mg, 0.98 mmol, 1.1 equiv) was added as a solution in water (750 μL). After 5 h, the reaction mixture was cooled, and additional water was added, whereupon a suspension to formed. The reaction was concentrated partially to remove ethanol and extracted twice with ethyl ether. The combined organic extracts were dried over sodium sulfate, decanted, and concentrated to furnish each enantiomer as a yellow oil.

(134, R). (111 mg, 61%): $^1$H NMR (500 MHz, CDCl$_3$) δ 7.38-7.22 (m, 6H), 3.62 (q, J=6.8 Hz, 1H), 2.82-2.67 (m, 4H), 2.42 (t, J=6.2 Hz, 3H), 1.42 (d, J=6.7 Hz, 3H).

(135, S). (206 mg, 51%): $^1$H NMR (500 MHz, CDCl$_3$) δ 7.38-7.23 (m, 7H), 3.63 (q, J=6.8 Hz, 1H), 2.84-2.67 (m, 4H), 2.42 (t, J=6.2 Hz, 3H), 1.42 (d, J=6.8 Hz, 3H).

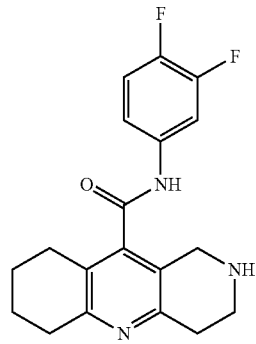 [SMILES: O=C(Nc1ccc(F)c(F)c1)c1c2c(nc3c1CNCC3)CCCC2]

N-(3,4-Difluorophenyl)-1,2,3,4,6,7,8,9-octahydrobenzo[b][1,6]naphthyridine-10-carboxamide (136)

A solution of protected amine 87 (300 mg, 0.68 mmol, 1 equiv) in trifluoroacetic acid (4.5 mL) was stirred under hydrogen. Platinum dioxide (23 mg, 0.096 mmol, 0.14 equiv) was added and the reaction was left to stir at room temperature. After 9 h, the reaction was filtered, and the filtrate concentrated. The residue was partitioned between dichloromethane (50 mL) and saturated sodium bicarbonate (50 mL), which formed a suspension in the organic layer. The organic layer was collected, and the aqueous layer washed with dichloromethane (2×50 mL). Methanol was added to the organic extracts until the suspension cleared. The combined organic extracts were dried over sodium sulfate, decanted, and concentrated. The residue was chromatographed (20% methanol in dichloromethane), and the resulting solid partitioned between ethyl acetate (20 mL) and 1N sodium hydroxide (20 mL). The organic layer was dried over sodium sulfate, decanted, and concentrated to afford 136 (131.4 mg, 56%): 1H NMR (500 MHz, CDCl$_3$) δ 8.22 (s, 1H), 7.72 (ddd, J=11.9, 7.1, 2.6 Hz, 1H), 7.24-7.19 (m, 1H), 7.13 (dt, J=9.6, 8.6 Hz, 1H), 4.01 (s, 2H), 3.21 (t, J=6.2 Hz, 2H), 3.12 (br s, 2H), 2.94 (t, J=6.1 Hz, 2H), 2.87 (t, J=6.4 Hz, 2H), 2.74 (t, J=6.3 Hz, 2H), 1.91-1.82 (m, 2H), 1.82-1.73 (m, 2H); $^{19}$F NMR (376 MHz, CDCl$_3$) δ−75.73 (trifluoroacetic acid), −134.91 (ddd, J=20.7, 11.8, 8.2 Hz), −141.22 (dddd, J=21.1, 10.5, 7.0, 3.9 Hz); ESI-MS [M+H]$^+$ m/z calcd for $C_{19}H_{20}F_2N_3O$, 344.15; found, 344.0.

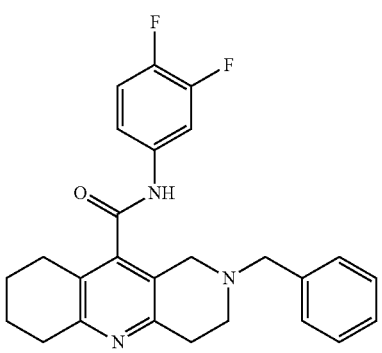 [SMILES: O=C(Nc1ccc(F)c(F)c1)c1c2c(nc3c1CN(Cc1ccccc1)CC3)CCCC2]

2-Benzyl-N-(3,4-difluorophenyl)-1,2,3,4,6,7,8,9-octahydrobenzo[b][1,6]naphthyridine-10-carboxamide (137)

A solution of amine 136 (9.4 mg, 0.027 mmol, 1 equiv) in dichloroethane (135 μL) is stirred at room temperature. benzaldehyde (3.4 μL, 0.033 mmol, 1.2 equiv) is added followed by sodium triacetoxyborohydride (8 mg, 0.038 mmol, 1.4 equiv). The reaction is monitored by TLC to check for the disappearance of starting material. The reaction was quenched with saturated sodium bicarbonate (5 mL) and extracted with dichloromethane (2×10 mL). The organics are combined, dried over sodium sulfate, concentrated, and chromatographed (3% methanol in dichloromethane) to produce 137 with 18% oxidized impurity (12.3 mg, >95%): 1H NMR (400 MHz, CDCl$_3$) δ 8.77 (br s, 1H), 7.69 (ddd, J=12.0, 7.2, 2.6 Hz, 1H), 7.46-7.42 (m, 2H), 7.37-7.31 (m, 3H), 7.25-7.20 (m, 1H), 7.12 (dt, J=10.0, 8.8 Hz, 1H), 3.95 (s, 2H), 3.92 (s, 2H), 3.20-3.05 (m, 4H), 2.90 (t, J=6.4 Hz, 2H), 2.78 (d, J=6.6 Hz, 2H), 1.94-1.82 (m, 2H), 1.84-1.76 (m, 2H). $^{19}$F NMR (376 MHz, CDCl$_3$) δ−76.00 (TFA), −135.40--135.51 (m), −141.62--141.67 (m); ESI-MS [M+H]$^+$ m/z calcd for C$_{26}$H$_{26}$F$_2$N$_3$O, 434.20; found, 434.3.

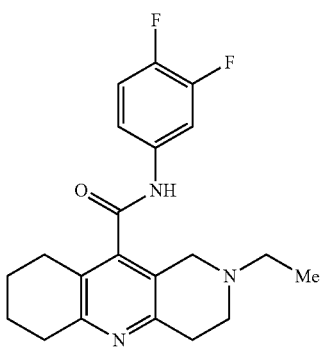 [SMILES: CCN1CCc2nc3c(c(C(=O)Nc4ccc(F)c(F)c4)c2C1)CCCC3]

N-(3,4-Difluorophenyl)-2-ethyl-1,2,3,4,6,7,8,9-octahydrobenzo[b][1,6]naphthyridine-10-carboxamide (138)

A solution of acid 141 (100 mg, 0.384 mmol, 1 equiv) in acetonitrile (1.3 mL) was stirred at room temperature. 3,4-difluoroaniline (57 μL, 0.576 mmol, 1.5 equiv) was added followed by phosphorous oxychloride (39 μL, 0.422 mmol, 1.1 equiv) causing the reaction to become cloudy. The suspension was heated at reflux for 16 h. The reaction was cooled to room temperature, concentrated, and the residue partitioned between ethyl acetate (20 mL) and saturated sodium bicarbonate (20 mL). The organic layer was collected, and the aqueous layer extracted once more with ethyl acetate (20 mL). The organic extracts were combined, dried over sodium sulfate, and concentrated. The residue was chromatographed (5% methanol in dichloromethane) to produce 138 (22.3 mg, 16%): $^1$H NMR (500 MHz, CDCl$_3$) δ 8.45 (s, 1H), 7.74 (ddd, J=11.9, 7.1, 2.5 Hz, 1H), 7.22 (ddt, J=8.2, 3.9, 1.7 Hz, 1H), 7.12 (dt, J=9.6, 8.6 Hz, 1H), 3.64 (s, 2H), 3.01 (br t, J=6.1 Hz, 2H), 2.88-2.80 (m, 4H), 2.73 (t, J=6.2 Hz, 2H), 2.61 (q, J=7.1 Hz, 2H), 1.89 (s, 0.5H), 1.87-1.81 (m, 2H), 1.80-1.74 (m, 2H), 1.14 (t, J=7.1 Hz, 3H); $^{13}$C NMR (126 MHz, CDCl$_3$) δ 165.77, 156.39, 151.78, 150.12 (dd, J=247.8, 13.3 Hz), 147.32 (dd, J=246.2, 12.6 Hz), 141.95, 133.93 (dd, J=8.6, 3.4 Hz), 125.46, 122.07, 117.39 (d, J=18.2 Hz), 115.61 (dd, J=6.0, 3.5 Hz), 109.80 (d, J=21.8 Hz), 52.06, 51.88, 49.84, 32.57, 31.80, 25.54, 22.66, 22.31, 11.75; $^{19}$F NMR (500 MHz, CDCl$_3$) δ−75.84 (trifluoroacetic acid), −135.21 (ddd, J=21.0, 12.0, 8.6 Hz), −141.56--141.70 (m); ESI-MS [M+H]$^+$ m/z calcd for C$_{21}$H$_{24}$F$_2$N$_3$O, 372.18; found, 372.2.

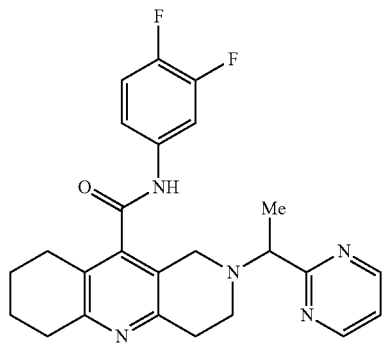

N-(3,4-Difluorophenyl)-2-(1-(pyrimidin-2-yl)ethyl)-1,2,3,4,6,7,8,9-octahydrobenzo[b][1,6]naphthyridine-10-carboxamide (139)

A solution of amine 136 (34 mg, 0.1 mmol, 1 equiv) in dichloroethane (1 mL) was stirred at under a nitrogen atmosphere with 4 Å molecular sieves. 2-acetylpyrimidine (16 mg, 0.13 mmol, 1.3 equiv) was added followed by sodium triacetoxyborohydride (34 mg, 0.16 mmol, 1.6 equiv). After 16 h, saturated sodium bicarbonate (20 mL) was added, and the solution extracted with ethyl acetate (3×20 mL). The organic layers were combined, dried over sodium sulfate, decanted, and concentrated. The residue was chromatographed (10% methanol in dichloromethane) to produce 139 as a yellow solid (10.9 mg, 24%): 1H NMR (500 MHz, CDCl$_3$) δ 8.66 (d, J=4.9 Hz, 2H), 7.92 (br s, 1H), 7.68 (ddd, J=12.0, 7.3, 2.2 Hz, 1H), 7.17-7.10 (m, 3H), 4.11 (q, J=6.8 Hz, 1H), 3.94 (d, J=15.2 Hz, 1H), 3.78 (d, J=15.2 Hz, 1H), 3.08-3.00 (m, 2H), 3.00-2.94 (m, 2H), 2.86 (t, J=6.4 Hz, 2H), 2.73 (t, J=6.3 Hz, 2H), 1.90-1.81 (m, 2H), 1.81-1.72 (m, 2H), 1.55 (d, J=6.8 Hz, 3H); $^{19}$F NMR (470 MHz, CDCl$_3$) δ−135.10 (ddd, J=19.6, 11.9, 7.2 Hz), −141.30--141.66 (m); ESI-MS [M−H$_2$+H]$^+$ m/z calcd for C$_{25}$H$_{24}$F$_2$N$_5$O, 448.19; found 448.2.

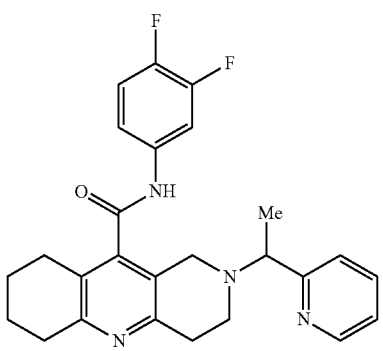 [SMILES: CC(c1ncccn1)N1CCc2nc3c(c(C(=O)Nc4ccc(F)c(F)c4)c2C1)CCCC3]

N-(3,4-Difluorophenyl)-2-(1-(pyridin-2-yl)ethyl)-1,2,3,4,6,7,8,9-octahydrobenzo[b][1,6]naphthyridine-10-carboxamide (140)

A solution of amine 136 (50 mg, 0.15 mmol, 1 equiv) in dichloroethane (1 mL) was stirred under a nitrogen atmosphere with 4 Å molecular sieves. 2-Acetylpyridine (21 µL, 0.19 mmol, 1.3 equiv) was added and the reaction heated at 50° C. for 10 min. After cooling to room temperature, sodium triacetoxyborohydride (69 mg, 0.33 mmol, 2.2 equiv) was added and the mixture stirred for 48 h. The reaction was quenched with saturated sodium bicarbonate (20 mL) and extracted with ethyl acetate (3×20 mL). The organic layers were combined, dried over sodium sulfate, decanted, and concentrated. The residue was chromatographed (8% methanol in dichloromethane) to produce the product. (26.3 mg, 40%): 1H NMR (500 MHz, CDCl$_3$) δ 8.95 (s, 1H), 8.40-8.37 (m, 1H), 7.64-7.52 (m, 2H), 7.36 (d, J=8.0 Hz, 1H), 7.17-7.04 (m, 3H), 3.75 (q, J=6.0 Hz, 1H), 3.69 (d, J=15.4 Hz, 1H), 3.62 (d, J=15.5 Hz, 1H), 2.96 (br s, 2H), 2.90-2.87 (m, 1H), 2.84 (t, J=6.2 Hz, 2H), 2.77-2.68 (m, 4H), 1.90-1.79 (m, 2H), 1.79-1.70 (m, 2H), 1.43 (app dd, J=6.7, 2.0 Hz, 3H); ESI-MS [M+H]$^+$ m/z calcd for C$_{26}$H$_{27}$F$_2$N$_4$O, 449.21; found, 449.3.

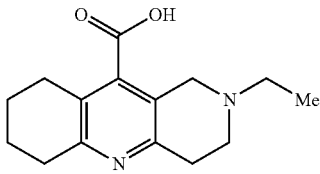 [SMILES: CCN1CCc2nc3c(c(C(=O)O)c2C1)CCCC3]

2-Ethyl-1,2,3,4,6,7,8,9-octahydrobenzo[b][1,6]naphthyridine-10-carboxylic Acid (141)

A solution of acid 133 (112 mg, 0.436 mmol, 1 equiv) in trifluoroacetic acid (1 mL) was stirred under hydrogen. A suspension of platinum dioxide (40 mg, 0.174 mmol, 0.4 equiv) in trifluoroacetic acid (500 µL) was added via syringe. The reaction must be monitored by TLC (10% methanol in dichloromethane, ninhydrin stain) to prevent over-reduction. The reaction was stirred for 2.5 hours, then filtered. The filtrate was concentrated, and the residue dissolved in water. Saturated sodium bicarbonate was added until the pH of the solution was approximately six. The aqueous mixture was concentrated, and the residue rinsed with acetone. The acetone was collected and concentrated producing 141 as a white solid (100 mg, 78%): 1H NMR (500 MHz, CD$_3$OD) δ 4.23 (s, 2H), 3.52 (t, J=6.4 Hz, 2H), 3.25 (q, J=7.3 Hz, 2H), 3.16 (t, J=6.3 Hz, 2H), 2.85 (t, J=6.6 Hz, 2H), 2.79 (t, J=6.6 Hz, 2H), 1.92-1.85 (m, 2H), 1.84-1.77 (m, 2H), 1.38 (t, J=7.3 Hz, 3H); ESI-MS [M+H]$^+$ m/z calcd for C$_{15}$H$_{21}$N$_2$O$_2$, 261.15; found, 261.4.

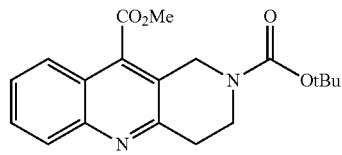 [SMILES: COC(=O)c1c2c(nc3ccccc13)CCN(C(=O)OC(C)(C)C)C2]

2-(tert-Butyl) 10-methyl 3,4-dihydrobenzo[b][1,6]naphthyridine-2,10(1H)-dicarboxylate (142)

A suspension of acid 85 (1.0 g, 3.0 mmol, 1 equiv), in 5:1 THF/DMF (15.2 mL) was prepared in a thick-walled glass tube under a nitrogen atmosphere. Potassium carbonate (337 mg, 2.4 mmol, 0.8 equiv) was added, followed by methyl iodide (835 µL, 13.4 mmol, 4.4 equiv). After sealing the tube, the reaction mixture was heated at 55° C. for 16 h. The orange solution was cooled to room temperature, quenched with water (15 mL), and extracted with ethyl ether (3×15 mL). The organic extracts are combined, dried over magnesium sulfate, filtered, and concentrated. Hexanes (15 mL) was added, and the mixture was brought to a boil. The solvent was collected, and the residue was re-subjected to boiling hexanes (2×15 mL), leaving insoluble impurities. The combined hexane extract was concentrated to afford a brown semi-solid (804 mg, 77%): 1H NMR (500 MHz, CDCl$_3$) δ 8.04 (d, J=8.4 Hz, 1H), 7.81 (d, J=8.4 Hz, 1H), 7.70 (ddd, J=8.4, 6.9, 1.4 Hz, 1H), 7.54 (ddd, J=8.3, 6.9, 1.2 Hz, 1H), 4.79 (s, 2H), 4.07 (s, 3H), 3.83 (t, J=6.1 Hz, 2H), 3.24 (t, J=6.1 Hz, 2H), 1.49 (s, 9H); ESI-MS [M+H]$^+$ m/z calcd for C$_{19}$H$_{23}$N$_2$O$_4$, 343.16; found, 343.0.

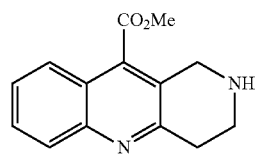

Methyl 1,2,3,4-tetrahydrobenzo[b][1,6]naphthyridine-10-carboxylate (143)

Method A: A solution of ester 142 (804 mg, 2.35 mmol, 1 equiv) in dichloromethane (20 mL) is stirred at room temperature. Trifluoroacetic acid (10 mL) is added, and the reaction is stirred for 1 h. The reaction is concentrated to partial dryness and the residue suspended in toluene. The suspension is concentrated to dryness to give the trifluoroacetic acid salt of 143 with excess trifluoroacetic acid. The crude salt is used without further purification (906 mg, >95%): 1H NMR (500 MHz, CDCl$_3$) δ 8.01 (d, J=8.6 Hz, 1H), 7.76 (d, J=8.3 Hz, 1H), 7.68 (ddd, J=8.4, 6.9, 1.4 Hz, 1H), 7.51 (ddd, J=8.3, 6.8, 1.2 Hz, 1H), 4.21 (s, 2H), 4.05 (s, 3H), 3.33 (t, J=6.2 Hz, 2H), 3.20 (t, J=6.1 Hz, 2H), 1.96 (br s, 5H); ESI-MS [M+H]$^+$ m/z calcd for C$_{14}$H$_{15}$N$_2$O$_2$, 243.11; found, 243.2.

Method B: A solution of ester 142 (381 mg, 1.1 mmol, 1 equiv) in dichloromethane (1 mL) is stirred at room temperature. Hydrochloric acid (4 M in dioxane, 4.5 mL, 18 mmol, 16.4 equiv) is added, and the reaction is stirred for 1.5 h. The reaction is concentrated to dryness and the residue is rinsed with ethyl acetate four times producing the hydrochloride of 143 (130 mg, >95%). A sample (43 mg) was dissolved in a mixture of methanol (1.6 mL) and sodium carbonate (22 mg). After 3 days, the mixture was partitioned between ethyl acetate and water. The organic layer was concentrated, and the resulting solid used for NMR: 1H NMR (400 MHz, CDCl$_3$) δ 7.98 (d, J=8.5 Hz, 1H), 7.74 (d, J=8.4 Hz, 1H), 7.64 (t, J=7.1 Hz, 1H), 7.48 (t, J=7.6 Hz, 1H), 4.17 (s, 2H), 4.02 (s, 3H), 3.29 (s, 1H), 3.15 (br t, J=6.0 Hz, 2H), 2.19 (br s, 1H).

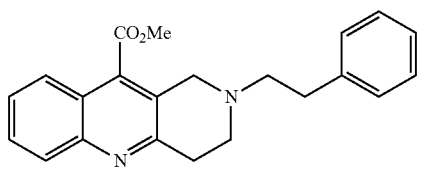 [SMILES: COC(=O)c1c2c(nc3ccccc13)CCN(CCc1ccccc1)C2]

Methyl 1,2,3,4-tetrahydrobenzo[b][1,6]naphthyridine-10-carboxylate (144)

A suspension of the hydrochloride salt of amine 143 (370 mg, 1.33 mmol) in dichloromethane (4.5 mL) was stirred at room temperature. Triethylamine (185 µL, 1.33 mmol, 1 equiv) was added followed by phenylacetaldehyde (187 µL, 1.6 mmol, 1.2 equiv). The solution is stirred at room temperature for 1 h then sodium triacetoxyborohydride (564 mg, 2.66 mmol, 2 equiv) was added. After stirring for an additional 16 h, the reaction was partitioned between water (20 mL) and ethyl acetate (20 mL). The organic layer was collected, and the aqueous layer extracted once more with ethyl acetate. The organic layers were combined, dried over sodium sulfate, decanted, and concentrated. The residue was chromatographed (1:1 ethyl acetate/hexane) to produce 144 as a white solid (328 mg, 71%), mp: 88.9-89.6° C.: 1H NMR (500 MHz, CDCl$_3$) δ 8.02 (d, J=8.3 Hz, 1H), 7.76 (d, J=8.6 Hz, 1H), 7.68 (ddd, J=8.4, 6.9, 1.4 Hz, 1H), 7.51 (ddd, J=8.3, 6.9, 1.3 Hz, 1H), 7.33-7.28 (m, 2H), 7.27-7.20 (m, 3H), 4.05 (s, 3H), 3.89 (s, 2H), 3.32 (t, J=6.1 Hz, 2H), 3.03 (t, J=6.1 Hz, 2H), 2.96-2.91 (m, 2H), 2.89-2.84 (m, 2H); $^{13}$C NMR (126 MHz, CDCl$_3$) δ 167.50, 156.46, 146.80, 139.96, 135.62, 129.38, 128.88, 128.87, 128.69, 128.46, 126.82, 126.19, 124.44, 122.77, 59.67, 53.94, 52.60, 50.24, 33.93, 33.41; ESI-MS [M+H]$^+$ m/z calcd for C$_{22}$H$_{23}$N$_2$O$_2$, 347.17; found, 347.3.

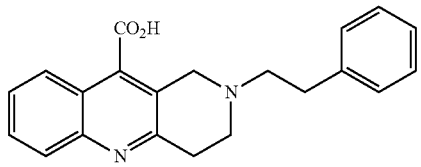 [SMILES: O=C(O)c1c2c(nc3ccccc13)CCN(CCc1ccccc1)C2]

2-Phenethyl-1,2,3,4-tetrahydrobenzo[b][1,6]naphthyridine-10-carboxylic Acid (145)

A solution of ester 144 (328 mg, 0.95 mmol, 1 equiv) in methanol (6 mL) was stirred at room temperature. A solution of 4.75 M potassium hydroxide (4 mL, 19 mmol, 20 equiv) was added forming a suspension. An additional 2.5 mL of methanol was added, which cleared the suspension. The solution was stirred for 16 h then partially concentrated to 4 mL. Aqueous hydrochloric acid (1N, 30 mL) was added bring the pH to 4.7 causing a solid to form. The suspension was filtered, and the solid rinsed with cold water to produce 145 as a yellow solid (279 mg, 88%), mp (decomposition): 220.0-230.0; $^1$H NMR (500 MHz, CD$_3$CO$_2$D) δ 8.14 (d, J=8.3 Hz, 1H), 8.03 (d, J=8.6 Hz, 1H), 7.83 (ddd, J=8.5, 6.9, 1.3 Hz, 1H), 7.67 (ddd, J=8.2, 6.9, 1.2 Hz, 1H), 7.35 (d, J=2.1 Hz, 1H), 7.32-7.24 (m, 1H), 4.93 (s, 2H), 3.91 (app d, J=6.0 Hz, 2H), 3.73-3.60 (m, 3H), 3.33-3.22 (m, 2H), 2.04 (app p, J=2.2 Hz, 4H); $^{13}$C NMR (126 MHz, CD$_3$CO$_2$D) δ170.52, 151.25, 147.27, 143.71, 135.91, 132.15, 128.77, 128.75, 128.18, 127.13, 126.26, 124.72, 122.77, 117.20, 57.58, 51.31, 48.98, 30.09; ESI-MS [M–H]$^-$ m/z calcd for C$_{21}$H$_{19}$N$_2$O$_2$, 331.15; found, 331.3.

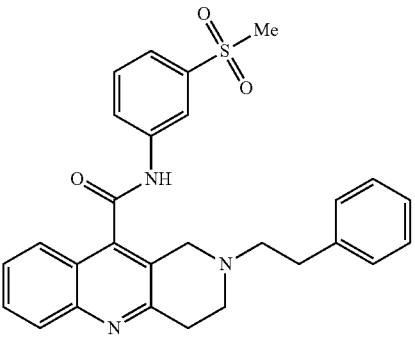 [SMILES: CS(=O)(=O)c1cccc(NC(=O)c2c3c(nc4ccccc24)CCN(CCc2ccccc2)C3)c1]

N-(3-(Methylsulfonyl)phenyl)-2-phenethyl-1,2,3,4-tetrahydrobenzo[b][1,6]naphthyridine-10-carboxamide (146)

A suspension of acid 145 (8.4 mg, 0.025 mmol, 1 equiv) in dichloroethane (250 µL) was stirred at room temperature. Diisopropylethylamine (14 µL, 0.081 mmol, 3.2 equiv) was added followed by TCFH (11 mg, 0.038 mmol, 1.5 equiv), which cleared the suspension. After 2 h, 3-methylsulfonylaniline hydrochloride (10 mg, 0.050 mmol, 2 equiv) was added. The reaction was stirred for an additional 16 h before partitioning between dichloromethane (5 mL) and water (5 mL). The organic layer was collected, and the aqueous layer extracted once more with dichloromethane (5 mL). The extracts were combined, dried over sodium sulfate, decanted, and concentrated. The residue was chromatographed (5% methanol in ethyl acetate) to produce 146 as a solid with 25% tetramethylurea (3.3 mg, 27%), mp: 212.0-216.0° C.: 1H NMR (500 MHz, CDCl$_3$) δ 8.61 (br s, 1H), 8.32 (s, 1H), 8.12 (d, J=8.1 Hz, 1H), 8.00 (d, J=8.4 Hz, 1H), 7.83 (d, J=8.4 Hz, 1H), 7.77 (d, J=8.2 Hz, 1H), 7.69 (t, J=7.7 Hz, 1H), 7.63 (td, J=8.0, 1.8 Hz, 1H), 7.52 (t, J=7.6 Hz, 1H), 7.29-7.24 (m, 4H), 7.23-7.16 (m, 3H), 3.97 (s, 2H), 3.30 (t, J=5.4 Hz, 5H), 3.10-3.01 (m, 3H), 2.94-2.86 (m, 5H), 2.76 (tetramethylurea, d, J=1.9 Hz, 4H); $^{13}$C NMR (126 MHz, CDCl$_3$) δ 165.25, 158.11, 146.86, 141.60, 138.60, 130.45, 129.85, 128.88, 128.64, 128.49, 127.26, 126.30, 124.75, 124.13, 123.46, 122.63, 119.58, 118.49, 109.99, 59.56, 53.41, 50.11, 44.25, 38.56 (tetramethylurea), 33.43, 33.17; ESI-MS [M–H]$^-$ m/z calcd for C$_{28}$H$_{28}$N$_3$O$_3$S$_1$, 486.18; found, 486.2.

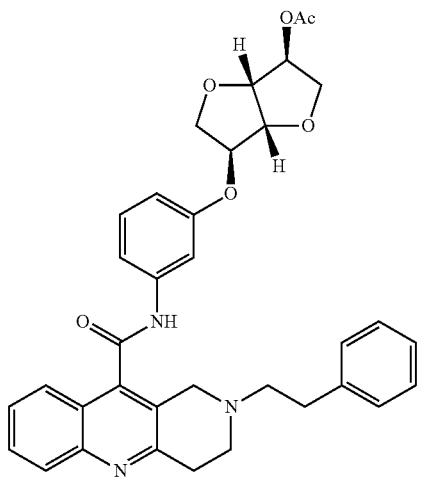 [SMILES: CC(=O)O[C@H]1CO[C@H]2[C@@H]1OC[C@@H]2Oc1cccc(NC(=O)c2c3c(nc4ccccc24)CCN(CCc2ccccc2)C3)c1]

(3S,3aR,6S,6aR)-6-(3-(2-Phenethyl-1,2,3,4-tetrahydrobenzo[b][1,6]naphthyridine-10-carboxamido)phenoxy)hexahydrofuro[3,2-b]furan-3-yl acetate (147)

A suspension of acid 145 (30 mg, 0.09 mmol, 1 equiv) in dichloroethane (500 µL) was stirred at room temperature. Diisopropylethylamine (19 µL, 0.11 mmol, 1.2 equiv) was added followed by TCFH (38 mg, 0.14 mmol, 1.5 equiv), which cleared the suspension. After stirring for 2 h, (3S,3aR,6S,6aR)-6-(3-aminophenoxy)hexahydrofuro[3,2-b]furan-3-yl acetate (38 mg, 0.14 mmol, 1.5 equiv) was added. The reaction was stirred for an additional 16 h then partitioned between dichloromethane (10 mL) and saturated sodium bicarbonate (10 mL). The organic layer was collected, dried over sodium sulfate, decanted, and concentrated. The residue was chromatographed twice (ethyl acetate). The fractions containing product were partially concentrated and cooled to −20° C. for 16 h. The resulting precipitate was collected via filtration producing 145 as a solid (28.4 mg, 53%), mp: 151.3-152.3° C.: 1H NMR (500 MHz, DMSO-$d_6$) δ 10.82 (s, 1H), 7.97-7.95 (m, 1H), 7.75-7.71 (m, 2H), 7.56 (ddd, J=8.1, 6.9, 1.3 Hz, 1H), 7.48-7.46 (m, 1H), 7.33-7.30 (m, 2H), 7.22 (s, 2H), 7.22 (d, J=0.8 Hz, 2H), 7.16-7.10 (m, 1H), 6.81-6.77 (m, 1H), 5.06 (d, J=3.6 Hz, 1H), 4.87 (d, J=3.7 Hz, 1H), 4.64 (d, J=4.2 Hz, 1H), 4.61 (d, J=4.2 Hz, 1H), 4.01 (dd, J=10.5, 4.0 Hz, 1H), 3.94 (dd, J=10.6, 3.7 Hz, 1H), 3.93-3.90 (m, 1H), 3.83 (d, J=10.6 Hz, 1H), 3.80 (d, J=6.3 Hz, 2H), 3.17-3.13 (m, 2H), 2.96 (t, J=5.9 Hz, 2H), 2.83-2.74 (m, 4H), 2.00 (s, 3H); $^{13}$C NMR (126 MHz, CDCl$_3$)$^{13}$C NMR (126 MHz, CDCl$_3$) δ 169.98, 164.90, 157.59, 156.49, 146.54, 139.61, 139.12, 139.07, 130.32, 129.81, 128.68, 128.48, 128.41, 127.14, 126.26, 124.32, 122.63, 112.93, 111.40, 107.51, 107.48, 85.56, 81.11, 81.06, 77.57, 77.53, 72.52, 72.38, 59.60, 53.17, 49.95, 33.49, 33.02, 20.92; ESI-MS [M−H]$^−$ m/z calcd for $C_{35}H_{36}N_3O_6$, 594.25; found, 594.3.

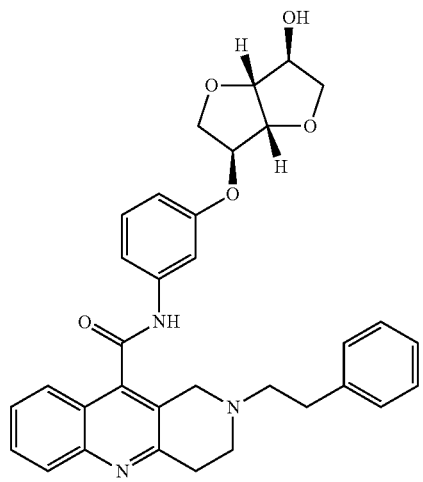 [SMILES: O=C(Nc1cccc(O[C@H]2CO[C@H]3[C@@H]2OC[C@@H]3O)c1)c1c2c(nc3ccccc13)CCN(CCc1ccccc1)C2]

N-(3-(((3S,3aR,6S,6aR)-6-Hydroxyhexahydrofuro[3,2-b]furan-3-yl)oxy)phenyl)-2-phenethyl-1,2,3,4-tetrahydrobenzo[b][1,6]naphthyridine-10-carboxamide (148)

A solution of amide 147 (25 mg, 0.042 mmol, 1 equiv) in methanol (2 mL) is stirred at room temperature. A solution of potassium carbonate (70 mg, 0.51 mmol, 12 equiv) in water (500 L) is added and the mixture stirred for 5 h. The reaction is concentrated to 500 µL, diluted with water (5 mL), and extracted with dichloromethane (2×10 mL). The organic layers are combined, dried over sodium sulfate, decanted, and concentrated to a yellow solid (16.3 mg, 70%): 1H NMR (500 MHz, CDCl$_3$) δ 9.02 (br s, 1H), 8.01 (d, J=8.5 Hz, 1H), 7.84 (d, J=8.3 Hz, 1H), 7.68 (dd, J=8.0, 7.1 Hz, 1H), 7.49 (dd, J=8.1, 7.1 Hz, 1H), 7.34 (t, J=8.2 Hz, 1H), 7.29-7.21 (m, 3H), 7.20-7.14 (m, 3H), 6.74 (d, J=7.7 Hz, 1H), 4.68 (s, 1H), 4.65 (s, 1H), 4.40 (s, 1H), 4.12-3.50 (m, 8H), 3.41-3.24 (m, 3H), 2.98-2.83 (m, 4H), 2.11 (br s, 2H); (partial)$^{13}$C NMR (126 MHz, CDCl$_3$) δ 165.02, 157.55, 146.92, 139.08, 130.38, 129.83, 128.76, 128.63, 128.52, 127.13, 126.34, 124.35, 122.85, 113.26, 107.55, 84.76, 77.25, 77.00, 76.75, 75.45, 74.21, 59.65, 53.35, 50.40, 32.99; ESI-MS [M−H]$^−$ m/z calcd for $C_{33}H_{34}N_3O_5$, 552.24; found, 552.3.

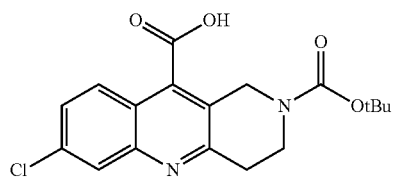 [SMILES: CC(C)(C)OC(=O)N1CCc2nc3cc(Cl)ccc3c(C(=O)O)c2C1]

2-(tert-Butoxycarbonyl)-7-chloro-1,2,3,4-tetrahydrobenzo[b][1,6]naphthyridine-10-carboxylic acid (151)

A solution of 6-chlorosarin (1.007 g, 5.5 mmol, 1 equiv) in 1,4-dioxane (13 mL) was stirred at room temperature. A solution of 4 M potassium hydroxide (13 mL, 54.1 mmol, 10 equiv) was added, and the mixture was stirred for 20 min. N-boc-4-piperidone (1.33 g, 6.7 mmol, 1.2 equiv) was added, and the reaction heated at reflux. After 19 h, the reaction was cooled and diluted with water (50 mL). The mixture was washed sequentially with toluene (25 mL) and diethyl ether (25 mL). The aqueous layer was collected and acidified with 1N hydrochloric acid until a yellow precipitate formed (pH≈2). The suspension was filtered, and the cake rinsed with cold water. The solids were collected to provide 151 as an off-white solid (1.502 g, 75%), mp (decomposition): 211.9-216.8° C.: 1H NMR (500 MHz, DMSO-$d_6$) δ 8.04 (d, J=2.1 Hz, 1H), 7.89 (d, J=9.0 Hz, 1H), 7.65 (dd, J=9.0, 2.2 Hz, 1H), 4.72 (s, 2H), 3.73 (br t, J=6.1 Hz, 2H), 3.12 (t, J=6.2 Hz, 2H), 1.41 (s, 9H); $^{13}$C NMR (126 MHz, DMSO-$d_6$) δ 167.78, 158.61, 146.87, 134.70, 128.21, 127.67, 127.25, 124.37, 121.13, 79.94, 28.43; ESI-MS [M−H]$^-$ calculated for $C_{18}H_{18}ClN_2O_4$, 361.10; found 361.0.

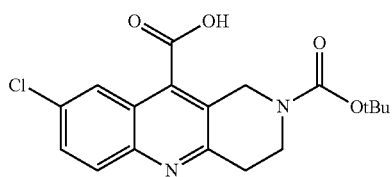 [SMILES: CC(C)(C)OC(=O)N1CCc2nc3ccc(Cl)cc3c(C(=O)O)c2C1]

2-(tert-Butoxycarbonyl)-8-chloro-1,2,3,4-tetrahydrobenzo[b][1,6]naphthyridine-10-carboxylic Acid (152)

The acid was prepared from 5-chlorosarin (1.004 g, 5.5 mmol, 1 equiv) by following the procedure for 151. The solids were collected to provide 152 as an off-white solid (1.521 g, 76%), mp (decomposition): 277.5-286.3° C.; $^1$H NMR (500 MHz, DMSO-$d_6$) δ 8.01 (dd, J=9.0, 1.3 Hz, 1H), 7.87 (s, 1H), 7.79 (dt, J=9.1, 1.8 Hz, 1H), 4.75 (s, 2H), 3.73 (t, J=5.9 Hz, 2H), 3.12 (t, J=6.0 Hz, 2H), 1.40 (s, 9H); (partial)$^{13}$C NMR (126 MHz, DMSO-$d_6$) δ 167.59, 144.98, 138.74, 132.03, 131.28, 130.76, 123.79, 123.23, 79.95, 28.44; ESI-MS [M−H]$^-$ calculated for $C_{18}H_{18}ClN_2O_4$, 361.10; found 361.0.

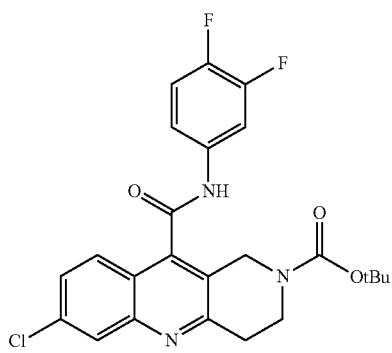 [SMILES: CC(C)(C)OC(=O)N1CCc2nc3cc(Cl)ccc3c(C(=O)Nc3ccc(F)c(F)c3)c2C1]

Tert-Butyl 7-chloro-10-((3,4-difluorophenyl)carbamoyl)-3,4-dihydrobenzo[b][1,6]naphthyridine-2 (1H)-carboxylate (153)

A suspension of acid 151 (108 mg, 0.30 mmol, 1 equiv) in dichloromethane (1.5 mL) was stirred at room temperature under a nitrogen atmosphere. Diisopropylethylamine (65 μL, 0.37 mmol, 1.2 equiv) was added, which cleared the suspension. TCFH (134 mg, 0.48 mmol, 1.6 equiv) was added and the reaction was stirred for 3 h. 3,4-difluoroaniline (60 μL, 0.61 mmol, 2 equiv) was added and the reaction was stirred for 17 h. The solution was concentrated, and the residue partitioned between ethyl acetate (20 mL) and water (20 mL). The organic layer was collected, and the aqueous layer extracted once more with ethyl acetate (20 mL). The organic extracts were combined and washed with saturated sodium bicarbonate (10 mL) then brine (10 mL). The organic layer was then dried over sodium sulfate, decanted, and concentrated. The residue was chromatographed (3:4 ethyl acetate/hexane) to produce 153 as an off-white solid contaminated with 26% tetramethylurea (94 mg, 66%): 1H NMR (400 MHz, CDCl$_3$) δ 9.45 (s, 1H), 7.96 (d, J=2.0 Hz, 1H), 7.88-7.75 (m, 2H), 7.45 (dd, J=8.9, 2.0 Hz, 1H), 7.41-7.31 (m, 1H), 7.14 (q, J=9.1 Hz, 1H), 4.75 (s, 2H), 3.77 (s, 2H), 3.16 (t, J=6.2 Hz, 2H), 2.63 (tetramethylurea, s, 4.2H), 1.37-1.16 (m, 9.8H); ESI-MS [M+H]$^+$ calculated for $C_{24}H_{23}ClF_2N_3O_3$, 374.13; found 474.1.

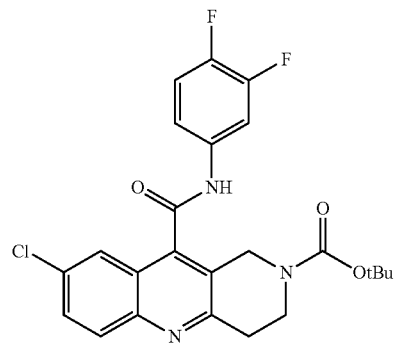 [SMILES: CC(C)(C)OC(=O)N1CCc2nc3ccc(Cl)cc3c(C(=O)Nc3ccc(F)c(F)c3)c2C1]

Tert-Butyl 8-chloro-10-((3,4-difluorophenyl)carbamoyl)-3,4-dihydrobenzo[b][1,6]naphthyridine-2 (1H)-carboxylate (154)

The amide was prepared from acid 152 (92 mg, 0.26 mmol, 1 equiv) by following the procedure for 151. The product was purified via chromatography (1:1 ethyl acetate/hexane) to produce 154 as an off-white solid (93 mg, 74%): 1H NMR (400 MHz, CDCl$_3$) δ 9.51 (s, 1H), 7.89 (ddd, J=12.1, 7.2, 2.5 Hz, 1H), 7.84 (d, J=9.2 Hz, 1H), 7.77 (s, 1H), 7.60 (dd, J=9.0, 2.3 Hz, 1H), 7.42 (ddt, J=8.5, 4.0, 1.9 Hz, 1H), 7.17 (app q, J=9.1 Hz, 1H), 4.67 (br s, 2H), 3.73 (br s, 2H), 3.09 (t, J=6.2 Hz, 2H), 1.29 (s, 9H); ESI-MS [M+H]$^+$ calculated for $C_{24}H_{23}ClF_2N_3O_3$, 374.13; found 474.1.

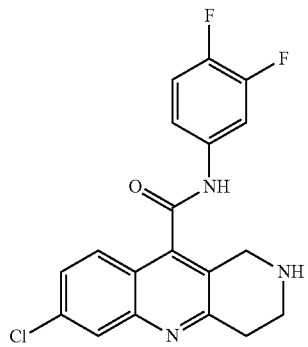 [SMILES: O=C(Nc1ccc(F)c(F)c1)c1c2c(nc3cc(Cl)ccc13)CCNC2]

7-Chloro-N-(3,4-difluorophenyl)-1,2,3,4-tetrahydrobenzo[b][1,6]naphthyridine-10-carboxamide (155)

A solution of protected amine 153 (61 mg, 0.13 mmol, 1 equiv) was dissolved in dichloromethane (870 μL). Trifluoroacetic acid (440 μL, 5.7 mmol, 44 equiv) was added and the reaction stirred at room temperature. After 1 h, the solution was concentrated, and the residue dissolved in a mixture of acetonitrile (5 mL) and 1N sodium hydroxide (7 mL). After 72 h, the solution was partially concentrated to 7 mL and extracted with ethyl acetate (3×15 mL). The organic extracts were combined, dried over sodium sulfate, and concentrated to produce 155 as a white solid contaminated with tert-butyl trifluoroacetate (54 mg, >95%): 1H NMR (500 MHz, CDCl$_3$) δ 9.67 (s, 1H), 8.00-7.94 (m, 1H), 7.63 (s, 1H), 7.58 (d, J=8.9 Hz, 1H), 7.52 (app d, J=7.8 Hz, 2H), 7.38 (d, J=8.9 Hz, 1H), 7.21 (app q, J=8.9 Hz, 2H), 5.65 (br s, 0.7H), 5.57 (br s, 0.6H), 4.12 (s, 2H), 3.38 (s, 2H), 3.29-3.14 (m, 1.3H), 3.04 (t, J=5.9 Hz, 2H), 2.95 (br s, 2H); ESI-MS [M+H]$^+$ calculated for C$_{19}$H$_{15}$ClF$_2$N$_3$O, 374.08; found 374.0.

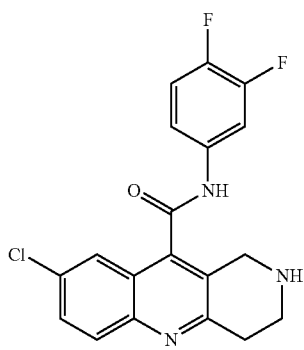 [SMILES: O=C(Nc1ccc(F)c(F)c1)c1c2c(nc3ccc(Cl)cc13)CCNC2]

8-Chloro-N-(3,4-difluorophenyl)-1,2,3,4-tetrahydrobenzo[b][1,6]naphthyridine-10-carboxamide (156)

A solution of protected amine 154 (91 mg, 0.19 mmol, 1 equiv) was dissolved in dichloromethane (1.28 mL). Trifluoroacetic acid (640 μL, 8.4 mmol, 44 equiv) was added and the reaction stirred at room temperature. After 1 h, the solution was concentrated, and the residue suspended in 1N sodium hydroxide (7 mL). After 22 h, the solution was extracted with ethyl acetate (3×15 mL). The organic extracts were combined, dried over sodium sulfate, and concentrated to produce 156 as a white solid contaminated with tert-butyl trifluoroacetate (65 mg, 90%): 1H NMR (400 MHz, CDCl$_3$) δ 8.75 (s, 1H), 8.00-7.92 (m, 1H), 7.81-7.74 (m, 1H), 7.65-7.62 (m, 1H), 7.57 (dt, J=8.9, 1.9 Hz, 1H), 7.50-7.43 (m, 1H), 7.23 (app q, J=9.1 Hz, 1H), 4.21 (s, 2H), 3.31 (s, 2H), 3.15 (s, 2H), 2.89 (br s, 2H); ESI-MS [M+H]$^+$ calculated for C$_{19}$H$_{15}$ClF$_2$N$_3$O, 374.08; found 374.0.

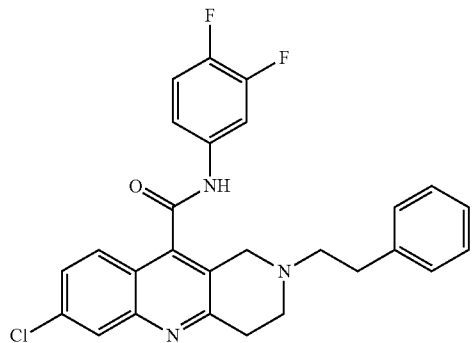 [SMILES: O=C(Nc1ccc(F)c(F)c1)c1c2c(nc3cc(Cl)ccc13)CCN(CCc1ccccc1)C2]

7-Chloro-N-(3,4-difluorophenyl)-2-phenethyl-1,2,3,4-tetrahydrobenzo[b][1,6]naphthyridine-10-carboxamide (157)

A solution of amine 155 (25 mg, 0.067 mmol, 1 equiv) in DMF (1 mL) was stirred at room temperature. A portion of (2-bromoethyl)benzene (13 μL, 0.095 mmol, 1.4 equiv) was added followed by potassium carbonate (32 mg, 0.23 mmol, 3.4 equiv). The reaction mixture was heated to 35° C. for 72 h, cooled to room temperature, and stirred for an additional 72 h. The reaction was diluted with water (20 mL) and extracted with ethyl acetate (20 mL). The organic extract was washed with water (4×10 mL) then brine (10 mL). The organic layer was dried over sodium sulfate, decanted, and concentrated. The residue was chromatographed twice (9:1 ethyl acetate/hexane) to provide 157 as a yellow solid (2.2 mg, 6.9%): 1H NMR (500 MHz, CDCl3) δ 8.03 (s, 1H), 7.96 (d, J=2.0 Hz, 1H), 7.90 (ddd, J=12.0, 7.0, 2.5 Hz, 1H), 7.73 (d, J=9.0 Hz, 1H), 7.46 (dd, J=8.5, 2.0 Hz, 1H), 7.18-7.32 (m, 7H), 3.89 (s, 2H), 3.25 (t, J=6.3 Hz, 2H), 3.00 (s, 2H), 2.90 (s, 2H), 2.88 (s, 2H); $^{13}$C NMR (126 MHz, CDCl$_3$) δ 164.30, 158.01, 150.29 (dd, J=249.0, 13.4 Hz), 147.62 (dd, J=247.9, 13.2 Hz), 147.08, 139.48, 138.52, 135.77, 133.71, 128.62, 128.49, 128.22, 127.80, 126.30, 125.44, 121.00, 117.68 (d, J=17.6 Hz), 115.51 (dd, J=5.7, 3.8 Hz), 109.85 (d, J=22.0 Hz), 59.62, 53.32, 49.93, 33.58, 33.31, 29.69 (grease); $^{19}$F NMR (470 MHz, CDCl$_3$) δ−134.34−−134.64 (m), −140.59−−140.99 (m); ESI-MS [M+H]$^+$ calculated for C$_{27}$H$_{23}$ClF$_2$N$_3$O, 478.14; found 478.1.

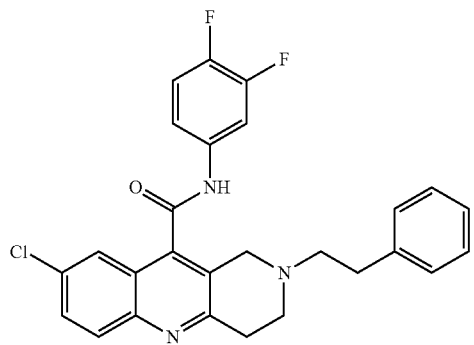 [SMILES: O=C(Nc1ccc(F)c(F)c1)c1c2c(nc3ccc(Cl)cc13)CCN(CCc1ccccc1)C2]

8-Chloro-N-(3,4-difluorophenyl)-2-phenethyl-1,2,3,4-tetrahydrobenzo[b][1,6]naphthyridine-10-carboxamide (158)

A solution of amine 156 (30 mg, 0.080 mmol, 1 equiv) in DMF (1 mL) was stirred at room temperature. (2-bromoethyl)benzene (13 μL, 0.095 mmol, 1.2 equiv) was added followed by potassium carbonate (36 mg, 0.26 mmol, 3.3 equiv). The reaction was heated at 40° C. for 19 h, an additional portion of (2-bromoethyl)benzene (4 μL, 0.03 mmol, 0.4 equiv) was added. The reaction was left to stir at 40° C. for 21 h then cooled to room temperature. The reaction was diluted with water (20 mL) and extracted with ethyl acetate (20 mL). The organic extract was washed with water (3×10 mL) then brine (10 mL). The organic layer was dried over sodium sulfate, decanted, and concentrated. The residue was chromatographed (ethyl acetate) to provide 158 as an off-white solid (5.5 mg, 14%): 1H NMR (400 MHz, CDCl3) δ 8.54 (s, 1H), 7.94 (ddd, J=12.0, 7.2, 2.4 Hz, 1H), 7.87 (d, J=9.2 Hz, 1H), 7.74 (d, J=2.0 Hz, 1H), 7.60 (dd, J=9.0, 2.2 Hz, 1H), 7.38-7.41 (m, 1H), 7.18-7.30 (m, 6H), 3.92 (s, 2H), 3.26 (t, J=6.2 Hz, 2H), 3.05 (s, 2H), 2.92 (s, 4H); 19F NMR (470 MHz, CDCl3) δ-75.98 (Trifluoroacetic acid), −134.60--135.01 (m), −140.72--141.32 (m); ESI-MS [M+H]+ calculated for $C_{27}H_{23}ClF_2N_3O$, 478.14; found 478.1.

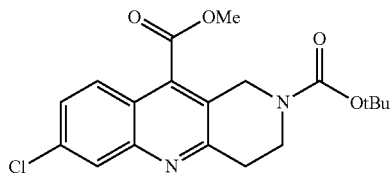 [SMILES: COC(=O)c1c2c(nc3cc(Cl)ccc13)CCN(C(=O)OC(C)(C)C)C2]

2-(tert-Butyl) 10-methyl 7-chloro-3,4-dihydrobenzo[b][1,6]naphthyridine-2,10(1H)-dicarboxylate (159)

A suspension of acid 151 (1.0 g, 2.8 mmol, 1 equiv), in 5:1 THF/DMF (13.8 mL) was prepared in a thick-walled glass tube under a nitrogen atmosphere. Potassium carbonate (305 mg, 2.2 mmol, 0.8 equiv) was added, followed by methyl iodide (755 μL, 12.1 mmol, 4.4 equiv). After sealing the tube, the reaction mixture was heated to 55° C. and stirred for 16 h. The orange solution was cooled to room temperature, quenched with water (15 mL), and extracted with diethyl ether (3×15 mL). The organic extracts are combined, dried over sodium sulfate, filtered, and concentrated. Hexanes (15 mL) was added, and the mixture was brought to a boil. The solvent was collected, and the residue was re-subjected to boiling hexanes (2×15 mL), leaving insoluble impurities. The combined hexane extract was concentrated to afford a yellow solid (844 mg, 81%): 1H NMR (500 MHz, CDCl3) δ 8.07 (s, 1H), 7.78 (d, J=9.1 Hz, 1H), 7.50 (d, J=9.0 Hz, 1H), 4.79 (s, 2H), 4.08 (s, 3H), 3.83 (t, J=5.9 Hz, 2H), 3.25 (br t, J=6.2 Hz, 2H), 1.50 (s, 9H).

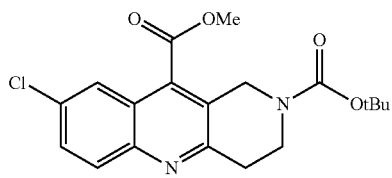 [SMILES: COC(=O)c1c2c(nc3ccc(Cl)cc13)CCN(C(=O)OC(C)(C)C)C2]

2-(tert-Butyl) 10-methyl 8-chloro-3,4-dihydrobenzo[b][1,6]naphthyridine-2,10(1H)-dicarboxylate (160)

The ester was prepared from acid 152 (1.0 g, 2.8 mmol, 1 equiv) by following the procedure for 159. Concentration of the hexane extracts produced the product as a yellow solid (800 mg, 77%), mp: 126.0-128.9° C.: 1H NMR (500 MHz, CDCl3) δ 7.96 (d, J=9.0 Hz, 1H), 7.82 (d, J=2.3 Hz, 1H), 7.64 (dd, J=9.0, 2.3 Hz, 1H), 4.80 (s, 2H), 4.09 (s, 3H), 3.83 (t, J=6.1 Hz, 2H), 3.22 (t, J=5.9 Hz, 2H), 1.49 (s, 9H); ESI-MS [M+H]+ calculated for $C_{19}H_{22}ClN_2O_4$, 377.12; found 377.1.

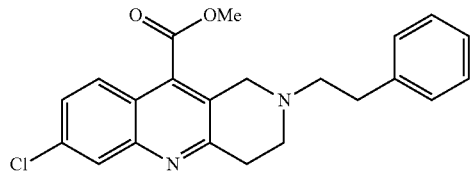 [SMILES: COC(=O)c1c2c(nc3cc(Cl)ccc13)CCN(CCc1ccccc1)C2]

Methyl 7-chloro-2-phenethyl-1,2,3,4-tetrahydrobenzo[b][1,6]naphthyridine-10-carboxylate (161)

A solution of ester 159 (844 mg, 2.24 mmol, 1 equiv) in dichloromethane (5.7 mL) and Trifluoroacetic acid (3.4 mL) was stirred at room temperature. After one h, the reaction was concentrated, and the residue weighed to determine the mass of residual trifluoroacetic acid assuming quantitative deprotection. 620 mg of this residue (1.1 mmol deprotected ester and 2.7 mmol trifluoroacetic acid) was dissolved in dichloroethane (7.8 mL). triethylamine (378 μL, 2.7 mmol) was added, followed by phenylacetaldehyde (157 μL, 1.3 mmol, 1.2 equiv). After stirring for one h, sodium triacetoxyborohydride (474 mg, 2.2 mmol, 2 equiv) was added. After stirring for an additional 16 h, the reaction was quenched with saturated sodium bicarbonate (50 mL). The mixture was extracted with ethyl acetate (2×50 mL) and, the organic extracts combined, dried over sodium sulfate, decanted, and concentrated. The residue is chromatographed (1:1 ethyl acetate/hexane) to produce 161 as a light brown solid (260 mg, 64%), mp: 122.8-124.5° C.: 1H NMR (500 MHz, CDCl3) δ 8.02 (d, J=2.1 Hz, 1H), 7.72 (d, J=8.9 Hz, 1H), 7.46 (dd, J=9.0, 2.1 Hz, 1H), 7.33-7.28 (m, 2H), 7.26-7.20 (m, 3H), 4.05 (s, 3H), 3.88 (s, 2H), 3.30 (t, J=5.9 Hz, 2H), 3.03 (s, 2H), 2.97-2.90 (m, 2H), 2.90-2.84 (m, 2H); 13C NMR (126 MHz, CDCl3) δ 167.01, 157.90, 147.10, 139.91, 135.43, 135.23, 128.68, 128.46, 127.83, 127.78, 126.20, 125.88, 121.21, 59.63, 53.96, 52.74, 52.71, 50.04, 33.91, 33.44; ESI-MS [M+H]+ calculated for $C_{22}H_{22}ClN_2O_2$, 381.13; found 381.3.

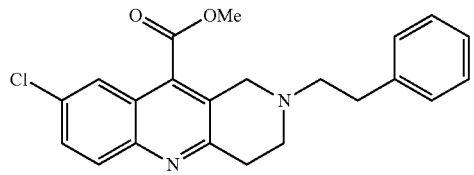 [SMILES: COC(=O)c1c2c(nc3ccc(Cl)cc13)CCN(CCc1ccccc1)C2]

Methyl 8-chloro-2-phenethyl-1,2,3,4-tetrahydrobenzo[b][1,6]naphthyridine-10-carboxylate (162)

A solution of ester 160 (766 mg, 2.03 mmol, 1 equiv) in dichloromethane (20 mL) and Trifluoroacetic acid (10 mL) was stirred at room temperature. After one h, the reaction was concentrated, and the residue weighed to determine the mass of residual trifluoroacetic acid (quantitative deprotection assumed). 1.207 g of this residue (2.03 mmol deprotected ester and 5.6 mmol trifluoroacetic acid) was dissolved in dichloroethane (20 mL). triethylamine (935 µL, 6.7 mmol) was added, followed by phenylacetaldehyde (413 µL, 3.7 mmol, 1.8 equiv). After 1 h, sodium triacetoxyborohydride (1.31 g, 2.2 mmol, 3 equiv) was added. After an additional 16 h, the reaction was quenched with saturated sodium bicarbonate (50 mL). The mixture was extracted with ethyl acetate (2×50 mL) and, the organic extracts combined, dried over sodium sulfate, decanted, and concentrated. The residue was chromatographed (1:1 ethyl acetate/hexane) to produce a light-brown solid (533 mg, 69%), mp: 85.3-87.4° C.: 1H NMR (500 MHz, CDCl$_3$) δ 7.95 (d, J=9.0 Hz, 1H), 7.77 (d, J=2.3 Hz, 1H), 7.61 (dd, J=9.0, 2.3 Hz, 1H), 7.33-7.28 (m, 2H), 7.26-7.20 (m, 3H), 4.06 (s, 3H), 3.88 (s, 2H), 3.29 (t, J=6.1 Hz, 2H), 3.02 (t, J=6.1 Hz, 2H), 2.95-2.90 (m, 2H), 2.89-2.84 (m, 2H); $^{13}$C NMR (126 MHz, CDCl$_3$ δ 166.88, 156.92, 145.18, 139.87, 134.61, 132.74, 130.46, 130.37, 128.68, 128.47, 126.63, 126.22, 123.46, 123.41, 59.61, 54.02, 52.79, 50.06, 33.91, 33.36; ESI-MS [M+H]$^+$ calculated for C$_{22}$H$_{22}$ClN$_2$O$_2$, 381.13; found 381.2.

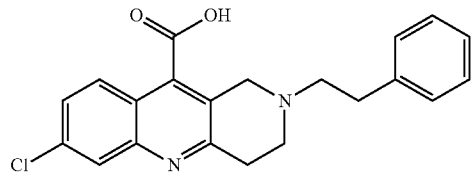 [SMILES: O=C(O)c1c2c(nc3cc(Cl)ccc13)CCN(CCc1ccccc1)C2]

7-Chloro-2-phenethyl-1,2,3,4-tetrahydrobenzo[b][1,6]naphthyridine-10-carboxylic Acid (163)

A solution of ester 161 (364 mg, 0.95 mmol, 1 equiv) in methanol (18 mL) was stirred at room temperature. A solution of 3.2 M potassium hydroxide (6 mL, 19.1 mmol, 20 equiv) was added causing a precipitate to form. The mixture was stirred for 16 h, heated to 35° C. for an h to clear the suspension, then cooled to room temperature and allowed to stir for an additional 72 h. The solution was partially concentrated to 6 mL then washed with diethyl ether (15 mL). The aqueous layer was acidified with 1N hydrochloric acid (pH≈4.7) causing a solid to form. The suspension was filtered, and the solid rinsed with cold water to produce 163 as a yellow solid (268 mg, 76%), mp (decomposition): 240° C.: 1H NMR (500 MHz, CD$_3$CO$_2$D) δ 8.19 (s, 1H), 8.17 (d, J=9.7 Hz, 1H), 7.67 (d, J=9.0 Hz, 1H), 7.34 (app d, J=4.4 Hz, 4H), 7.27 (q, J=4.6 Hz, 1H), 4.97 (s, 2H), 4.02-3.90 (m, 2H), 3.71 (t, J=8.4 Hz, 2H), 3.33-3.28 (m, 2H), 2.08-2.02 (m, 10H, overlapped with acetic acid).

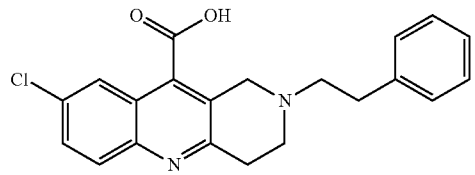 [SMILES: O=C(O)c1c2c(nc3ccc(Cl)cc13)CCN(CCc1ccccc1)C2]

8-Chloro-2-phenethyl-1,2,3,4-tetrahydrobenzo[b][1,6]naphthyridine-10-carboxylic Acid (164)

A solution of ester 162 (500 mg, 1.31 mmol, 1 equiv) in methanol (21 mL) was stirred at room temperature. A solution of 3.75 M potassium hydroxide (7 mL, 26.3 mmol, 20 equiv) was added and the mixture was stirred for 16 h. The solution was partially concentrated to 7 mL then acidified with 1N hydrochloric acid (pH≈4.7), which caused a solid to form. The suspension was filtered, and the solid rinsed with cold water to produce 164 as a yellow solid (416 mg, 87%): 1H NMR (500 MHz, CD$_3$CO$_2$D) δ 8.10 (s, 1H), 8.00 (d, J=8.9 Hz, 1H), 7.75 (d, J=9.0 Hz, 1H), 7.40-7.22 (m, 5H), 4.92 (s, 2H), 3.91 (s, 2H), 3.74-3.64 (m, 2H), 3.32-3.24 (m, 2H), 2.06-2.02 (m, 4H); $^{13}$C NMR (126 MHz, CD$_3$CO$_2$D) δ 151.97, 143.59, 135.87, 133.54, 132.19, 128.80, 128.72, 127.86, 127.16, 124.64, 123.43, 118.30, 57.63, 51.56, 49.22, 30.10; ESI-MS [M−H]$^−$ calculated for C$_{21}$H$_{18}$ClN$_2$O$_2$, 365.11; found 365.3.

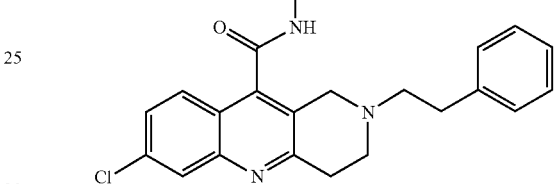

7-Chloro-N-(4-chlorophenyl)-2-phenethyl-1,2,3,4-tetrahydrobenzo[b][1,6]naphthyridine-10-carboxamide (165)

A suspension of acid 163 (50 mg, 0.14 mmol, 1 equiv) in dichloroethane (729 µL) was stirred under a nitrogen atmosphere at room temperature. Diisopropylethylamine (26 µL, 0.16 mmol, 1.2 equiv) is added, which cleared the suspension, followed by TCFH (55 mg, 0.20 mmol, 1.5 equiv). After stirring for 2 h, 4-chloroaniline (22 µL, 0.20 mmol, 1.5 equiv) was added, and the reaction was stirred for an additional 16 h. The reaction was diluted with dichloromethane (10 mL) and the washed saturated sodium bicarbonate (2×10 mL). The organic layer was dried over sodium sulfate, decanted, and concentrated. The residue was chromatographed (ethyl acetate) to produce 165 contaminated with tetramethylurea (7%): 1H NMR (500 MHz, CDCl$_3$) δ 8.44 (s, 1H), 7.89 (d, J=2.0 Hz, 1H), 7.75 (d, J=8.8 Hz, 2H), 7.71 (d, J=8.9 Hz, 1H), 7.44 (dd, J=8.9, 2.0 Hz, 1H), 7.40 (d, J=8.8 Hz, 2H), 7.29-7.24 (m, 2H), 7.22-7.17 (m, 3H), 3.95 (s, 1H), 3.22 (t, J=6.2 Hz, 1H), 3.05 (br s, 2H), 2.92 (s, 4H), 2.71 (tetramethylurea, s, 1H); $^{13}$C NMR (126 MHz, CDCl$_3$) δ 164.16, 157.14, 146.99, 139.10, 138.83, 135.96, 135.94, 130.49, 129.40, 128.62, 128.59, 128.30, 127.58, 126.49, 125.61, 123.59, 121.20, 121.03, 59.53, 53.10, 49.91, 33.17, 32.73; ESI-MS [M+H]$^+$ calculated for C$_{27}$H$_{24}$Cl$_2$N$_3$O, 476.12; found 476.2. The solid was dissolved in ethyl acetate to remove tetramethylurea. The organic layer was washed with water and concentrated. The resulting solid was suspended in toluene, washed with three times with water, and concentrated to produce 165 as a solid with 9% oxidized product (28 mg, 44%), mp: 178.7-180.2° C.

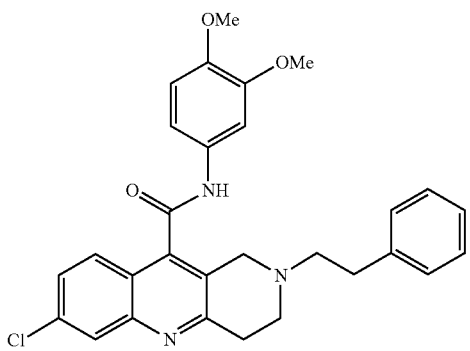 [SMILES: COc1ccc(NC(=O)c2c3c(nc4cc(Cl)ccc24)CCN(CCc2ccccc2)C3)cc1OC]

7-Chloro-N-(3,4-dimethoxyphenyl)-2-phenethyl-1,2,3,4-tetrahydrobenzo[b][1,6]naphthyridine-10-carboxamide (166)

The title amide was prepared from acid 163 (50 mg, 0.14 mmol, 1 equiv) and 3,4-dimethoxyaniline (30 mg, 0.20 mmol, 1.5 equiv) by following the procedure for 165. After Chromatography (ethyl acetate), the solid was suspended in toluene and washed three times with water. The organic layer was concentrated to produce 166 as a solid with 3% tetramethylurea (32 mg, 49%): 1H NMR (500 MHz, CDCl$_3$) δ 8.12 (s, 1H), 7.94 (d, J=2.0 Hz, 1H), 7.79 (d, J=8.9 Hz, 1H), 7.59 (d, J=2.4 Hz, 1H), 7.45 (dd, J=8.9, 2.1 Hz, 1H), 7.31-7.23 (m, 2H), 7.23-7.14 (m, 4H), 6.90 (d, J=8.7 Hz, 1H), 3.94 (s, 3H), 3.93 (s, 2H), 3.91 (s, 3H), 3.25 (t, J=6.1 Hz, 2H), 3.01 (br s, 2H), 2.95-2.90 (m, 2H), 2.90-2.85 (m, 2H), 2.76 (s, 0.4H); $^{13}$C NMR (126 MHz, CDCl$_3$) δ 163.95, 157.90, 149.28, 146.80, 146.47, 139.55, 139.32, 135.58, 131.33, 128.64, 128.47, 127.38, 126.26, 125.81, 124.58, 121.17, 111.72, 111.50, 104.56, 104.54, 59.63, 56.20, 56.17, 56.12, 56.05, 53.16, 49.80, 38.52 (tetramethylurea), 33.51, 33.19; ESI-MS [M+H]$^+$ calculated for C$_{29}$H$_{29}$ClN$_3$O$_3$, 502.18; found 502.1.

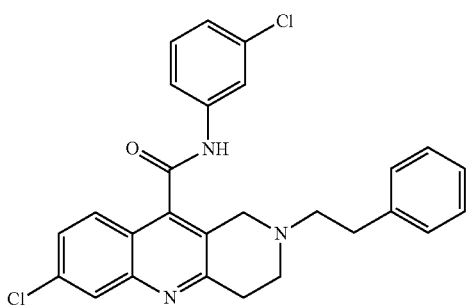 [SMILES: O=C(Nc1cccc(Cl)c1)c1c2c(nc3cc(Cl)ccc13)CCN(CCc1ccccc1)C2]

7-Chloro-N-(3-chlorophenyl)-2-phenethyl-1,2,3,4-tetrahydrobenzo[b][1,6]naphthyridine-10-carboxamide (167)

The title amide was prepared from acid 163 (50 mg, 0.14 mmol, 1 equiv) and 3-chloroaniline (21 µL, 0.20 mmol, 1.5 equiv) by following the procedure for 165. Chromatography (ethyl acetate) produced a solid contaminated with tetramethylurea (21%): 1H NMR (500 MHz, CDCl$_3$) δ 8.99 (s, 1H), 8.02 (t, J=2.0 Hz, 1H), 7.80 (d, J=1.9 Hz, 1H), 7.68 (ddd, J=8.1, 2.1, 1.0 Hz, 1H), 7.66 (d, J=8.8 Hz, 1H), 7.40 (dd, J=9.0, 2.1 Hz, 1H), 7.37 (t, J=8.0 Hz, 1H), 7.29-7.24 (m, 2H), 7.23 (ddd, J=8.1, 2.1, 0.9 Hz, 1H), 7.21-7.16 (m, 3H), 3.79 (s, 2H), 3.12 (t, J=6.2 Hz, 2H), 2.93-2.85 (m, 4H), 2.85-2.77 (m, 2H). 2.66 (tetramethylurea, s, 3.3H); $^{13}$C NMR (126 MHz, cdcl$_3$) δ 164.44, 158.10, 146.59, 139.65, 138.84, 138.83, 135.69, 135.08, 130.36, 128.64, 128.46, 128.08, 127.25, 126.23, 125.60, 125.28, 124.79, 120.96, 120.04, 117.80, 59.58, 53.04, 49.66, 38.46 (tetramethylurea), 33.53, 33.16; ESI-MS [M+H]$^+$ calculated for C$_{27}$H$_{24}$Cl$_2$N$_3$O, 476.12; found 476.0. The solid was dissolved in ethyl acetate to remove tetramethylurea. The organic layer was washed with water and concentrated. The resulting solid was suspended in toluene, washed with three times with water, and concentrated to produce 167 as a solid with 20% oxidized product (23 mg, 34%), mp (decomposition): 120° C.

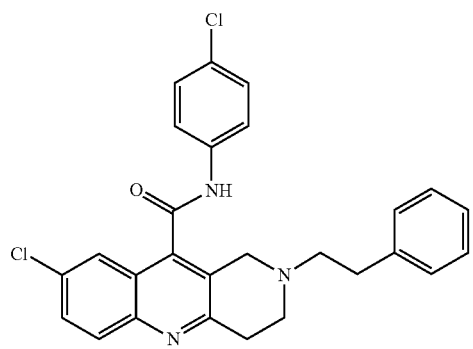 [SMILES: O=C(Nc1ccc(Cl)cc1)c1c2c(nc3ccc(Cl)cc13)CCN(CCc1ccccc1)C2]

8-Chloro-N-(4-chlorophenyl)-2-phenethyl-1,2,3,4-tetrahydrobenzo[b][1,6]naphthyridine-10-carboxamide (168)

A suspension of acid 164 (50 mg, 0.14 mmol, 1 equiv) in dichloroethane (757 µL) was stirred under a nitrogen atmosphere at room temperature. Diisopropylethylamine (26 µL, 0.16 mmol, 1.2 equiv) is added, which cleared the suspension, followed by TCFH (57 mg, 0.20 mmol, 1.5 equiv). After stirring for 2 h, 4-chloroaniline (22 µL, 0.20 mmol, 1.5 equiv) was added, and the reaction is stirred for an additional 16 h. The reaction was diluted with dichloromethane (10 mL) and the washed saturated sodium bicarbonate (2×10 mL). The organic layer was dried over sodium sulfate, decanted, and concentrated. The residue was chromatographed (ethyl acetate) producing a solid contaminated with tetramethylurea. The solid was dissolved in diethyl ether and washed three times with water. The organic layer was concentrated to produce 168 as a solid with 5% oxidized impurity (31 mg, 39%), mp: 195.8-200.6° C.: 1H NMR (500 MHz, CDCl$_3$) δ 8.82 (s, 1H), 7.81 (d, J=8.9 Hz, 2H), 7.80 (d, J=9.3 Hz, 1H), 7.70 (d, J=2.2 Hz, 1H), 7.55 (dd, J=9.0, 2.3 Hz, 1H), 7.41 (d, J=8.8 Hz, 2H), 7.30-7.24 (m, 2H), 7.23-7.17 (m, 3H), 3.87 (s, 2H), 3.19 (t, J=5.9 Hz, 2H), 2.99 (br s, 2H), 2.96-2.84 (m, 4H); $^{13}$C NMR (126 MHz, CDCl$_3$) δ 164.05, 156.57, 144.90, 139.15, 138.28, 136.14, 133.16, 130.97, 130.40, 129.88, 129.39, 128.62, 128.56, 126.42, 124.70, 123.23, 123.19, 121.20, 59.50, 53.01, 49.82, 33.19, 32.79; ESI-MS [M+H]$^+$ calculated for C$_{27}$H$_{24}$Cl$_2$N$_3$O, 476.12; found 476.0.

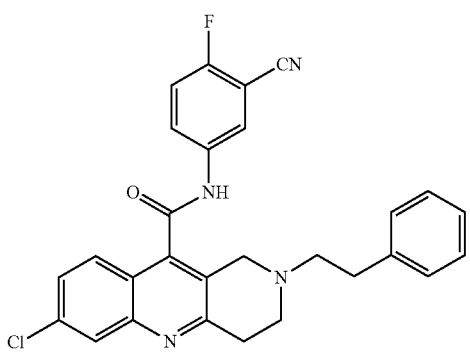 [SMILES: N#Cc1cc(NC(=O)c2c3c(nc4cc(Cl)ccc24)CCN(CCc2ccccc2)C3)ccc1F]

7-Chloro-N-(3-cyano-4-fluorophenyl)-2-phenethyl-1,2,3,4-tetrahydrobenzo[b][1,6]naphthyridine-10-carboxamide (169)

The title amide was prepared from acid 163 (50 mg, 0.14 mmol, 1 equiv) and 5-amino-2-fluorobenzonitrile (27 mg, 0.20 mmol, 1.5 equiv) by following the procedure for 165. Chromatography (3:1 ethyl acetate/hexane) produced 169 as a solid contaminated with tetramethylurea (12%): 1H NMR (500 MHz, CDCl$_3$) δ 9.31 (s, 1H), 8.25 (dd, J=5.4, 2.7 Hz, 1H), 8.06 (ddd, J=8.9, 4.4, 2.9 Hz, 1H), 7.77 (d, J=2.0 Hz, 1H), 7.66 (d, J=8.9 Hz, 1H), 7.43 (dd, J=8.9, 2.0 Hz, 1H), 7.32-7.24 (m, 3H), 7.22-7.16 (m, 3H), 3.79 (s, 2H), 3.12 (t, J=5.8 Hz, 2H), 3.00-2.78 (m, 6H), 2.57 (tetramethylurea, s, 1.5H); $^{13}$C NMR (126 MHz, CDCl$_3$) δ 164.55, 159.87 (d, J=258.0 Hz), 158.12, 146.52, 139.53, 138.48, 135.89, 134.69 (d, J=3.2 Hz), 128.60, 128.50, 128.27, 127.16, 126.31, 126.14 (d, J=7.7 Hz), 125.50, 124.89, 124.04, 120.90, 117.34 (d, J=20.6 Hz), 113.44, 101.96 (d, J=16.7 Hz), 59.54, 53.13, 49.57, 38.39 (tetramethylurea), 33.51, 33.12; $^{19}$F NMR (470 MHz, CDCl$_3$) δ−110.28 (dt, J=8.6, 5.0 Hz); ESI-MS [M+H]$^+$ calculated for C$_{28}$H$_{23}$ClFN$_4$O, 485.15; found 485.1. The solid was dissolved in ethyl acetate to remove tetramethylurea. The organic layer was washed with water and concentrated. The resulting solid was suspended in toluene, washed with three times with water, and concentrated to produce 169 as a solid with 11% oxidized product (28 mg, 45%), mp (decomposition): 190.0° C.

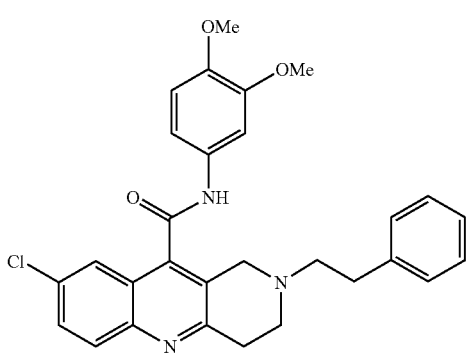 [SMILES: COc1ccc(NC(=O)c2c3c(nc4ccc(Cl)cc24)CCN(CCc2ccccc2)C3)cc1OC]

8-Chloro-N-(3,4-dimethoxyphenyl)-2-phenethyl-1,2,3,4-tetrahydrobenzo[b][1,6]naphthyridine-10-carboxamide (170)

A suspension of acid 164 (50 mg, 0.14 mmol, 1 equiv) in dichloroethane (757 μL) was stirred under a nitrogen atmosphere at room temperature. Diisopropylethylamine (26 μL, 0.16 mmol, 1.2 equiv) is added, which cleared the suspension, followed by TCFH (57 mg, 0.20 mmol, 1.5 equiv). After stirring for 2 h, 3,4-dimethoxyaniline (31 mg, 0.20 mmol, 1.5 equiv) was added, and the reaction is stirred for an additional 16 h. The reaction was diluted with dichloromethane (10 mL) and the washed saturated sodium bicarbonate (2×10 mL). The organic layer was dried over sodium sulfate, decanted, and concentrated. The residue was chromatographed (ethyl acetate) producing a solid contaminated with tetramethylurea. The solid was dissolved in ethyl acetate and washed three times with water. The organic layer was concentrated to produce 170 as a solid with 7% tetramethylurea (34 mg, 50%), mp (decomposition): 82.4-124.1° C.: 1H NMR (500 MHz, CDCl$_3$) δ 8.63 (s, 1H), 7.79 (d, J=9.0 Hz, 1H), 7.72 (d, J=2.2 Hz, 1H), 7.66 (d, J=2.4 Hz, 1H), 7.53 (dd, J=9.0, 2.2 Hz, 1H), 7.30-7.24 (m, 3H), 7.23-7.16 (m, 3H), 6.90 (d, J=8.6 Hz, 1H), 3.93 (s, 3H), 3.90 (s, 3H), 3.84 (s, 2H), 3.16 (t, J=6.1 Hz, 2H), 2.95-2.86 (m, 4H), 2.86-2.80 (m, 2H), 2.70 (tetramethylurea, s, 0.9H); $^{13}$C NMR (126 MHz, CDCl$_3$) δ 171.16 (ethyl acetate), 163.77, 157.04, 149.28, 146.46, 144.76, 139.63, 138.47, 132.89, 131.40, 130.73, 129.74, 128.63, 128.48, 126.24, 125.37, 123.32, 123.23, 111.69, 111.51, 104.54, 60.38 (ethyl acetate), 59.64, 56.18, 56.05, 53.16, 49.82, 33.46, 33.14, 21.02 (ethyl acetate), 14.17 (ethyl acetate); ESI-MS [M+H]$^+$ calculated for C$_{29}$H$_{29}$ClN$_3$O$_3$, 502.18; found 502.1.

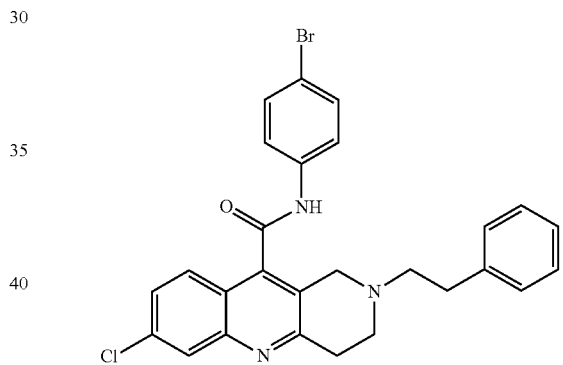

N-(4-Bromophenyl)-7-chloro-2-phenethyl-1,2,3,4-tetrahydrobenzo[b][1,6]naphthyridine-10-carboxamide (171)

A suspension of acid 163 (50 mg, 0.14 mmol, 1 equiv) in dichloroethane (757 μL) was stirred under a nitrogen atmosphere at room temperature. Diisopropylethylamine (26 μL, 0.16 mmol, 1.2 equiv) is added, which cleared the suspension, followed by TCFH (57 mg, 0.20 mmol, 1.5 equiv). After stirring for 2 h, 4-bromoaniline (34 mg, 0.20 mmol, 1.5 equiv) was added, and the reaction is stirred for an additional 16 h. The reaction was diluted with dichloromethane (10 mL) and the washed saturated sodium bicarbonate (2×10 mL). The organic layer was dried over sodium sulfate, decanted, and concentrated. The residue was chromatographed (ethyl acetate) producing a solid contaminated with tetramethylurea. The solid was dissolved in ethyl acetate and washed three times with water. The organic layer was concentrated, suspended in toluene, and washed an additional three times with water. The suspension was concentrated to produce 171 as a solid with 8% oxidized impurity (37 mg, 48.7%), mp (decomposition): 198.5-205.0° C.: 1H NMR (500 MHz, CDCl$_3$) δ 8.51 (s, 1H), 7.91 (d, J=1.5 Hz, 1H), 7.74 (d, J=8.8 Hz, 1H), 7.72 (d, J=8.2 Hz, 2H), 7.55 (d, J=8.1 Hz, 2H), 7.44 (dd, J=9.0, 1.9 Hz, 1H), 7.31-7.25 (m, 2H), 7.22-7.17 (m, 3H), 3.91 (s, 2H), 3.23 (t, J=6.1 Hz, 2H), 3.02 (br s, 2H), 2.96-2.87 (m, 4H); ESI-MS [M+H]$^+$ calculated for C$_{27}$H$_{24}$BrClN$_3$O, 520.07; found 520.0.

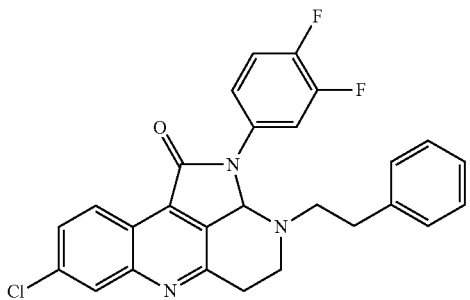 [SMILES: O=C1c2c3c(nc4cc(Cl)ccc24)CCN(CCc2ccccc2)C3N1c1ccc(F)c(F)c1]

8-Chloro-2-(3,4-difluorophenyl)-3-phenethyl-2a,3,4,5-tetrahydrobenzo[b]pyrrolo[4,3,2-de][1,6]naphthyridin-1(2H)-one (172)

(1.2 mg, 3.8%): 1H NMR (500 MHz, CDCl$_3$) δ 8.75 (d, J=8.8 Hz, 1H), 8.15 (d, J=2.1 Hz, 1H), 7.92 (ddd, J=12.5, 7.1, 2.7 Hz, 1H), 7.70-7.66 (m, 1H), 7.64 (dd, J=8.8, 2.1 Hz, 1H), 7.18-7.08 (m, 3H), 6.94-6.91 (m, 2H), 5.74 (s, 1H), 3.77 (dd, J=14.8, 7.2 Hz, 1H), 3.69-3.60 (m, 1H), 3.25 (dd, J=18.5, 7.2 Hz, 1H), 3.20-3.11 (m, 1H), 2.71-2.56 (m, 2H), 2.35-2.25 (m, 1H), 2.03-1.94 (m, 1H); ESI-MS [M+H]$^+$ m/z calcd for C$_{27}$H$_{21}$ClF$_2$N$_3$O, 476.13; found, 476.1.

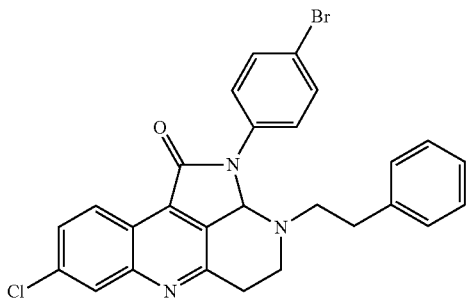 [SMILES: O=C1c2c3c(nc4cc(Cl)ccc24)CCN(CCc2ccccc2)C3N1c1ccc(Br)cc1]

2-(4-Bromophenyl)-8-chloro-3-phenethyl-2a,3,4,5-tetrahydrobenzo[b]pyrrolo[4,3,2-de][1,6]naphthyridin-1(2H)-one (175)

A suspension of amide 171 (28 mg, 0.054 mmol, 1 equiv) in dichloroethane (538 μL) was stirred at room temperature. Red mercuric oxide (9.4 mg, 0.044 mmol, 1.5 equiv) was added followed by iodine (17 mg, 0.081 mmol, 1.5 equiv). The reaction was kept out of the light and stirred for 2.5 h. The suspension was diluted with dichloromethane (5 mL), filtered, and the filtrate quenched with 5% sodium thiosulfate solution (5 mL). The organic layer was collected and washed once with water (5 mL), dried over sodium sulfate, decanted, and concentrated. The residue was chromatographed (1:3 ethyl acetate/hexane) to produce 175 as a solid with 12% impurity (15 mg, 55%), mp (decomposition): 173° C.: 1H NMR (500 MHz, CDCl$_3$) δ 8.73 (d, J=8.8 Hz, 1H), 8.13 (d, J=2.1 Hz, 1H), 7.79 (d, J=8.9 Hz, 2H), 7.62 (dd, J=8.8, 2.1 Hz, 1H), 7.47 (d, J=8.9 Hz, 2H), 7.15-7.11 (m, 3H), 6.89 (dd, J=6.6, 2.9 Hz, 2H), 5.76 (s, 1H), 3.75 (dd, J=14.9, 6.6 Hz, 1H), 3.62 (ddd, J=14.9, 10.3, 7.0 Hz, 1H), 3.24 (dd, J=18.7, 6.5 Hz, 1H), 3.14 (ddd, J=18.5, 10.2, 7.3 Hz, 1H), 2.63 (ddd, J=13.9, 8.5, 5.3 Hz, 1H), 2.56 (dt, J=13.8, 7.8 Hz, 1H), 2.30 (dt, J=12.8, 8.1 Hz, 1H), 1.97 (ddd, J=13.0, 8.0, 5.2 Hz, 1H); $^{13}$C NMR (126 MHz, CDCl$_3$) δ 166.80, 155.25, 150.31, 139.14, 137.06, 136.36, 133.35, 132.65, 132.06, 128.83, 128.51, 128.31, 128.28, 126.21, 124.96, 122.42, 120.34, 118.54, 75.43, 45.13, 44.37, 33.89, 25.69; ESI-MS [M+H]$^+$ m/z calcd for C$_{27}$H$_{22}$BrClN$_3$O, 518.06; found, 518.3.

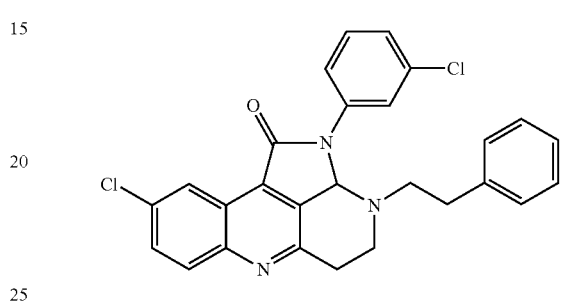

9-Chloro-2-(3-chlorophenyl)-3-phenethyl-2a,3,4,5-tetrahydrobenzo[b]pyrrolo[4,3,2-de][1,6]naphthyridin-1(2H)-one (176)

The title pyrrolinone was prepared from amide 193 (9.1 mg, 0.019 mmol, 1 equiv) by following the procedure for 175 except the reaction was stirred for 45 min. Chromatography (2:3 ethyl acetate/hexane) produced 176 as a solid with 32% impurity (4.2 mg, 46%), mp (decomposition): 138.9-152.1° C.: 1H NMR (500 MHz, CDCl$_3$) δ 8.81 (s, 1H), 8.08 (d, J=9.1 Hz, 1H), 8.06 (s, 1H), 7.85 (d, J=8.4 Hz, 1H), 7.73 (d, J=9.4 Hz, 1H), 7.35-7.28 (m, 2H), 7.24-7.18 (m, 3H), 7.17-7.07 (m, 1.5H), 6.91 (d, J=7.6 Hz, 2H), 5.81 (s, 1H), 4.39-4.26 (m, 1H), 4.01-3.94 (m, 1H), 3.72 (dd, J=14.8, 7.4 Hz, 1H), 3.68-3.60 (m, 1H), 3.24 (dd, J=18.9, 6.9 Hz, 1H), 3.14 (dt, J=18.2, 8.6 Hz, 1H), 2.69-2.53 (m, 2H), 2.39-2.26 (m, 2H), 1.99 (dt, J=13.4, 6.7 Hz, 1H); ESI-MS [M+H]$^+$ m/z calcd for C$_{27}$H$_{22}$Cl$_2$N$_3$O, 474.11; found, 474.2.

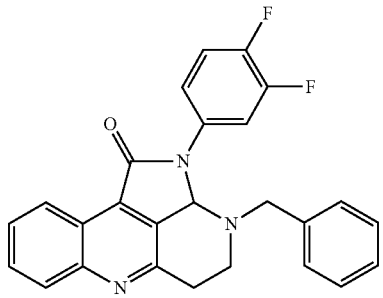 [SMILES: O=C1c2c3c(nc4ccccc24)CCN(Cc2ccccc2)C3N1c1ccc(F)c(F)c1]

3-Benzyl-2-(3,4-difluorophenyl)-2a,3,4,5-tetrahydrobenzo[b]pyrrolo[4,3,2-de][1,6]naphthyridin-1(2H)-one (177)

The title pyrrolinone was prepared from amide 66 (75 mg, 0.18 mmol, 1 equiv) by following the procedure for 175 except the reaction was stirred for 1.5 h. Chromatography (1:1 ethyl acetate/hexane) produced 177 as an orange solid (47.5 mg, 63%), mp (decomposition): 163.3-165.9° C.: 1H NMR (500 MHz, CDCl$_3$) δ 8.84 (dd, J=8.2, 1.0 Hz, 1H), 8.19 (d, J=8.5 Hz, 1H), 8.10 (ddd, J=12.6, 7.2, 2.7 Hz, 1H), 7.87-7.84 (m, 1H), 7.84 (ddd, J=8.4, 7.0, 1.6 Hz, 1H), 7.71 (ddd, J=8.2, 7.0, 1.2 Hz, 1H), 7.28-7.19 (m, 4H), 7.08-7.05 (m, 1H), 5.92 (s, 1H), 3.55 (ddd, J=15.0, 10.4, 7.3 Hz, 1H), 3.44 (ddd, J=14.8, 7.3, 1.1 Hz, 1H), 3.31 (d, J=13.3 Hz, 1H), 3.22 (ddd, J=18.8, 7.0, 1.2 Hz, 1H), 3.13 (ddd, J=18.7, 10.5, 7.4 Hz, 1H), 2.72 (d, J=13.3 Hz, 1H); $^{13}$C NMR (126 MHz, CDCl$_3$) δ 167.12, 153.78, 150.14 (dd, J=247.2, 13.1 Hz), 150.09, 147.60 (dd, J=247.2, 12.7 Hz), 136.87, 134.81 (dd, J=8.4, 3.4 Hz), 132.80, 132.43, 130.46, 129.26, 128.64, 128.39, 128.02, 127.44, 123.79, 122.05, 117.28 (d, J=18.2 Hz), 116.30 (dd, J=5.8, 3.7 Hz), 110.20 (d, J=22.0 Hz), 75.41, 47.43, 44.70, 25.65; $^{19}$F NMR (470 MHz, CDCl$_3$) δ−135.29−−135.41 (m), −141.40 (dddd, J=21.4, 10.5, 7.3, 3.9 Hz); ESI-MS [M+H]$^+$ m/z calcd for C$_{26}$H$_{20}$F$_2$N$_3$O, 428.15; found, 428.1.

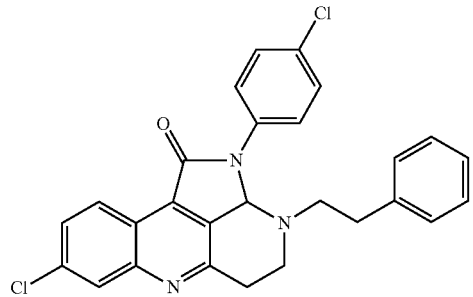

8-Chloro-2-(4-chlorophenyl)-3-phenethyl-2a,3,4,5-tetrahydrobenzo[b]pyrrolo[4,3,2-de][1,6]naphthyridin-1(2H)-one (179)

The title pyrrolinone was prepared from amide 165 (22 mg, 0.046 mmol, 1 equiv) by following the procedure for 175 except the reaction was stirred for 45 min. Chromatography (2:3 ethyl acetate/hexane) produced 179 as a solid with 16% impurity (9.6 mg, 44%), mp (decomposition): 130° C.; $^1$H NMR (500 MHz, CDCl$_3$) δ 8.73 (d, J=8.8 Hz, 1H), 8.13 (s, 1H), 7.84 (d, J=8.9 Hz, 2H), 7.62 (d, J=8.8 Hz, 1H), 7.33 (d, J=8.9 Hz, 2H), 7.17-7.09 (m, 3H), 6.92-6.83 (m, 2H), 5.77 (s, 1H), 3.74 (dd, J=15.0, 7.3 Hz, 1H), 3.62 (ddd, J=15.8, 10.2, 7.2 Hz, 1H), 3.24 (dd, J=18.9, 7.0 Hz, 1H), 3.14 (ddd, J=18.7, 10.3, 7.5 Hz, 1H), 2.63 (ddd, J=13.7, 8.6, 5.3 Hz, 1H), 2.56 (dt, J=15.2, 7.8 Hz, 1H), 2.30 (dt, J=12.4, 8.1 Hz, 1H), 1.98 (ddd, J=13.2, 8.0, 5.4 Hz, 1H); $^{13}$C NMR (126 MHz, CDCl$_3$) δ 166.82, 155.26, 150.28, 139.14, 136.53, 136.37, 133.37, 132.67, 130.71, 129.12, 128.83, 128.51, 128.30, 128.25, 126.21, 124.97, 122.20, 120.35, 75.50, 45.16, 44.43, 33.90, 29.71 (grease), 25.70; ESI-MS [M+H]$^+$ m/z calcd for C$_{27}$H$_{22}$Cl$_2$N$_3$O, 474.11; found, 474.1.

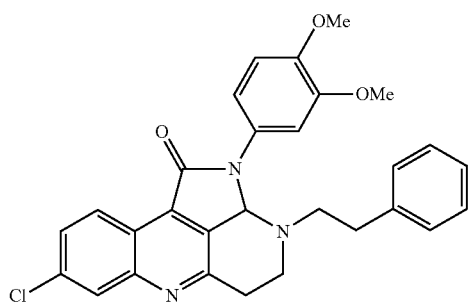 [SMILES: COc1ccc(N2C(=O)c3c4c(nc5cc(Cl)ccc35)CCN(CCc3ccccc3)C42)cc1OC]

8-Chloro-2-(3,4-dimethoxyphenyl)-3-phenethyl-2a,3,4,5-tetrahydrobenzo[b]pyrrolo[4,3,2-de][1,6]naphthyridin-1(2H)-one (178)

The title pyrrolinone was prepared from amide 166 (22 mg, 0.044 mmol, 1 equiv) by following the procedure for 175 except the reaction was stirred for 45 min. Chromatography (1:1 ethyl acetate/hexane) produced 178 as a solid (8.1 mg, 37%), mp (decomposition): 150.2° C.: 1H NMR (500 MHz, CDCl$_3$) δ 8.75 (d, J=8.8 Hz, 1H), 8.13 (d, J=2.1 Hz, 1H), 7.61 (dd, J=8.8, 2.1 Hz, 1H), 7.58 (d, J=2.4 Hz, 1H), 7.31-7.24 (m, 2H), 7.18-7.09 (m, 2H), 6.94-6.85 (m, 3H), 5.74 (s, 1H), 3.93 (s, 3H), 3.91 (s, 3H), 3.70 (dd, J=14.4, 6.6 Hz, 1H), 3.63-3.54 (m, 1H), 3.25 (dd, J=18.8, 5.5 Hz, 1H), 3.13 (ddd, J=18.5, 10.4, 7.4 Hz, 1H), 2.68 (ddd, J=14.6, 9.4, 5.3 Hz, 1H), 2.60 (ddd, J=13.4, 8.9, 6.4 Hz, 1H), 2.41 (ddd, J=12.4, 8.9, 6.3 Hz, 1H), 2.13-2.02 (m, 1H); $^{13}$C NMR (126 MHz, CDCl$_3$) δ 167.08, 155.33, 150.27, 149.08, 147.10, 139.18, 136.26, 133.66, 132.98, 131.28, 128.65, 128.48, 128.31, 128.20, 126.20, 125.05, 120.45, 114.24, 111.20, 106.46, 76.21, 56.03, 45.75, 34.08, 26.32; ESI-MS [M+H]$^+$ m/z calcd for C$_{29}$H$_{27}$Cl$_1$N$_3$O$_3$, 500.17; found, 500.2.

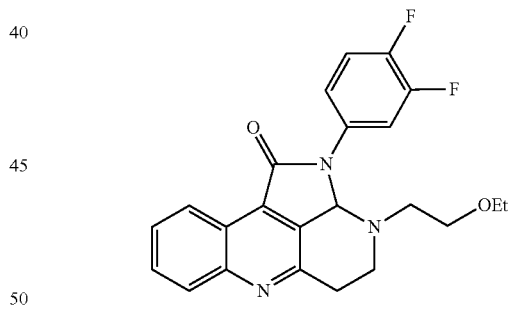

2-(3,4-Difluorophenyl)-3-(2-ethoxyethyl)-2a,3,4,5-tetrahydrobenzo[b]pyrrolo[4,3,2-de][1,6]naphthyridin-1(2H)-one (180)

The title pyrrolinone was prepared from amide 103 (40 mg, 0.97 mmol, 1 equiv) by following the procedure for 175. Chromatography (1:1 to 2:1 ethyl acetate/hexane) produced 180 as a yellow solid (23 mg, 58%): 1H NMR (500 MHz, CDCl$_3$) δ 8.82 (d, J=8.2 Hz, 1H), 8.16 (d, J=8.6 Hz, 1H), 8.11 (ddd, J=12.6, 7.2, 2.6 Hz, 1H), 7.86-7.79 (m, 2H), 7.69 (t, J=8.2 Hz, 1H), 7.26-7.20 (m, 1H), 5.75 (s, 1H), 3.87-3.80 (m, 1H), 3.71-3.63 (m, 1H), 3.37-3.30 (m, 4H), 3.25-3.20 (m, 2H), 2.27-2.21 (m, 1H), 1.97 (dt, J=13.4, 5.4 Hz, 1H), 1.09 (t, J=7.0 Hz, 3H); (partial)$^{13}$C NMR (126 MHz, CDCl$_3$) δ 167.40, 154.01, 150.00, 133.03, 132.34, 130.36, 129.23, 127.93, 123.75, 121.97, 117.23 (d, J=18.0 Hz), 116.93 (dd, J=5.9, 3.8 Hz), 110.78 (d, J=21.8 Hz), 76.00, 68.87, 66.41, 46.46, 42.57, 25.73, 15.03; $^{19}$F NMR (470 MHz, CDCl$_3$) δ −135.42 (ddd, J=21.4, 12.4, 8.6 Hz), −141.30 (dddd, J=21.6, 10.7, 7.3, 3.9 Hz); ESI-MS [M+H]$^+$ m/z calcd for C$_{23}$H$_{22}$F$_2$N$_3$O$_2$, 410.16; found, 410.4.

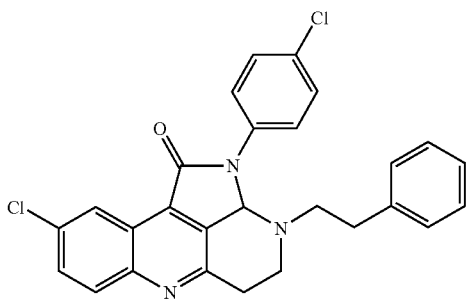 [SMILES: O=C1c2c3c(nc4ccc(Cl)cc24)CCN(CCc2ccccc2)C3N1c1ccc(Cl)cc1]

9-Chloro-2-(4-chlorophenyl)-3-phenethyl-2a,3,4,5-tetrahydrobenzo[b]pyrrolo[4,3,2-de][1,6]naphthyridin-1(2H)-one (181)

The title pyrrolinone was prepared from amide 168 (15.4 mg, 0.032 mmol, 1 equiv) by following the procedure for 175 except the reaction was stirred for 45 min. Chromatography (2:3 ethyl acetate/hexane) produced 181 as a solid (6.0 mg, 39%), mp (decomposition): 171.7-180.7° C.: 1H NMR (500 MHz, CDCl$_3$) δ 8.79 (d, J=2.4 Hz, 1H), 8.07 (d, J=9.1 Hz, 1H), 7.85 (d, J=8.9 Hz, 2H), 7.73 (dd, J=9.1, 2.4 Hz, 1H), 7.33 (d, J=8.9 Hz, 2H), 7.14 (dd, J=5.1, 1.9 Hz, 3H), 6.92-6.87 (m, 2H), 5.79 (s, 1H), 3.75 (dd, J=14.7, 6.7 Hz, 1H), 3.64 (ddd, J=14.8, 10.2, 7.2 Hz, 1H), 3.24 (dd, J=18.7, 7.0 Hz, 1H), 3.14 (ddd, J=18.7, 10.4, 7.5 Hz, 1H), 2.67-2.52 (m, 2H), 2.30 (dt, J=12.9, 8.4 Hz, 1H), 1.98 (ddd, J=13.0, 7.9, 5.3 Hz, 1H); $^{13}$C NMR (126 MHz, CDCl$_3$) δ 166.73, 154.15, 148.24, 139.13, 136.56, 134.11, 134.05, 131.87, 131.32, 130.66, 130.56, 129.12, 128.51, 128.30, 126.21, 122.85, 122.55, 122.09, 75.47, 75.45, 45.15, 44.35, 33.92, 25.61; ESI-MS [M+H]$^+$ m/z calcd for C$_{27}$H$_{22}$Cl$_2$N$_3$O, 474.11; found, 474.2.

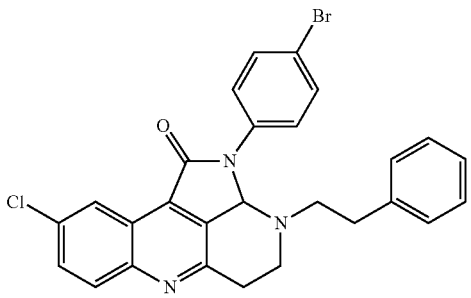 [SMILES: O=C1c2c3c(nc4ccc(Cl)cc24)CCN(CCc2ccccc2)C3N1c1ccc(Br)cc1]

2-(4-Bromophenyl)-9-chloro-3-phenethyl-2a,3,4,5-tetrahydrobenzo[b]pyrrolo[4,3,2-de][1,6]naphthyridin-1(2H)-one (182)

The title pyrrolinone was prepared from amide 194 (15 mg, 0.029 mmol, 1 equiv) by following the procedure for 175 except the reaction was stirred for 1.5 h. Chromatography (2:1 ethyl acetate/hexane) produced 182 as a solid (5.0 mg, 33%), mp (decomposition): 151.8-159.8° C.: 1H NMR (500 MHz, CDCl$_3$) δ 8.80 (d, J=2.3 Hz, 1H), 8.07 (d, J=9.1 Hz, 1H), 7.81 (d, J=9.0 Hz, 2H), 7.73 (dd, J=9.0, 2.4 Hz, 1H), 7.48 (d, J=9.0 Hz, 2H), 7.16-7.12 (m, 3H), 6.91-6.87 (m, 2H), 5.79 (s, 1H), 3.75 (ddd, J=15.0, 7.6, 1.5 Hz, 1H), 3.64 (ddd, J=15.1, 10.2, 7.0 Hz, 1H), 3.24 (ddd, J=18.8, 7.0, 1.5 Hz, 1H), 3.14 (ddd, J=18.6, 10.4, 7.5 Hz, 1H), 2.67-2.53 (m, 2H), 2.30 (dt, J=13.2, 8.3 Hz, 1H), 1.98 (ddd, J=13.0, 7.9, 5.3 Hz, 1H); ESI-MS [M+H]$^+$ m/z calcd for C$_{27}$H$_{22}$BrClN$_3$O, 518.06; found, 518.0.

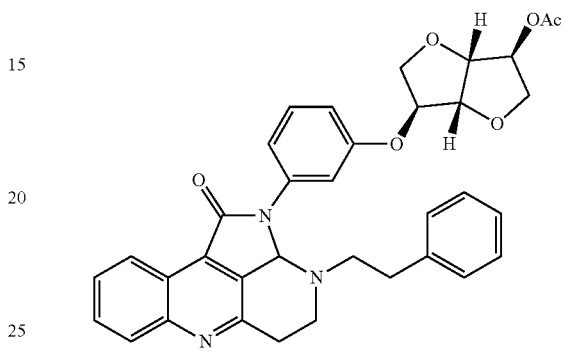

(3S,3aR,6S,6aR)-6-(3-(1-Oxo-3-phenethyl-2a,3,4,5-tetrahydrobenzo[b]pyrrolo[4,3,2-de][1,6]naphthyridin-2(1H)-yl)phenoxy)hexahydrofuro[3,2-b]furan-3-yl Acetate (183)

The title pyrrolinone was prepared from amide 147 (40 mg, 0.067 mmol, 1 equiv) by following the procedure for 175 except the reaction was stirred for 1 h. Chromatography (1:1 ethyl acetate/hexane to 100% ethyl acetate) produced 183 as a 1:1 mixture of diastereomers and a yellow oil (28 mg, 71%): 1H NMR (500 MHz, CDCl$_3$) δ 8.83 (ddd, J=8.3, 1.6, 0.7 Hz, 2H), 8.14 (d, J=8.5 Hz, 2H), 7.79 (ddd, J=8.5, 6.9, 1.5 Hz, 2H), 7.69-7.65 (m, 4H), 7.58 (dddd, J=15.1, 8.2, 2.1, 0.9 Hz, 2H), 7.34 (td, J=8.2, 1.5 Hz, 2H), 7.15-7.07 (m, 6H), 6.90 (dq, J=6.0, 1.6 Hz, 4H), 6.83 (dddd, J=8.2, 5.5, 2.5, 0.9 Hz, 2H), 5.83 (s, 1H), 5.81 (s, 1H), 5.24 (d, J=3.1 Hz, 2H), 4.86 (t, J=2.7 Hz, 1H), 4.81 (s, 1H), 4.79 (d, J=4.0 Hz, 2H), 4.72 (d, J=3.9 Hz, 2H), 4.14-4.07 (m, 6H), 4.05 (dt, J=10.7, 3.9 Hz, 2H), 3.95 (d, J=10.6 Hz, 2H), 3.71 (ddd, J=15.0, 7.5, 1.7 Hz, 2H), 3.67-3.59 (m, 2H), 3.25 (dd, J=18.5, 6.8 Hz, 2H), 3.15 (ddd, J=18.4, 10.3, 7.6 Hz, 2H), 2.80 (tetramethylurea, s, 2.3H), 2.69-2.53 (m, 4H), 2.36 (ddd, J=13.0, 9.3, 6.9 Hz, 2H), 2.07 (s, 3H), 2.06 (s, 3H); $^{13}$C NMR (126 MHz, cdcl$_3$) δ 169.95, 167.42, 167.38, 157.42, 157.39, 153.94, 153.92, 149.89, 139.67, 139.60, 139.32, 139.31, 133.44, 132.64, 130.25, 130.04, 129.10, 128.45, 128.25, 128.22, 127.80, 126.10, 126.07, 123.86, 122.09, 114.38, 114.13, 112.06, 111.97, 108.72, 108.45, 85.58, 81.14, 81.11, 81.09, 81.06, 77.67, 77.64, 77.61, 77.60, 75.69, 75.66, 75.50, 75.47, 72.56, 72.51, 72.47, 72.44, 45.65, 44.88, 44.76, 34.20, 25.93, 25.89, 20.90; ESI-MS [M+H]$^+$ m/z calcd for C$_{35}$H$_{34}$N$_3$O$_6$, 592.24; found, 592.4.

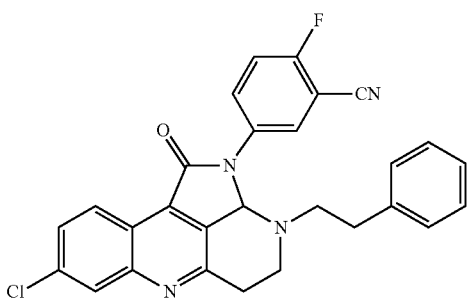 [SMILES: N#Cc1cc(N2C(=O)c3c4c(nc5cc(Cl)ccc35)CCN(CCc3ccccc3)C42)ccc1F]

5-(8-Chloro-1-oxo-3-phenethyl-2a,3,4,5-tetrahydrobenzo[b]pyrrolo[4,3,2-de][1,6]naphthyridin-2(1H)-yl)-2-fluorobenzonitrile (184)

The title pyrrolinone was prepared from amide 169 (22.2 mg, 0.046 mmol, 1 equiv) by following the procedure for 175 except the reaction was stirred for 1.5 h. Chromatography (1:1 ethyl acetate/hexane) produced 184 as a solid with 15% impurity (8.8 mg, 39%), mp (decomposition): 180° C.: 1H NMR (500 MHz, CDCl$_3$) δ 8.72 (d, J=8.6 Hz, 1H), 8.27-8.20 (m, 2H), 8.16 (s, 1H), 7.65 (d, J=8.3 Hz, 1H), 7.32 (s, 1H), 7.18-7.07 (m, 3H), 6.90 (s, 2H), 5.75 (s, 1H), 3.82 (dd, J=15.1, 7.3 Hz, 1H), 3.72-3.62 (m, 1H), 3.27 (dd, J=18.9, 6.7 Hz, 1H), 3.18 (dt, J=18.7, 8.9 Hz, 1H), 2.68-2.54 (m, 2H), 2.28-2.18 (m, 1H), 2.02-1.94 (m, 1H); $^{13}$C NMR (126 MHz, CDCl$_3$) δ 166.84, 159.75 (d, J=258.0 Hz), 155.13, 150.43, 139.17, 136.60, 135.03 (d, J=2.8 Hz), 132.94, 132.16, 129.09, 128.50, 128.43, 128.34, 126.38 (d, J=6.7 Hz), 126.32, 124.84, 124.23, 120.21, 116.82 (d, J=20.8 Hz), 113.68, 101.70 (d, J=16.4 Hz), 75.46, 44.70, 43.78, 33.63, 25.40; $^{19}$F NMR (470 MHz, CDCl$_3$) δ−111.14 (dt, J=8.8, 5.0 Hz); ESI-MS [M+H]$^+$ m/z calcd for C$_{28}$H$_{21}$ClFN$_4$O, 483.13; found, 483.1.

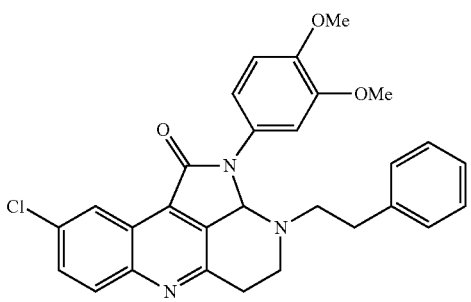 [SMILES: COc1ccc(N2C(=O)c3c4c(nc5ccc(Cl)cc35)CCN(CCc3ccccc3)C42)cc1OC]

9-Chloro-2-(3,4-dimethoxyphenyl)-3-phenethyl-2a,3,4,5-tetrahydrobenzo[b]pyrrolo[4,3,2-de][1,6]naphthyridin-1(2H)-one (185)

The title pyrrolinone was prepared from amide 170 (24.2 mg, 0.048 mmol, 1 equiv) by following the procedure for 175 except the reaction was stirred for 45 min. Chromatography (3:1 ethyl acetate/hexane) produced 185 as a solid (4.6 mg, 19%), mp (decomposition): 110.1-128.1° C.: 1H NMR (500 MHz, CDCl$_3$) δ 8.82 (d, J=2.2 Hz, 1H), 8.06 (d, J=9.1 Hz, 1H), 7.72 (dd, J=8.5, 1.9 Hz, 1H), 7.62 (d, J=2.4 Hz, 1H), 7.29 (dd, J=8.7, 2.5 Hz, 1H), 7.17-7.10 (m, 3H), 6.93-6.87 (m, 3H), 5.76 (s, 1H), 3.93 (s, 3H), 3.92 (s, 3H), 3.71 (dd, J=15.2, 7.2 Hz, 1H), 3.64-3.55 (m, 1H), 3.25 (dd, J=18.7, 6.7 Hz, 1H), 3.14 (ddd, J=18.1, 10.3, 7.5 Hz, 1H), 2.68 (ddd, J=14.4, 9.7, 5.6 Hz, 1H), 2.60 (dt, J=14.1, 7.7 Hz, 1H), 2.45-2.36 (m, 1H), 2.10-2.02 (m, 1H); $^{13}$C NMR (126 MHz, CDCl$_3$) δ 166.96, 154.22, 149.06, 148.20, 147.01, 139.18, 134.30, 133.93, 132.19, 131.33, 131.24, 130.48, 128.47, 128.30, 126.19, 122.89, 122.64, 113.98, 111.19, 106.28, 76.11, 56.03, 55.97, 45.52, 34.10, 29.71, 26.14; ESI-MS [M+H]$^+$ m/z calcd for C$_{29}$H$_{27}$Cl$_1$N$_3$O$_3$, 500.17; found, 500.3.

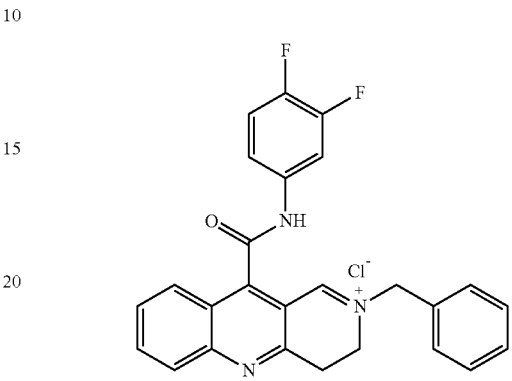

2-Benzyl-10-((3,4-difluorophenyl)carbamoyl)-3,4-dihydrobenzo[b][1,6]naphthyridin-2-ium (186)

A solution of pyrrolinone 177 (7.3 mg, 0.017 mmol, 1 equiv) in dioxane (170 μL) is stirred at room temperature. Hydrochloric acid in diethyl ether (2.0 M, 8 μL, 0.017 mmol, 1 equiv) was added, which caused a yellow solid to precipitate. The reaction was filtered giving 186 as a yellow solid; $^1$H NMR (500 MHz, CD$_3$OD) δ 9.37 (s, 1H), 8.18 (d, J=8.1 Hz, 1H), 8.17 (d, J=8.5 Hz, 1H), 8.07 (ddd, J=8.5, 6.9, 1.4 Hz, 1H), 7.93 (ddd, J=12.4, 7.3, 2.5 Hz, 1H), 7.81 (ddd, J=8.3, 6.9, 1.2 Hz, 1H), 7.57-7.54 (m, 2H), 7.49-7.43 (m, 2H), 7.44-7.39 (m, 1H), 7.35 (dt, J=9.9, 8.7 Hz, 1H), 5.39 (s, 2H), 4.35 (t, J=7.4 Hz, 2H), 3.65 (dioxane, s, 0.6H), 3.56 (t, J=7.5 Hz, 2H); $^{13}$C NMR (126 MHz, CDCl$_3$) δ 163.96, 161.70, 153.58, 151.05, 150.83, 148.57-148.19 (m), 135.22, 134.29, 130.28, 129.85, 129.57, 129.34, 129.13, 129.00, 127.04, 122.87, 117.15 (d, J=18.2 Hz), 116.54-116.28 (m), 114.28, 109.84 (d, J=22.2 Hz), 66.71, 64.01, 49.12, 28.81; $^{19}$F NMR (470 MHz, CD$_3$OD) δ−138.39 (ddd, J=21.1, 12.7, 8.7 Hz), −143.76 (dddd, J=21.4, 10.9, 7.2, 4.0 Hz); ESI-MS [M+H]$^+$ m/z calcd for C$_{26}$H$_{20}$F$_2$N$_3$O, 428.15; found, 428.1.

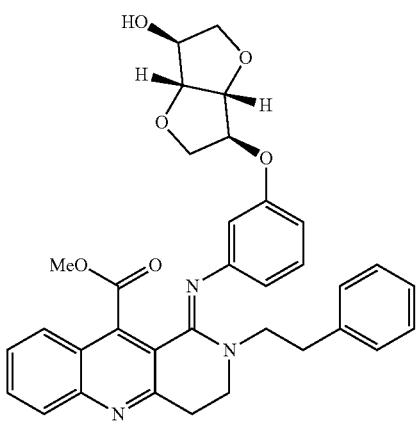 [SMILES: COC(=O)c1c2c(nc3ccccc13)CCN(CCc1ccccc1)/C2=N\c1cccc(O[C@H]2CO[C@H]3[C@@H]2OC[C@@H]3O)c1]

Methyl (Z)-1-(((3-(((3S,3aR,6S,6aR)-6-hydroxyhexahydrofuro[3,2-b]furan-3-yl)oxy)phenyl)imino)-2-phenethyl-1,2,3,4-tetrahydrobenzo[b][1,6]naphthyridine-10-carboxylate (187)

The structure of the title compound was not the expected product and was determined from the available data derived from the product of the following procedure. A solution of pyrrolinone 183 (25 mg, 0.042 mmol, 1 equiv) in methanol (1.5 mL) was stirred at room temperature. A solution of potassium carbonate (70 mg, 0.51 mmol, 12 equiv) in water (500 µL) is added and the mixture stirred for 16 h. The reaction is concentrated to 500 µL, diluted with water (5 mL), and extracted with dichloromethane (5×10 mL). The organic layers are combined, dried over sodium sulfate, decanted, and concentrated to an orange solid; $^1$H NMR (500 MHz, CDCl$_3$) δ 8.04 (d, J=8.5 Hz, 1H), 7.81 (d, J=8.4 Hz, 1H), 7.76 (ddd, J=8.4, 6.8, 1.4 Hz, 1H), 7.56 (ddd, J=8.3, 7.0, 1.2 Hz, 1H), 7.25-7.09 (m, 5H), 6.81 (d, J=6.8 Hz, 2H), 6.61 (d, J=8.4 Hz, 1H), 6.58 (dd, J=8.1, 2.2 Hz, 1H), 6.55 (t, J=1.8 Hz, 1H), 4.77 (s, 1H), 4.75 (d, J=3.8 Hz, 1H), 4.57 (d, J=3.8 Hz, 1H), 4.34 (s, 1H), 4.04-3.97 (m, 2H), 3.91 (s, 3H), 3.90-3.84 (m, 2H), 3.53 (t, J=6.0 Hz, 2H), 3.42-3.37 (m, 2H), 3.25 (t, J=6.2 Hz, 2H), 2.79 (tetramethylurea, s, 1.5H), 2.70 (t, J=7.9 Hz, 2H); $^{13}$C NMR (126 MHz, CDCl$_3$) δ 168.18, 157.62, 157.11, 151.44, 147.84, 145.72, 140.67, 138.17, 131.09, 129.82, 128.65, 128.60, 128.46, 127.22, 126.46, 125.86, 123.98, 122.77, 113.87, 108.30, 107.56, 87.86, 85.23, 80.97, 75.96, 74.50, 72.35, 53.41, 52.55, 49.19, 33.67, 33.47, 29.71; ESI-MS [M+H]$^+$ m/z calcd for C$_{35}$H$_{34}$N$_3$O$_6$, 592.24; found, 592.4.

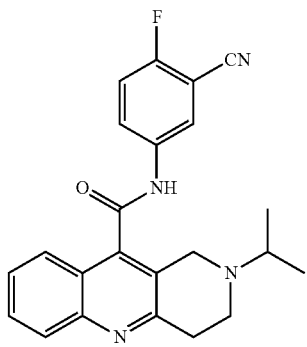 [SMILES: CC(C)N1CCc2nc3ccccc3c(C(=O)Nc3ccc(F)c(C#N)c3)c2C1]

N-(3-Cyano-4-fluorophenyl)-2-isopropyl-1,2,3,4-tetrahydrobenzo[b][1,6]naphthyridine-10-carboxamide (188)

A solution of amide 195 (210 mg, 0.47 mmol, 1 equiv) in dichloroethane (2.0 mL) and Trifluoroacetic acid (1.0 mL) was stirred at room temperature. After 1 h, the reaction was concentrated, and the residue weighed to determine the mass of residual trifluoroacetic acid assuming quantitative deprotection. The residue was dissolved in dichloroethane (3.1 mL). triethylamine (222 µL, 1.6 mmol) was added, followed by acetone (61 µL, 0.83 mmol, 1.8 equiv). After stirring for 1 h, sodium triacetoxyborohydride (199 mg, 0.94 mmol, 2 equiv) was added. After stirring for an additional 16 h, the reaction was quenched with saturated sodium bicarbonate (45 mL). The mixture was extracted with ethyl acetate (45 mL) and, the organic extracts dried over sodium sulfate, decanted, and concentrated. The residue was chromatographed (10:1 dichloromethane/methanol) to produce 188 as a light brown solid (80 mg, 49%), mp: 220.5-227° C.: $^1$H NMR (500 MHz, DMSO-d$_6$) δ 11.18 (s, 1H), 8.31 (dd, J=5.8, 2.7 Hz, 1H), 8.00-7.96 (m, 1H), 7.97 (d, J=7.3 Hz, 1H), 7.77 (d, J=8.4 Hz, 1H), 7.73 (ddd, J=8.4, 6.8, 1.4 Hz, 1H), 7.60-7.54 (m, 2H), 3.82 (s, 2H), 3.13 (t, J=6.0 Hz, 2H), 2.93 (hept, J=6.7 Hz, 1H), 2.88 (s, 2H), 1.02 (d, J=6.5 Hz, 6H); $^{13}$C NMR (126 MHz, DMSO-d$_6$) δ 165.51, 159.23 (d, J=253.1 Hz), 157.58, 146.51, 139.34, 135.85 (d, J=2.9 Hz), 129.82, 128.85, 127.72 (d, J=8.5 Hz), 127.25, 125.25, 124.88, 124.48, 122.85, 117.81 (d, J=20.8 Hz), 114.28, 100.68 (d, J=16.3 Hz), 53.61, 48.99 45.23, 34.14, 18.46, 18.14; $^{19}$F NMR (470 MHz, DMSO-d$_6$) δ−73.48 (s, trifluoroacetic acid), −113.65 (dt, J=9.6, 5.4 Hz); ESI-MS [M+H]$^+$ calculated for C$_{23}$H$_{22}$F$_1$N$_4$O, 389.45; found 389.1.

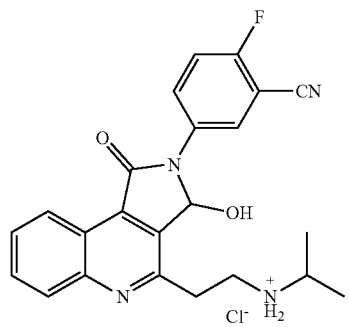 [SMILES: CC(C)NCCc1nc2ccccc2c2c1C(O)N(c1ccc(F)c(C#N)c1)C2=O ; [Cl-]]

N-(2-(2-(3-cyano-4-fluorophenyl)-3-hydroxy-1-oxo-2,3-dihydro-1H-pyrrolo[3,4-c]quinolin-4-yl)ethyl)propan-2-aminium Chloride (189)

A suspension of amide 188 (100 mg, 0.257 mmol, 1 equiv) in dichloroethane (2.57 mL) was stirred at room temperature. Red mercuric oxide (83.6 mg, 0.386 mmol, 1.5 equiv) was added followed by iodine (98 mg, 0.386 mmol, 1.5 equiv). The reaction was kept out of the light and stirred for 45 min. The suspension was diluted with dichloromethane (15 mL), filtered, and the filtrate quenched with 5% sodium thiosulfate solution (15 mL). The organic layer was collected and washed once with water (15 mL), dried over sodium sulfate, decanted, and concentrated. The residue was chromatographed (7.5% methanol in dichloromethane) to produce 189 as a solid (30 mg, 30%), mp (decomposition): 161.5-162.7° C.: $^1$H NMR (500 MHz, DMSO-d$_6$) δ 8.92 (d, J=8.3 Hz, 1H), 8.33 (dd, J=5.6, 2.7 Hz, 1H), 8.29-8.25 (m, 1H), 8.17 (d, J=8.5 Hz, 1H), 7.91 (t, J=7.7 Hz, 1H), 7.81 (t, J=7.6 Hz, 1H), 7.70 (t, J=9.0 Hz, 1H), 6.89 (s, 1H), 3.54-3.41 (m, 5H), 1.24 (d, J=2.8 Hz, 6H); $^{13}$C NMR (126 MHz, DMSO-d$_6$) δ 165.62, 154.36, 148.40, 136.88, 134.29 (d, J=3.0 Hz), 133.24, 131.23, 130.01 (d, J=7.6 Hz), 129.54, 129.12, 126.86, 123.57, 121.83, 117.89, 114.21, 100.90 (d, J=16.8 Hz), 81.34, 50.12, 19.29; $^{19}$F NMR (470 MHz, DMSO-d$_6$) δ−112.70−−112.81 (m); ESI-MS [M+H]$^+$ m/z calcd for C$_{23}$H$_{22}$FN$_4$O$_2$, 405.17; found, 405.2. Crystals for x-ray crystallography were grown by suspending 189 (≈10 mg) in approximately 2 mL of 1:1 toluene/dichloromethane. Methanol was added dropwise until the suspension cleared. The solution was filtered and slowly evaporated over five days. The resulting crystals were collected and dissolved in a similar manner as above. Slow evaporation of the solvent over one week resulted in crystals fit for crystallography.

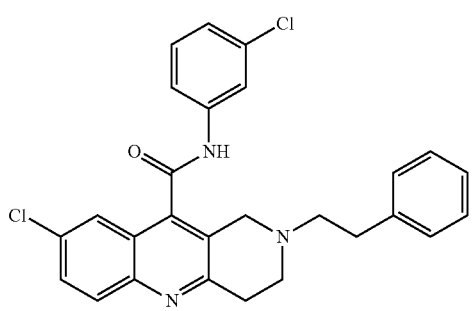 [SMILES: O=C(Nc1cccc(Cl)c1)c1c2c(nc3ccc(Cl)cc13)CCN(CCc1ccccc1)C2]

8-Chloro-N-(3-chlorophenyl)-2-phenethyl-1,2,3,4-tetrahydrobenzo[b][1,6]naphthyridine-10-carboxamide (193)

A suspension of acid 152 (50 mg, 0.14 mmol, 1 equiv) in dichloroethane (757 µL) was stirred under a nitrogen atmosphere at room temperature. Diisopropylethylamine (26 µL, 0.16 mmol, 1.2 equiv) is added, which cleared the suspension, followed by TCFH (57 mg, 0.20 mmol, 1.5 equiv). After 2 h, 3-chloroaniline (22 µL, 0.20 mmol, 1.5 equiv) was added, and the reaction is stirred for an additional 16 h. The reaction was diluted with dichloromethane (10 mL) and the washed saturated sodium bicarbonate (2×10 mL). The organic layer was dried over sodium sulfate, decanted, and concentrated. The residue was chromatographed (ethyl acetate), which produced a solid contaminated with 20% tetramethylurea (13 mg, 20%), mp (decomposition): 105.8-110.7° C.: 1H NMR (500 MHz, CDCl$_3$) δ 8.96 (s, 1H), 8.04 (q, J=1.6 Hz, 2H), 7.76 (d, J=9.0 Hz, 1H), 7.70 (d, J=8.1 Hz, 1H), 7.66 (s, 1H), 7.52 (ddd, J=9.2, 2.0, 1.4 Hz, 1H), 7.38 (td, J=8.1, 1.3 Hz, 1H), 7.29-7.22 (m, 3H), 7.22-7.16 (m, 3H), 3.79 (s, 2H), 3.14 (t, J=6.0 Hz, 2H), 2.98-2.85 (m, 4H), 2.85-2.80 (m, 2H), 2.67 (tetramethylurea, s, 3H); $^{13}$C NMR (126 MHz, cdcl$_3$) δ 164.26, 157.10, 144.63, 139.63, 138.83, 138.00, 135.10, 133.07, 130.86, 130.37, 129.65, 128.63, 128.48, 126.25, 125.47, 125.31, 123.16, 123.03, 120.06, 117.82, 59.58, 53.12, 49.80, 38.48 (tetramethylurea), 33.48, 33.09; ESI-MS [M+H]$^+$ calculated for $C_{27}H_{24}Cl_2N_3O$, 476.12; found 476.0.

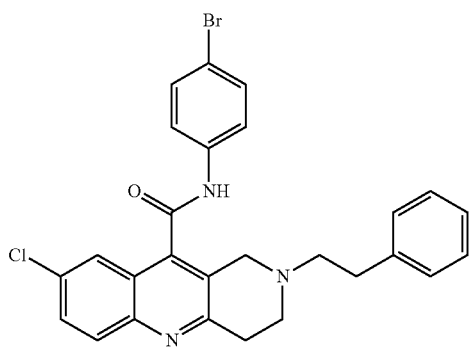 [SMILES: O=C(Nc1ccc(Br)cc1)c1c2c(nc3ccc(Cl)cc13)CCN(CCc1ccccc1)C2]

N-(4-Bromophenyl)-8-chloro-2-phenethyl-1,2,3,4-tetrahydrobenzo[b][1,6]naphthyridine-10-carboxamide (194)

A suspension of acid 152 (50 mg, 0.14 mmol, 1 equiv) in dichloroethane (757 µL) was stirred under a nitrogen atmosphere at room temperature. Diisopropylethylamine (26 µL, 0.16 mmol, 1.2 equiv) is added, which cleared the suspension, followed by TCFH (57 mg, 0.20 mmol, 1.5 equiv). After stirring for 2 h, 4-bromoaniline (35 mg, 0.20 mmol, 1.5 equiv) was added, and the reaction is stirred for an additional 16 h. The reaction was diluted with dichloromethane (10 mL) and the washed saturated sodium bicarbonate (2×10 mL). The organic layer was dried over sodium sulfate, decanted, and concentrated. The residue was chromatographed (ethyl acetate) producing a solid contaminated with 32% tetramethylurea. (35 mg, 49.3%), mp (decomposition): 198.5-205.0° C.: 1H NMR after column (500 MHz, CDCl$_3$) δ 8.86 (s, 1H), 7.82 (d, J=9.1 Hz, 1H), 7.75-7.70 (m, 3H), 7.58-7.51 (m, 3H), 7.30-7.23 (m, 2H), 7.21-7.16 (m, 3H), 3.93 (s, 2H), 3.22 (t, J=6.4 Hz, 2H), 3.03 (br s, 2H), 2.91 (s, 4H), 2.71 (tetramethylurea, s, 5.8H); $^{13}$C NMR after column (126 MHz, cdcl$_3$) δ 164.14, 156.24, 144.97, 138.98, 138.43, 136.61, 133.11, 132.29, 130.91, 129.99, 128.62, 128.57, 126.45, 124.44, 123.24, 123.21, 121.60, 118.01, 59.46, 53.09, 49.96, 38.52 (tetramethylurea), 33.13, 32.71; ESI-MS [M+H]$^+$ calculated for $C_{27}H_{24}BrClN_3O$, 520.07; found 520.0.

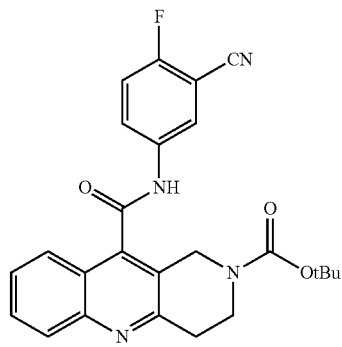 [SMILES: CC(C)(C)OC(=O)N1CCc2nc3ccccc3c(C(=O)Nc3ccc(F)c(C#N)c3)c2C1]

Tert-Butyl 10-((3-cyano-4-fluorophenyl)carbamoyl)-3,4-dihydrobenzo[b][1,6]naphthyridine-2(1H)-carboxylate (195)

A suspension of acid 85 (500 mg, 1.52 mmol, 1 equiv) in dichloroethane (8.5 mL) was stirred at room temperature under a nitrogen atmosphere. Diisopropylethylamine (298 µL, 1.83 mmol, 1.2 equiv) was added, which cleared the suspension. TCFH (641 mg, 2.28 mmol, 1.5 equiv) was added and the reaction was stirred for 2 h. 4-fluoro-3-cyanoaniline (311 mg, 2.28 mmol, 1.5 equiv) was added and the reaction was stirred for 17 h. The solution was diluted in dichloromethane (15 mL) and washed with saturated sodium bicarbonate (15 mL). The organic layer was diluted with toluene (15 mL), washed with water (3×15 mL), dried over sodium sulfate, decanted, and concentrated. The residue was chromatographed (3:1 ethyl acetate/hexane) producing a solid contaminated with tetramethylurea. The solid was dissolved in isopropyl acetate (50 mL) and washed with 25% w/w ammonium chloride (2×30 mL) and once with water (30 mL). The organic layer was then dried over sodium sulfate, decanted, and concentrated to produce 195 as a light brown solid (423 mg, 62%), mp: 188.4-190.1° C.: 1H NMR (500 MHz, CDCl3) δ $^1$H NMR 9.73 (br s, 1H), 8.26 (s, 1H), 8.14-8.06 (m, 1H), 7.93 (d, J=8.5 Hz, 1H), 7.85 (d, J=8.4 Hz, 1H), 7.70 (t, J=7.7 Hz, 1H), 7.54 (t, J=7.6 Hz, 1H), 7.26 (d, J=16.3 Hz, 1H), 4.64 (br s, 2H), 3.63 (br s, 2H), 3.06 (s, 2H), 1.35 (s, 9H); $^{13}$C NMR (126 MHz, Chloroform-d) δ 164.31, 159.76 (d, J=260.0 Hz), 156.39, 155.33, 138.53, 134.85, 130.45, 128.16 (d, J=5.9 Hz), 127.68, 126.20 (d, J=8.0 Hz), 124.61, 124.02, 123.64, 122.93, 117.16 (d, J=24.3 Hz), 113.47, 101.81 (d, J=23.3 Hz), 95.20, 81.12, 42.79, 41.57, 32.54, 28.23; $^{19}$F NMR (470 MHz, CDCl$_3$) δ −110.75; ESI-MS [M+H]$^+$ calculated for C$_{25}$H$_{24}$FN$_4$O$_3$, 447.48; found 447.1.

Example 3: Experimental

In vitro evaluation of anti-malarial activities of compound 2-Benzyl-N-(3,4-difluorophenyl)-1,2,3,4-tetrahydrobenzo[b][1,6]naphthyridine-10-carboxamide (66) and 3-Benzyl-2-(3,4-difluorophenyl)-2a,3,4,5-tetrahydrobenzo[b]pyrrolo[4,3,2-de][1,6]naphthyridin-1(2H)-one (177) was conducted.

Compound 66

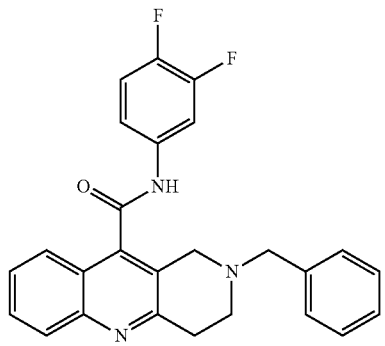

Compound 177

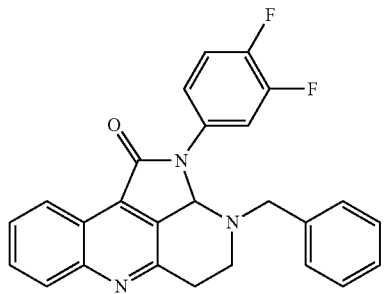

Assays using human blood cells infected with *Plasmodium falciparum*: (Pf) parasites, both wild-type strains as well as mutant drug-resistant strains, were performed as described below. Wild-type strains used were aatB Pf (Dd2 strain) and Pf (Dd2 strain). Mutant strains used were proguanil resistant attb Pf (Dd2 strain), dihydroorotate dehydrogenase (DHODH) deficient aatB Pf (Dd2 strain), and DHODH deficient and proguanil resistant Pf (Dd2 strain).

*P. falciparum* Asexual Blood Stage (ABS) Assay Protocol

Compounds 66 and 177 were tested for activity against symptomatic parasite blood stages of *Plasmodium falciparum* (DD2 strain) ("Pf Dd2") by using an asexual blood stage assay adapted from Plouffe D et al (2008) "In silico activity profiling reveals the mechanism of action of antimalarials discovered in a high-throughput screen." Proc Natl Acad Sci USA. 2008 Jul. 1; 105(26):9059-64.

Each wild type and mutant strain *P. falciparum* Dd2 strain was cultured in Complete Medium (RPMI 1640 Medium with L-Glutamine, 0.05 mg/ml Gentamicin, 0.014 mg/ml Hypoxanthine, 38.4 mM HEPES, 0.2% Sodium bicarbonate, 0.2% Glucose, 3.4 mM NaOH, 4.3% Human Serum, 0.2% Albumax) supplemented with 5% hematocrit until parasitemia reached 3-8%. Parasitemia was estimated by blood smear Giemsa stain and visual inspection under the microscopic.

The screening plate was prepared by centrifuging for parasite culture for 5 min at 800×g at RT (low brake) and removing supernatant. A parasite suspension was prepared with 0.3% parasitemia and 4% hematocrit in screening medium (SM). The suspension was gassed with a gas mixture of 1% oxygen, 3% carbon dioxide, 96% nitrogen and stored at 37° C. for until ready to use. 50 nl of 1 mM compound in DMSO was prespotted into 1536 well plates (final drug conc. of 12.5 μM, final DMSO conc. of 0.625%) with the acoustic dispenser ATS. Controls were Artemisinin, Chloroquine, and DMSO. 8 μl of SM was dispensed into 1,536-well, black, clear-bottom plates (Greiner) using the MultiFlo™ Microplate dispenser (BioTek) (final parasitemia of 0.3% and 2.5% hematocrit in SM). The plates were incubated at 37° C. for 72 h with water-soaked tissue in a closed ziploc bag gassed with 1% oxygen, 3% carbon dioxide, 96% nitrogen.

2 μl of detection reagent mixture (10×SYBR Green I (Invitrogen) in Lysis buffer (20 mM Tris/HCl, 5 mM EDTA, 0.16% Saponin wt/vol, 1.6% Triton X vol/vol) was added. Assay plates were read from the bottom by using the 2104 EnVision® Multilabel Reader (PerkinElmer) (485 nm excitation, 530 nm emission). The results are presented in Table 5 below.

TABLE 5

| | *P. falciparum* (Pf) (Dd2 Strain) Asexual Blood Stage Assay | | | | |
|---|---|---|---|---|---|
| Compound | Wild-Type attB Pf Dd2 IC$_{50}$ (uM) | Proguanil resistant attB Pf Dd2 IC$_{50}$ (uM) | DHODH deficient Pf Dd2 mutant IC$_{50}$ (uM) | DHODH deficient + Proguanil resistant Pf Dd2 IC$_{50}$ (uM) | Pf Dd2 IC$_{50}$ (uM) |
| 66 | 0.0565 | 0.0699 | 0.0301 | 0.028 | 0.302 |
| 177 | 0.00895 | 0.0113 | 0.0060 | 0.0103 | 0.0063 |

Compound 177 exhibited outstanding potency against wild-type attB Pf, with IC$_{50}$=0.00895 μM, whereas the related compound 66 showed IC$_{50}$=0.0556 μM. Compound 177 showed undiminished potency against a proguanil resistant attB mutant strain as well as a dihydroorotate dehydrogenase (DHODH) deficient mutant, indicating that the pyrrolidinone mechanism in Pf likely does not involve inhibition of mitochondrial electron transport.

Example 4: Experimental

Compounds 66 and 177 were tested for activity against sporozoite infection of liver cells as well the viability of liver schizonts of the murine *Plasmodium berghei* species transformed with Luciferase by using an assay adapted from S. Swann et al. (2016) High-Throughput Luciferase-Based Assay for the Discovery of Therapeutics That Prevent Malaria. ACS Infectious Diseases 2: 4. 281-293 (2016).

*P. berghei* Luciferase Liver Stage Assay Protocol

Compounds 66 and 177 were tested for activity against sporozoite infection of liver cells of the murine *Plasmodium berghei* species transformed with Luciferase by using the following *P. berghei* Luciferase liver stage assay.

Hepatic human transformed cells (HepG2) pre-treated for 18 hours with either compound 66 or 177 were infected with freshly dissected *P. berghei* Luciferase sporozoites. After another 48 hours of incubation with the compound, the viability of *P. berghei* exoerythrocytic forms (EEF) was measured by bioluminescence.

*Plasmodium berghei* Luciferase sporozoites were obtained by dissection of infected *A. stephensi* mosquito salivary glands supplied by the New York University Insectary. Dissected salivary glands were homogenized in a glass tissue grinder and filtered twice using Steriflip Vacuum-Driven Filtration System (20 μm pore size, Millipore) and counted using a hemocytometer. The sporozoites were kept on ice until needed.

HepG2-A16-CD81EGFP cells were stably transformed to express a GFP-CD81 fusion protein (S. Yalaoui et al., Hepatocyte permissiveness to *Plasmodium* infection is conveyed by a short and structurally conserved region of the CD81 large extracellular domain. PLoS Pathog. 4, e1000010 (2008); O. Silvie et al, Hepatocyte CD81 is required for *Plasmodium falciparum* and *Plasmodium yoelii* sporozoite infectivity. Nat. Med. 9, 93 (2003)). The transformed HepG2-A16-CD81EGFP cells were cultured at 37° C. in 5% $CO_2$ in DMEM (Invitrogen, Carlsbad, USA) supplemented with 10% FCS, 0.29 mg/ml glutamine, 100 units penicillin and 100 μg/ml streptomycin.

Because of the difficulties associated with human parasites able to infect immortal liver cell lines, the rodent model *P. berghei* was used. *P. berghei* is able to infect human hepatocarcinoma HepG2 cells expressing the tetraspanin CD81 receptor (S. Yalaoui et al 2008; O. Silvie et al. 2003). $3 \times 10^3$ HepG2-A16-CD81EGFP cells in 5 μl of medium ($2 \times 10^5$ cells/ml, 5% FBS, 5× Pen/Strep/Glu) were seeded in 1536-well plates (Greiner BioOne white solid bottom custom GNF mold) 20-26 hours prior to the actual infection. 18 hours prior to infection, 50 nl of compound in DMSO (0.5% final DMSO concentration per well) was transferred with a PinTool (GNF Systems) into the assay plates (10 μM final concentration). Atovaquone (10 μM) and 0.5% DMSO were used as positive and negative controls, respectively.

*P. berghei* Luciferase sporozoites were freshly dissected from infected *A. stephensi* mosquito salivary glands and filtered twice through a 40 μm nylon pore cell strainer. The sporozoites were re-suspended in media, counted in a hemocytometer and their final concentration adjusted to 200 sporozoites per μl. Also, penicillin and streptomycin were added at 5×-fold increased concentration for a final 5×-fold increased concentration in the well. The HepG2-A16-CD81EGFP cells were then infected with $1 \times 10^3$ sporozoites per well (5 μl) with a single tip Bottle Valve liquid handler (GNF), and the plates spun down at 37° C. for 3 minutes in an Eppendorf 5810 R centrifuge with a centrifugal force of 330× on lowest acceleration and brake setting. After incubation at 37° C. for 48 hours, the EEF growth was quantified by a bioluminescence measurement. The increased antibiotic concentration did not interfere with the parasite or HepG2- A16-CD81EGFP growth. Atovaquone and naive wells were used as controls on each plate. The compounds were screened in a 12-point serial dilution to determine their $IC_{50}$ values.

Media was removed by spinning the inverted plates at 150×g for 30 seconds. 2 μl BrightGlo (Promega) was dispensed with the MicroFlo (BioTek) liquid handler. Immediately after addition of the luminescence reagent, the plates were read by the Envision Multilabel Reader (PerkinElmer). $IC_{50}$ values were obtained by using the normalized bioluminescence intensity and a non-linear variable slope four parameter regression curve fitting model in Prism 6 (GraphPad Software Inc).

Compound 177 showed activity and no toxicity against sporozoite infection of liver cells of the murine *Plasmodium berghei* species transformed with Luciferase with $IC_{50}=>12.5$ μM, whereas the related compound 66 showed activity and no toxicity with $IC_{50}=>50.0$ μM.

HepG2 Cytotoxicity Bioluminescence Assay Protocol

Compounds 66 and 177 were tested for viability of liver schizonts of the murine *Plasmodium berghei* species transformed with Luciferase by using the following assay adapted and modified from S. Swann et al. (2016) High-Throughput Luciferase-Based Assay for the Discovery of Therapeutics That Prevent Malaria. ACS Infectious Diseases 2: 4. 281-293 (2016), but with the removal of the infection methods. The CellTiter-Glo® ° (Promega Corp., Madison WI) is a method to determine the number of viable cells in culture based on quantitation of the ATP present, which signals the presence of metabolically active cells.

HepG2-A16-CD81EGFP cells were stably transformed to express a GFP-CD81 fusion protein (S. Yalaoui et al., Hepatocyte permissiveness to *Plasmodium* infection is conveyed by a short and structurally conserved region of the CD81 large extracellular domain. PLoS Pathog. 4, e1000010 (2008); O. Silvie et al, Hepatocyte CD81 is required for *Plasmodium falciparum* and *Plasmodium yoelii* sporozoite infectivity. Nat. Med. 9, 93 (2003)). The transformed HepG2-A16-CD81EGFP cells were cultured at 37° C. in 5% $CO_2$ in DMEM (Invitrogen, Carlsbad, USA) supplemented with 10% FCS, 0.29 mg/ml glutamine, 100 units penicillin and 100 μg/ml streptomycin.

$3 \times 10^3$ HepG2-A16-CD81EGFP cells in 5 μl of medium ($2 \times 10^5$ cells/ml, 5% FBS, 5× Pen/Strep/Glu) were seeded in 1536-well plates (Greiner BioOne white solid bottom custom GNF mold) 20-26 hours prior to the actual infection. 24 hours prior to infection, 50 nl of compound in DMSO (0.5% final DMSO concentration per well) was transferred with acoustic transfer machine (ATS) into the assay plates (10 μM-50 μM final concentration). Puromycin (25 μM) and 0.5% DMSO were used as positive and negative controls, respectively.

5 μl of the HepG2 screening media were dispensed into each well of the 1536 plate format using the BioTek MultiFlo FX Multi-Mode Cell Dispenser and a 5 μl BioTek Liquid Handling MicroFlo cassette. This step was to maintain equal concentrations of compounds with the Pb-Luc infected plates that were performed in parallel with this assay (*P. berghei*-Luciferase Liver Stage Bioluminescence Assay). After incubation at 37° C. for 48 hours, the cell viability was quantified by bioluminescence measurement. The increased antibiotic concentration did not interfere with the HepG2- A16-CD81EGFP growth. Puromycin and naive wells were used as controls on each plate. The compounds were screened in a 12 point serial dilution to determine their $IC_{50}$ values.

Media was removed by spinning the inverted plates at 150 RCF for 1 minute. CellTiter-Glo® reagent (Promega Corp., Madison WI) was prepared following manufacturer instructions and diluted with DI H2O 1:1 (final solution is 50% CellTiterGlo® reagent in DI H2O). 2 μl of CellTiter-Glo® reagent was dispensed with the MicroFlo (BioTek) liquid handler and a designated BioTek Liquid Handling MicroFlo 1 μl cassette. Immediately after addition of the CellTiter-Glo® reagent, the plates were read by the Envision Multilabel Reader (PerkinElmer).

Compound 66 showed no toxicity below 50 uM, and compound 177 had no toxicity below 12.5 uM. Both compounds 66 and 177 showed acceptable levels of cell-based toxicity.

The foregoing description of the specific embodiments will so fully reveal the general nature of the disclosure that others can, by applying knowledge within the skill of the relevant art(s) (including the contents of the documents cited and incorporated by reference herein), readily modify and/or adapt for various applications such specific embodiments, without undue experimentation, without departing from the general concept of the present disclosure. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

While various embodiments of the present disclosure have been described above, it should be understood that they have been presented by way of examples, and not limitation. It would be apparent to one skilled in the relevant art(s) that various changes in form and detail could be made therein without departing from the spirit and scope of the disclosure. Thus, the present disclosure should not be limited by any of the above-described exemplary embodiments, but should be defined only in accordance with the following claims and their equivalents.

Exemplary Embodiments are Set Out in the Following Items

Item 1. A compound represented by the structure of formula (I):

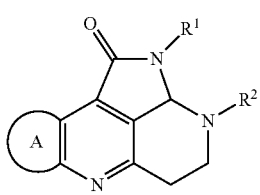

(I)

or a derivative of compound (I) selected from the group consisting of:

(a) an iminium form of compound (I) represented by the structure of formula (I-a):

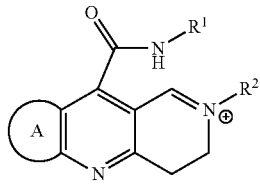

(I-a)

(b) a compound represented by the structure of formula (I-b):

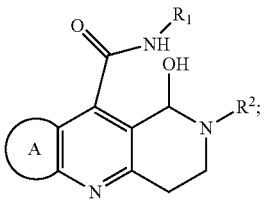

(I-b)

(c) a compound represented by the structure of formula (I-c):

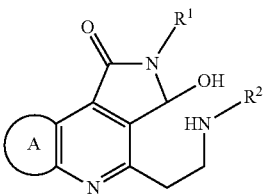

(I-c)

wherein
A is absent, or an unsubstituted or substituted cycloalkyl, aryl, ferrocenyl, heterocycloalkyl or heteroaryl group;
$R^1$ is selected from the group consisting of alkyl, cycloalkyl, aryl, ferrocenyl, heterocycloalkyl, heteroaryl, cycloalkylalkyl, arylalkyl, heterocycloalkylaryl, heteroarylalkyl, each of which is unsubstituted or substituted with at least one $R^3$;
$R^2$ is selected from the group consisting of H, alkyl, haloalkyl, hydroxyalkyl, cyanoalkyl, aminoalkyl, sulfonylalkyl, alkenyl, cycloalkyl, aryl, ferrocenyl, heterocycloalkyl, heteroaryl, arylalkyl, cycloalkylalkyl, heterocycloalkylalkyl, heteroarylalkyl, alkyloxyalkyl, aryloxyalkyl, heteroalkyloxyalkyl, heterocycloalkyloxyalkyl, $-SO_2R^b$, $-(CRR')_mC(O)R^a$, $-(CRR')_mC(O)OR^a$, and $-(CRR')_mC(O)NRR'$;
$R^3$ is independently at each occurrence selected from the group consisting of halogen, CN, hydroxy, alkyloxy, aryloxy, cycloalkyloxy, heterocycloalkyloxy, heteroaryloxy $-SO_2R^b$, NRR' and $-NHC(=O)R$;
$R^a$, R and R' are each independently H or alkyl;
$R^b$ is H, alkyl or NRR';
m is 0, 1, 2, 3, 4, 5 or 6;
and enantiomers, diastereomers, polymorphs, salts, solvates and deuterated analogues thereof.

Item 2. The compound according to item 1, which is represented by the structure of formula (I).

Item 3. The compound according to item 1, wherein ring A is absent, or an unsubstituted or substituted cyclohexyl, phenyl or pyridyl.

Item 4. The compound according to item 3, wherein ring A is a phenyl which is unsubstituted or substituted with a halogen.

Item 5. The compound according to item 1, wherein $R^1$ is an unsubstituted or substituted phenyl, benzyl, alkyl, cycloalkyl or heterocycloalkyl.

Item 6. The compound according to item 1, wherein $R^1$ is an unsubstituted or substituted phenyl represented by the structure:

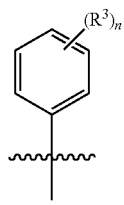

wherein $R^3$ is as defined in claim 1, and n is selected from the group consisting of 1, 2, 3, 4 and 5.

Item 7. The compound according to item 6, wherein $R^3$ is selected from the group consisting of halogen, alkyloxy and cyano, and n is 1 or 2.

Item 8. The compound according to item 6, wherein $R^3$ is selected from the group consisting chloro, fluoro, bromo, methoxy, cyano and hexahydrofurofuranyloxy.

Item 9. The compound according to item 1, wherein $R^2$ is selected from the group consisting of H, an unsubstituted or substituted benzyl, phenethyl, piperazinyl, pyridinylalkyl, pyrimidinylalkyl, thiazolylalkyl, pyrazolylalkyl, imidazolylalkyl, triazolylalkyl, allyl, alkyl, carbomethoxyalkyl, cyclopropylalkyl, ethoxyalkyl, tetrahydropyranyloxylalkyl, haloalkyl, cyanoalkyl, hydroxyalkyl, N,N-dimethylcarboxamidoalkyl, —C(=O)—CH$_2$OR$^a$ wherein R$^a$ is alkyl, phthalimidealkyl, aminoalkyl, N,N-dimethylaminoalkyl, sulfonylalkyl and carboxyalkyl.

Item 10. The compound according to item 9, wherein $R^2$ is selected from the group consisting of an unsubstituted or substituted benzyl, phenethyl and alkyl.

Item 11. A pharmaceutical composition comprising a compound according to item 1, and a pharmaceutically acceptable excipient.

Item 12. A method of treating or inhibiting malaria, or reducing the symptoms of malaria, comprising the step of administering to a subject in need thereof a therapeutically effective amount of a compound of formula (I) (I-a), (I-b) or (I-c) according to item 1, or a pharmaceutical composition comprising such compound.

Item 13. A method of treating or inhibiting malaria, or reducing the symptoms of malaria, comprising the step of administering to a subject in need thereof a therapeutically effective amount of a compound represented by the structure of formula (II), or a pharmaceutical composition comprising such compound wherein
A is absent, or an unsubstituted or substituted cycloalkyl, aryl, heterocycloalkyl or heteroaryl group;
$R^1$ is selected from the group consisting of alkyl, cycloalkyl, aryl, heterocycloalkyl, heteroaryl, cycloalkylalkyl, arylalkyl, heterocycloalkylaryl, heteroarylalkyl, each of which is unsubstituted or substituted with at least one $R^3$;
$R^2$ is selected from the group consisting of H, alkyl, haloalkyl, hydroxyalkyl, cyanoalkyl, aminoalkyl, sulfonylalkyl, alkenyl, cycloalkyl, aryl, heterocycloalkyl, heteroaryl, arylalkyl, cycloalkylalkyl, heterocycloalkylalkyl, heteroarylalkyl, alkyloxyalkyl, aryloxyalkyl, heteroalkyloxyalkyl, heterocycloalkyloxyalkyl, —SO$_2$R$^b$, —(CRR')$_m$C(O)R$^a$, —(CRR')$_m$C(O)OR$^a$, and —(CRR')$_m$C(O)NRR';
$R^3$ is independently at each occurrence selected from the group consisting of halogen, CN, hydroxy, alkyloxy, aryloxy, cycloalkyloxy, heterocycloalkyloxy, heteroaryloxy —SO$_2$R$^b$, NRR' and —NHC(=O)R;
$R^a$, R and R' are each independently H or alkyl;
$R^b$ is H, alkyl or NRR';
m is 0, 1, 2, 3, 4, 5 or 6;
and enantiomers, diastereomers, polymorphs, salts, solvates and deuterated analogues thereof.

Item 14. The method according to item 13, wherein ring A is a phenyl which is unsubstituted or substituted with a halogen.

Item 15. The method according to item 13, wherein $R^1$ is an unsubstituted or substituted phenyl represented by the structure:

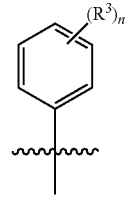

wherein $R^3$ is as defined in item 1, and n is selected from the group consisting of 1, 2, 3, 4 and 5.

Item 16. The method according to item 15, wherein $R^3$ is selected from the group consisting of halogen, alkyloxy and cyano, and n is 1 or 2.

Item 17. The method according to item 15, wherein $R^3$ is selected from the group consisting chloro, fluoro, bromo, methoxy, cyano and hexahydrofurofuranyloxy.

Item 18. The method according to item 13, wherein $R^2$ is selected from the group consisting of an unsubstituted or substituted benzyl, phenethyl and alkyl.

Item 19. A process for preparing a compound represented by the structure of formula (I), or enantiomers, diastereomers, polymorphs, salts, solvates and deuterated analogues thereof

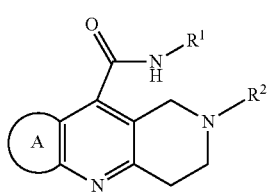

(II)

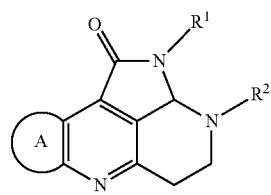

(I)

the process comprising the step of reacting a compound of formula (II) with an oxidizing agent

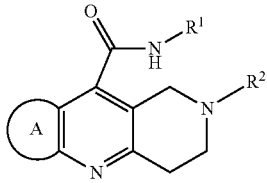

wherein in the compounds of formula (I) or (II)

A is absent, or an unsubstituted or substituted cycloalkyl, aryl, heterocycloalkyl or heteroaryl group;

R¹ is selected from the group consisting of alkyl, cycloalkyl, aryl, heterocycloalkyl, heteroaryl, cycloalkylalkyl, arylalkyl, heterocycloalkylaryl, heteroarylalkyl, each of which is unsubstituted or substituted with at least one R³;

R² is selected from the group consisting of H, alkyl, haloalkyl, hydroxyalkyl, cyanoalkyl, aminoalkyl, sulfonylalkyl, alkenyl, cycloalkyl, aryl, heterocycloalkyl, heteroaryl, arylalkyl, cycloalkylalkyl, heterocycloalkylalkyl, heteroarylalkyl, alkyloxyalkyl, aryloxyalkyl, heteroalkyloxyalkyl, heterocycloalkyloxyalkyl, —SO₂Rᵇ, —(CRR')ₘC(O)Rᵃ, —(CRR')ₘC(O)ORᵃ, and —(CRR')ₘC(O)NRR';

R³ is independently at each occurrence selected from the group consisting of halogen, CN, hydroxy, alkyloxy, aryloxy, cycloalkyloxy, heterocycloalkyloxy, heteroaryloxy —SO₂Rᵇ, NRR' and —NHC(=O)R;

Rᵃ, R and R' are each independently H or alkyl;

Rᵇ is H, alkyl or NRR';

m is 0, 1, 2, 3, 4, 5 or 6.

Item 20. The process according to item 19, further comprising the step of converting the compound of compound (I) to a compound of formula (I-a) in the presence of an acid, or hydrolyzing the compound of formula (I) to compound (I-b) or (I-c) in the presence of water.

What is claimed:

1. A compound represented by the structure of formula (I):

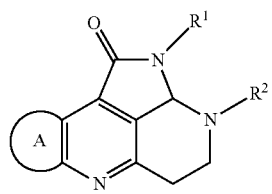

or a derivative of compound (I) selected from the group consisting of:

(a) an iminium form of compound (I) represented by the structure of formula (I-a):

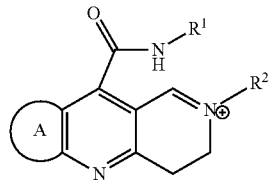

(b) a compound represented by the structure of formula (I-b):

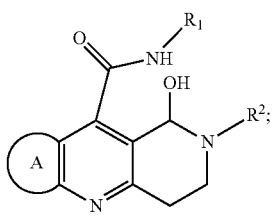

(c) a compound represented by the structure of formula (I-c):

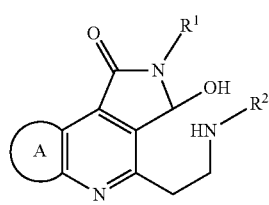

wherein

A is absent, or an unsubstituted or substituted cycloalkyl, aryl, ferrocenyl, heterocycloalkyl or heteroaryl group;

R¹ is selected from the group consisting of alkyl, cycloalkyl, aryl, ferrocenyl, heterocycloalkyl, heteroaryl, cycloalkylalkyl, arylalkyl, heterocycloalkylaryl, heteroarylalkyl, each of which is unsubstituted or substituted with at least one R³;

R² is selected from the group consisting of H, alkyl, haloalkyl, hydroxyalkyl, cyanoalkyl, aminoalkyl, sulfonylalkyl, alkenyl, cycloalkyl, aryl, ferrocenyl, heterocycloalkyl, heteroaryl, arylalkyl, cycloalkylalkyl, heterocycloalkylalkyl, heteroarylalkyl, alkyloxyalkyl, aryloxyalkyl, heteroalkyloxyalkyl, heterocycloalkyloxyalkyl, —SO₂Rᵇ, —(CRR')ₘC(O)Rᵃ, —(CRR')ₘC(O)ORᵃ, and —(CRR')ₘC(O)NRR';

R³ is independently at each occurrence selected from the group consisting of halogen, CN, hydroxy, alkyloxy, aryloxy, cycloalkyloxy, heterocycloalkyloxy, heteroaryloxy —SO₂Rᵇ, NRR' and —NHC(=O)R;

Rᵃ, R and R' are each independently H or alkyl;

Rᵇ is H, alkyl or NRR';

m is 0, 1, 2, 3, 4, 5 or 6;

and enantiomers, diastereomers, polymorphs, salts, solvates and deuterated analogues thereof.

2. The compound according to claim 1, which is represented by the structure of formula (I).

3. The compound according to claim 1, wherein ring A is absent, or an unsubstituted or substituted cyclohexyl, phenyl or pyridyl.

4. The compound according to claim 3, wherein ring A is a phenyl which is unsubstituted or substituted with a halogen.

5. The compound according to claim 1, wherein $R^1$ is an unsubstituted or substituted phenyl, benzyl, alkyl, cycloalkyl or heterocycloalkyl.

6. The compound according to claim 1, wherein $R^1$ is an unsubstituted or substituted phenyl represented by the structure:

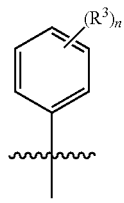

wherein $R^3$ is as defined in claim 1, and n is selected from the group consisting of 1, 2, 3, 4 and 5.

7. The compound according to claim 6, wherein $R^3$ is selected from the group consisting of halogen, alkyloxy and cyano, and n is 1 or 2.

8. The compound according to claim 6, wherein $R^3$ is selected from the group consisting chloro, fluoro, bromo, methoxy, cyano and hexahydrofurofuranyloxy.

9. The compound according to claim 1, wherein $R^2$ is selected from the group consisting of H, an unsubstituted or substituted benzyl, phenethyl, piperazinyl, pyridinylalkyl, pyrimidinylalkyl, thiazolylalkyl, pyrazolylalkyl, imidazolylalkyl, triazolylalkyl, allyl, alkyl, carbomethoxyalkyl, cyclopropylalkyl, ethoxyalkyl, tetrahydropyranyloxylalkyl, haloalkyl, cyanoalkyl, hydroxyalkyl, N,N-dimethylcarboxamidoalkyl, —C(=O)—CH$_2$OR$^a$ wherein R$^a$ is alkyl, phthalimidealkyl, aminoalkyl, N,N-dimethylaminoalkyl, sulfonylalkyl and carboxyalkyl.

10. The compound according to claim 9, wherein $R^2$ is selected from the group consisting of an unsubstituted or substituted benzyl, phenethyl and alkyl.

11. A pharmaceutical composition comprising a compound according to claim 1, and a pharmaceutically acceptable excipient.

12. A method of treating or inhibiting malaria, or reducing the symptoms of malaria, comprising the step of administering to a subject in need thereof a therapeutically effective amount of a compound of formula (I) (I-a), (I-b) or (I-c) according to claim 1, or a pharmaceutical composition comprising such compound.

13. A method of treating or inhibiting malaria, or reducing the symptoms of malaria, comprising the step of administering to a subject in need thereof a therapeutically effective amount of a compound represented by the structure of formula (II), or a pharmaceutical composition comprising such compound

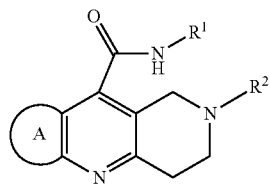

(II)

wherein
A is absent, or an unsubstituted or substituted cycloalkyl, aryl, heterocycloalkyl or heteroaryl group;
$R^1$ is selected from the group consisting of alkyl, cycloalkyl, aryl, heterocycloalkyl, heteroaryl, cycloalkylalkyl, arylalkyl, heterocycloalkylaryl, heteroarylalkyl, each of which is unsubstituted or substituted with at least one $R^3$;
$R^2$ is selected from the group consisting of H, alkyl, haloalkyl, hydroxyalkyl, cyanoalkyl, aminoalkyl, sulfonylalkyl, alkenyl, cycloalkyl, aryl, heterocycloalkyl, heteroaryl, arylalkyl, cycloalkylalkyl, heterocycloalkylalkyl, heteroarylalkyl, alkyloxyalkyl, aryloxyalkyl, heteroalkyloxyalkyl, heterocycloalkyloxyalkyl, —SO$_2$R$^b$, —(CRR')$_m$C(O)R$^a$, —(CRR')$_m$C(O)OR$^a$, and —(CRR')$_m$C(O)NRR';
$R^3$ is independently at each occurrence selected from the group consisting of halogen, CN, hydroxy, alkyloxy, aryloxy, cycloalkyloxy, heterocycloalkyloxy, heteroaryloxy —SO$_2$R$^b$, NRR' and —NHC(=O)R;
R$^a$, R and R' are each independently H or alkyl;
R$^b$ is H, alkyl or NRR';
m is 0, 1, 2, 3, 4, 5 or 6;
and enantiomers, diastereomers, polymorphs, salts, solvates and deuterated analogues thereof.

14. The method according to claim 13, wherein ring A is a phenyl which is unsubstituted or substituted with a halogen.

15. The method according to claim 13, wherein $R^1$ is an unsubstituted or substituted phenyl represented by the structure:

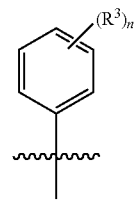

wherein $R^3$ is as defined in claim 1, and n is selected from the group consisting of 1, 2, 3, 4 and 5.

16. The method according to claim 15, wherein $R^3$ is selected from the group consisting of halogen, alkyloxy and cyano, and n is 1 or 2.

17. The method according to claim 15, wherein $R^3$ is selected from the group consisting chloro, fluoro, bromo, methoxy, cyano and hexahydrofurofuranyloxy.

18. The method according to claim 13, wherein $R^2$ is selected from the group consisting of an unsubstituted or substituted benzyl, phenethyl and alkyl.

19. A process for preparing a compound represented by the structure of formula (I), or enantiomers, diastereomers, polymorphs, salts, solvates and deuterated analogues thereof

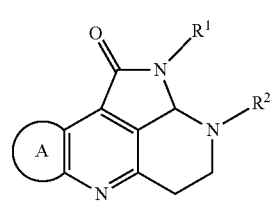

(I)

the process comprising the step of reacting a compound of formula (II) with an oxidizing agent

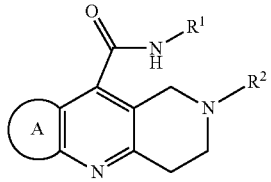

(II)

wherein in the compounds of formula (I) or (II)
A is absent, or an unsubstituted or substituted cycloalkyl, aryl, heterocycloalkyl or heteroaryl group;
R¹ is selected from the group consisting of alkyl, cycloalkyl, aryl, heterocycloalkyl, heteroaryl, cycloalkylalkyl, arylalkyl, heterocycloalkylaryl, heteroarylalkyl, each of which is unsubstituted or substituted with at least one R³;
R² is selected from the group consisting of H, alkyl, haloalkyl, hydroxyalkyl, cyanoalkyl, aminoalkyl, sulfonylalkyl, alkenyl, cycloalkyl, aryl, heterocycloalkyl, heteroaryl, arylalkyl, cycloalkylalkyl, heterocycloalkylalkyl, heteroarylalkyl, alkyloxyalkyl, aryloxyalkyl, heteroalkyloxyalkyl, heterocycloalkyloxyalkyl, —SO₂Rᵇ, —(CRR')ₘC(O)Rᵃ, —(CRR')ₘC(O)ORᵃ, and —(CRR')ₘC(O)NRR';
R³ is independently at each occurrence selected from the group consisting of halogen, CN, hydroxy, alkyloxy, aryloxy, cycloalkyloxy, heterocycloalkyloxy, heteroaryloxy —SO₂Rᵇ, NRR' and —NHC(=O)R;
Rᵃ, R and R' are each independently H or alkyl;
Rᵇ is H, alkyl or NRR';
m is 0, 1, 2, 3, 4, 5 or 6.

20. The process according to claim 19, further comprising the step of converting the compound of compound (I) to a compound of formula (I-a) in the presence of an acid, or hydrolyzing the compound of formula (I) to compound (I-b) or (I-c) in the presence of water.

* * * * *